(12) United States Patent
Lin et al.

(10) Patent No.: US 9,908,918 B2
(45) Date of Patent: Mar. 6, 2018

(54) CYAN-EXCITABLE ORANGE-RED FLUORESCENT PROTEINS AND BIOLUMINESCENT RESONANCE ENERGY TRANSFER SYSTEMS

(71) Applicants: Michael Lin, Stanford, CA (US); Jun Chu, Shenzhen (CN); Younghee Oh, Incheon (KR)

(72) Inventors: Michael Lin, Stanford, CA (US); Jun Chu, Shenzhen (CN); Younghee Oh, Incheon (KR)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 21 days.

(21) Appl. No.: 15/197,772

(22) Filed: Jun. 30, 2016

(65) Prior Publication Data
US 2016/0376332 A1     Dec. 29, 2016

Related U.S. Application Data

(60) Provisional application No. 62/187,165, filed on Jun. 30, 2015.

(51) Int. Cl.
| | |
|---|---|
| A61B 5/00 | (2006.01) |
| A61K 49/00 | (2006.01) |
| C12Q 1/66 | (2006.01) |
| C12N 9/02 | (2006.01) |
| G01N 21/76 | (2006.01) |
| C07K 14/435 | (2006.01) |
| G01N 21/64 | (2006.01) |
| G01N 33/58 | (2006.01) |

(52) U.S. Cl.
CPC ...... *C07K 14/43595* (2013.01); *A61B 5/0071* (2013.01); *A61B 5/0082* (2013.01); *A61K 49/0045* (2013.01); *C12N 9/0069* (2013.01); *C12Q 1/66* (2013.01); *C12Y 113/12007* (2013.01); *G01N 21/6428* (2013.01); *G01N 21/6458* (2013.01); *G01N 21/763* (2013.01); *G01N 33/582* (2013.01); *C07K 2319/60* (2013.01)

(58) Field of Classification Search
None
See application file for complete search history.

(56) References Cited

U.S. PATENT DOCUMENTS

| | | | | |
|---|---|---|---|---|
| 2013/0252282 A1* | 9/2013 | Zhou | .................... | C07K 14/001 435/69.7 |
| 2014/0058065 A1* | 2/2014 | Chu | ................. | C07K 14/43504 530/350 |
| 2016/0376332 A1* | 12/2016 | Lin | ...................... | G01N 33/582 435/8 |

OTHER PUBLICATIONS

Chu et al., "Non-invasive intravital imaging of cellular differentiation with a bright red-excitable fluorescent protein", Nature Methods, vol. 11, No. 5, pp. 572-578, 2014.*

(Continued)

*Primary Examiner* — Robert B Mondesi
*Assistant Examiner* — Richard C Ekstrom

(57) ABSTRACT

Engineered orange-red fluorescent proteins with enhanced fluorescent properties, obtained by mutagenesis of mNeptune2, are disclosed. In particular, the invention relates to engineered orange-red fluorescent proteins excitable with cyan light having increased emission intensity and their use in bioluminescent resonance energy transfer systems and fluorescence and bioluminescence imaging.

14 Claims, 35 Drawing Sheets

```
              -4    1         11         21         31         41         51
       CyOFP    MVSKGEELIKENMRMKLYEEGSVNGHQFKCTEEGEGKPYEGKQTMRIKVVEGGPLPFAFDILAT
    mNeptune    MVSKGEELIKEHMHMKLYMEGTVNHHFKCTEEGEGKPYEGTQTMRIKVVEGGPLPFAFDILAT
                1          11         21         31         41         51

61         71         81         91        101        111
       CyOFP    MFMYGSKVFIKYPADIPDYFKQSFPEGFTWERVMVEEDGGVLTATQDTSLQDGELIYNVK
    mNeptune    EFMYGSKTFIMHEQGIPDFFKQSFPEGFTWERVMTEEDGGVLTATQDTSLQDGCLIYNVK
                61         71         81         91

121        131        141        151        161        171
       CyOFP    VRGVNFPANGPVMQKKTLGWEPSTETMYPADGGLEGRCDMALKLVGGGHLHMNMKTTYKS
    mNeptune    IRGVNFPSNGPVMQKKTLGWEASTETMYPADGGLEGRCDMALKLVGGGHLIMNMKTTYRS
               121        131        141        151        161        171

181        191        201        211        221
       CyOFP    KKP---VKMPGVMYVDRRLERIKEADNETYVEQYEHAVARYSNLGGG-------MDELYK
    mNeptune    KKPAKNLKMPGVMFVDRRLERIKEADNETYVEQHEVAVARYCDLPSKLGHKLNGMDELYK
               181        191        201        211        221        231
```

(56) References Cited

OTHER PUBLICATIONS

Han et al., "In vivo imaging of protein-protein and RNA-protein interactions using novel far-red fluorescence complementation systems", Nucleic Acids Research (2014) e103, doi: 10.1093/narl/gku408.*

* cited by examiner

```
CyOFP    -4
         MVSKGEELIKENMRSKLYLEGSVNGHQFKCTHEGEGKPYEGKQTNRIKVVEGGPLPFAFDILAT
mNeptune  1
         MVSKGEELIKENMHMKKLYMEGTVNNHHFKCTSEGEGKPYEGTQTGRIKVVEGGPLPFAFDILAT
          1       11       21       31       41       51

CyOFP    61
         HFMYGSKVFIKYPADIPDYFKQSFPEGFTWERVMVFEDGGVLTATQDTSLQDGELIYNVK
mNeptune 61
         CFMYGSKTFINHTQGIPDFFKQSFPEGFTWERVTTYEDGGVLTATQDTSLQDGCLIYNVK
          61      71       81       91      101      111

CyOFP    121
         VRGVNFPANGPVMQKKTLGWEPSTETMYPADGGLEGRCDKALKLVGGGHLHVNEKTTYKS
mNeptune 121
         IRGVNFPSNGPVMQKKTLGWEASTETHYPADGGLEGRCDMALKLVGGGHLICNIKTTYRS
          121     131      141      151      161      171

CyOFP    181
         KKP---VKMPGVHYVDRRLERIKEADNETYVEQYEHAVARYSNLGGG------MDELYK
mNeptune 181
         KKPAKNLKMPGVYFVDRRLERIKEADNETYVEQHEVAVARYCDLPSKLGHKLNGMDELYK
          181     191      201      211      221      231
```

FIG. 1B

SEQUENCE LISTING

```
<160> NUMBER OF SEQ ID NOS: 12

<210> SEQ ID NO 1
<211> LENGTH: 230
<212> TYPE: PRT
<213> ORGANISM: Artificial Sequence
<220> FEATURE:
<223> OTHER INFORMATION: CyOFP

<400> SEQUENCE: 1

Met Gly Ser Leu Ile Lys Glu Asn Met Arg Ser Lys Leu Tyr Leu Glu
1               5                   10                  15

Gly Ser Val Asn Gly His Gln Phe Lys Cys Thr His Glu Gly Glu Gly
            20                  25                  30

Lys Pro Tyr Glu Gly Lys Gln Thr Asn Arg Ile Lys Val Val Glu Gly
        35                  40                  45

Gly Pro Leu Pro Phe Ala Phe Asp Ile Leu Ala Thr His Phe Met Tyr
```

-continued

```
                50                  55                  60
Gly Ser Lys Val Phe Ile Lys Tyr Pro Ala Asp Leu Pro Asp Tyr Phe
 65                  70                  75                  80

Lys Gln Ser Phe Pro Glu Gly Phe Thr Trp Glu Arg Val Met Val Phe
                 85                  90                  95

Glu Asp Gly Gly Val Leu Thr Ala Thr Gln Asp Thr Ser Leu Gln Asp
            100                 105                 110

Gly Glu Leu Ile Tyr Asn Val Lys Val Arg Gly Val Asn Phe Pro Ala
        115                 120                 125

Asn Gly Pro Val Met Gln Lys Lys Thr Leu Gly Trp Glu Pro Ser Thr
130                 135                 140

Glu Thr Met Tyr Pro Ala Asp Gly Gly Leu Glu Gly Arg Cys Asp Lys
145                 150                 155                 160

Ala Leu Lys Leu Val Gly Gly His Leu His Val Asn Phe Lys Thr
                165                 170                 175

Thr Tyr Lys Ser Lys Lys Pro Val Lys Met Pro Gly Val His Tyr Val
            180                 185                 190

Asp Arg Arg Leu Glu Arg Ile Lys Glu Ala Asp Asn Glu Thr Tyr Val
        195                 200                 205

Glu Gln Tyr Glu His Ala Val Ala Arg Tyr Ser Asn Leu Gly Gly Gly
    210                 215                 220

Met Asp Glu Leu Tyr Lys
225                 230
```

<210> SEQ ID NO 2
<211> LENGTH: 627
<212> TYPE: PRT
<213> ORGANISM: Artificial Sequence
<220> FEATURE:
<223> OTHER INFORMATION: Antares

<400> SEQUENCE: 2

```
Met Val Ser Lys Gly Glu Glu Leu Ile Lys Glu Asn Met Arg Ser Lys
 1               5                  10                  15

Leu Tyr Leu Glu Gly Ser Val Asn Gly His Gln Phe Lys Cys Thr His
             20                  25                  30

Glu Gly Glu Gly Lys Pro Tyr Glu Gly Lys Gln Thr Asn Arg Ile Lys
         35                  40                  45

Val Val Glu Gly Gly Pro Leu Pro Phe Ala Phe Asp Ile Leu Ala Thr
     50                  55                  60

His Phe Met Tyr Gly Ser Lys Val Phe Ile Lys Tyr Pro Ala Asp Leu
 65                  70                  75                  80

Pro Asp Tyr Phe Lys Gln Ser Phe Pro Glu Gly Phe Thr Trp Glu Arg
                 85                  90                  95

Val Met Val Phe Glu Asp Gly Gly Val Leu Thr Ala Thr Gln Asp Thr
            100                 105                 110

Ser Leu Gln Asp Gly Glu Leu Ile Tyr Asn Val Lys Val Arg Gly Val
        115                 120                 125

Asn Phe Pro Ala Asn Gly Pro Val Met Gln Lys Lys Thr Leu Gly Trp
130                 135                 140

Glu Pro Ser Thr Glu Thr Met Tyr Pro Ala Asp Gly Gly Leu Glu Gly
145                 150                 155                 160

Arg Cys Asp Lys Ala Leu Lys Leu Val Gly Gly His Leu His Val
                165                 170                 175

Asn Phe Lys Thr Thr Tyr Lys Ser Lys Lys Pro Val Lys Met Pro Gly
```

```
            180                 185                 190
Val His Tyr Val Asp Arg Arg Leu Glu Arg Ile Lys Glu Ala Asp Asn
            195                 200                 205
Glu Thr Tyr Val Glu Gln Tyr Glu His Ala Val Ala Arg Tyr Ser Asn
            210                 215                 220
Leu Gly Gly Gly Phe Thr Leu Glu Asp Phe Val Gly Asp Trp Arg Gln
225                 230                 235                 240
Thr Ala Gly Tyr Asn Leu Asp Gln Val Leu Glu Gln Gly Gly Val Ser
            245                 250                 255
Ser Leu Phe Gln Asn Leu Gly Val Ser Val Thr Pro Ile Gln Arg Ile
            260                 265                 270
Val Leu Ser Gly Glu Asn Gly Leu Lys Ile Asp Ile His Val Ile Ile
            275                 280                 285
Pro Tyr Glu Gly Leu Ser Gly Asp Gln Met Gly Gln Ile Glu Lys Ile
            290                 295                 300
Phe Lys Val Val Tyr Pro Val Asp Asp His His Phe Lys Val Ile Leu
305                 310                 315                 320
His Tyr Gly Thr Leu Val Ile Asp Gly Val Thr Pro Asn Met Ile Asp
            325                 330                 335
Tyr Phe Gly Arg Pro Tyr Glu Gly Ile Ala Val Phe Asp Gly Lys Lys
            340                 345                 350
Ile Thr Val Thr Gly Thr Leu Trp Asn Gly Asn Lys Ile Ile Asp Glu
            355                 360                 365
Arg Leu Ile Asn Pro Asp Gly Ser Leu Leu Phe Arg Val Thr Ile Asn
            370                 375                 380
Gly Val Thr Gly Trp Arg Leu Cys Glu Arg Ile Leu Ala Arg His Glu
385                 390                 395                 400
Leu Ile Lys Glu Asn Met Arg Ser Lys Leu Tyr Leu Glu Gly Ser Val
            405                 410                 415
Asn Gly His Gln Phe Lys Cys Thr His Glu Gly Glu Gly Lys Pro Tyr
            420                 425                 430
Glu Gly Lys Gln Thr Asn Arg Ile Lys Val Val Glu Gly Gly Pro Leu
            435                 440                 445
Pro Phe Ala Phe Asp Ile Leu Ala Thr His Phe Met Tyr Gly Ser Lys
            450                 455                 460
Val Phe Ile Lys Tyr Pro Ala Asp Leu Pro Asp Tyr Phe Lys Gln Ser
465                 470                 475                 480
Phe Pro Glu Gly Phe Thr Trp Glu Arg Val Met Val Phe Glu Asp Gly
            485                 490                 495
Gly Val Leu Thr Ala Thr Gln Asp Thr Ser Leu Gln Asp Gly Glu Leu
            500                 505                 510
Ile Tyr Asn Val Lys Val Arg Gly Val Asn Phe Pro Ala Asn Gly Pro
            515                 520                 525
Val Met Gln Lys Lys Thr Leu Gly Trp Glu Pro Ser Thr Glu Thr Met
            530                 535                 540
Tyr Pro Ala Asp Gly Gly Leu Glu Gly Arg Cys Asp Lys Ala Leu Lys
545                 550                 555                 560
Leu Val Gly Gly Gly His Leu His Val Asn Phe Lys Thr Thr Tyr Lys
            565                 570                 575
Ser Lys Lys Pro Val Lys Met Pro Gly Val His Tyr Val Asp Arg Arg
            580                 585                 590
Leu Glu Arg Ile Lys Glu Ala Asp Asn Glu Thr Tyr Val Glu Gln Tyr
            595                 600                 605
```

Glu His Ala Val Ala Arg Tyr Ser Asn Leu Gly Gly Gly Met Asp Glu
            610                 615                 620

Leu Tyr Lys
625

<210> SEQ ID NO 3
<211> LENGTH: 171
<212> TYPE: PRT
<213> ORGANISM: Artificial Sequence
<220> FEATURE:
<223> OTHER INFORMATION: Nanoluc luciferase
<300> PUBLICATION INFORMATION:
<308> DATABASE ACCESSION NUMBER: NCBI/AFJ15588
<309> DATABASE ENTRY DATE: 2014-03-11
<313> RELEVANT RESIDUES IN SEQ ID NO: (1)..(171)

<400> SEQUENCE: 3

Met Val Phe Thr Leu Glu Asp Phe Val Gly Asp Trp Arg Gln Thr Ala
1               5                   10                  15

Gly Tyr Asn Leu Asp Gln Val Leu Glu Gln Gly Gly Val Ser Ser Leu
            20                  25                  30

Phe Gln Asn Leu Gly Val Ser Val Thr Pro Ile Gln Arg Ile Val Leu
        35                  40                  45

Ser Gly Glu Asn Gly Leu Lys Ile Asp Ile His Val Ile Ile Pro Tyr
    50                  55                  60

Glu Gly Leu Ser Gly Asp Gln Met Gly Gln Ile Glu Lys Ile Phe Lys
65                  70                  75                  80

Val Val Tyr Pro Val Asp Asp His His Phe Lys Val Ile Leu His Tyr
                85                  90                  95

Gly Thr Leu Val Ile Asp Gly Val Thr Pro Asn Met Ile Asp Tyr Phe
            100                 105                 110

Gly Arg Pro Tyr Glu Gly Ile Ala Val Phe Asp Gly Lys Lys Ile Thr
        115                 120                 125

Val Thr Gly Thr Leu Trp Asn Gly Asn Lys Ile Ile Asp Glu Arg Leu
    130                 135                 140

Ile Asn Pro Asp Gly Ser Leu Leu Phe Arg Val Thr Ile Asn Gly Val
145                 150                 155                 160

Thr Gly Trp Arg Leu Cys Glu Arg Ile Leu Ala
                165                 170

<210> SEQ ID NO 4
<211> LENGTH: 627
<212> TYPE: PRT
<213> ORGANISM: Artificial Sequence
<220> FEATURE:
<223> OTHER INFORMATION: Antares with H61M CyOFP

<400> SEQUENCE: 4

Met Val Ser Lys Gly Glu Glu Leu Ile Lys Glu Asn Met Arg Ser Lys
1               5                   10                  15

Leu Tyr Leu Glu Gly Ser Val Asn Gly His Gln Phe Lys Cys Thr His
            20                  25                  30

Glu Gly Glu Gly Lys Pro Tyr Glu Gly Lys Gln Thr Asn Arg Ile Lys
        35                  40                  45

Val Val Glu Gly Gly Pro Leu Pro Phe Ala Phe Asp Ile Leu Ala Thr
    50                  55                  60

Met Phe Met Tyr Gly Ser Lys Val Phe Ile Lys Tyr Pro Ala Asp Leu
65                  70                  75                  80

```
Pro Asp Tyr Phe Lys Gln Ser Phe Pro Glu Gly Phe Thr Trp Glu Arg
                85                  90                  95

Val Met Val Phe Glu Asp Gly Val Leu Thr Ala Thr Gln Asp Thr
            100                 105                 110

Ser Leu Gln Asp Gly Glu Leu Ile Tyr Asn Val Lys Val Arg Gly Val
            115                 120                 125

Asn Phe Pro Ala Asn Gly Pro Val Met Gln Lys Lys Thr Leu Gly Trp
            130                 135                 140

Glu Pro Ser Thr Glu Thr Met Tyr Pro Ala Asp Gly Gly Leu Glu Gly
145                 150                 155                 160

Arg Cys Asp Lys Ala Leu Lys Leu Val Gly Gly His Leu His Val
                165                 170                 175

Asn Phe Lys Thr Thr Tyr Lys Ser Lys Lys Pro Val Lys Met Pro Gly
            180                 185                 190

Val His Tyr Val Asp Arg Arg Leu Glu Arg Ile Lys Glu Ala Asp Asn
            195                 200                 205

Glu Thr Tyr Val Glu Gln Tyr Glu His Ala Val Ala Arg Tyr Ser Asn
            210                 215                 220

Leu Gly Gly Gly Phe Thr Leu Glu Asp Phe Val Gly Asp Trp Arg Gln
225                 230                 235                 240

Thr Ala Gly Tyr Asn Leu Asp Gln Val Leu Glu Gln Gly Gly Val Ser
                245                 250                 255

Ser Leu Phe Gln Asn Leu Gly Val Ser Val Thr Pro Ile Gln Arg Ile
            260                 265                 270

Val Leu Ser Gly Glu Asn Gly Leu Lys Ile Asp Ile His Val Ile Ile
            275                 280                 285

Pro Tyr Glu Gly Leu Ser Gly Asp Gln Met Gly Gln Ile Glu Lys Ile
            290                 295                 300

Phe Lys Val Val Tyr Pro Val Asp His His Phe Lys Val Ile Leu
305                 310                 315                 320

His Tyr Gly Thr Leu Val Ile Asp Gly Val Thr Pro Asn Met Ile Asp
                325                 330                 335

Tyr Phe Gly Arg Pro Tyr Glu Gly Ile Ala Val Phe Asp Gly Lys Lys
            340                 345                 350

Ile Thr Val Thr Gly Thr Leu Trp Asn Gly Asn Lys Ile Ile Asp Glu
            355                 360                 365

Arg Leu Ile Asn Pro Asp Gly Ser Leu Leu Phe Arg Val Thr Ile Asn
            370                 375                 380

Gly Val Thr Gly Trp Arg Leu Cys Glu Arg Ile Leu Ala Arg His Glu
385                 390                 395                 400

Leu Ile Lys Glu Asn Met Arg Ser Lys Leu Tyr Leu Glu Gly Ser Val
                405                 410                 415

Asn Gly His Gln Phe Lys Cys Thr His Glu Gly Glu Gly Lys Pro Tyr
            420                 425                 430

Glu Gly Lys Gln Thr Asn Arg Ile Lys Val Val Glu Gly Gly Pro Leu
            435                 440                 445

Pro Phe Ala Phe Asp Ile Leu Ala Thr Met Phe Met Tyr Gly Ser Lys
450                 455                 460

Val Phe Ile Lys Tyr Pro Ala Asp Leu Pro Asp Tyr Phe Lys Gln Ser
465                 470                 475                 480

Phe Pro Glu Gly Phe Thr Trp Glu Arg Val Met Val Phe Glu Asp Gly
                485                 490                 495

Gly Val Leu Thr Ala Thr Gln Asp Thr Ser Leu Gln Asp Gly Glu Leu
```

```
                    500                 505                 510
Ile Tyr Asn Val Lys Val Arg Gly Val Asn Phe Pro Ala Asn Gly Pro
            515                 520                 525

Val Met Gln Lys Lys Thr Leu Gly Trp Glu Pro Ser Thr Glu Thr Met
        530                 535                 540

Tyr Pro Ala Asp Gly Gly Leu Glu Gly Arg Cys Asp Lys Ala Leu Lys
545                 550                 555                 560

Leu Val Gly Gly Gly His Leu His Val Asn Phe Lys Thr Thr Tyr Lys
                565                 570                 575

Ser Lys Lys Pro Val Lys Met Pro Gly Val His Tyr Val Asp Arg Arg
            580                 585                 590

Leu Glu Arg Ile Lys Glu Ala Asp Asn Glu Thr Tyr Val Glu Gln Tyr
        595                 600                 605

Glu His Ala Val Ala Arg Tyr Ser Asn Leu Gly Gly Gly Met Asp Glu
    610                 615                 620

Leu Tyr Lys
625

<210> SEQ ID NO 5
<211> LENGTH: 4
<212> TYPE: PRT
<213> ORGANISM: Artificial Sequence
<220> FEATURE:
<223> OTHER INFORMATION: linker

<400> SEQUENCE: 5

Gly Gly Ser Gly
1

<210> SEQ ID NO 6
<211> LENGTH: 4
<212> TYPE: PRT
<213> ORGANISM: Artificial Sequence
<220> FEATURE:
<223> OTHER INFORMATION: linker

<400> SEQUENCE: 6

Ser Ala Gly Gly
1

<210> SEQ ID NO 7
<211> LENGTH: 5
<212> TYPE: PRT
<213> ORGANISM: Artificial Sequence
<220> FEATURE:
<223> OTHER INFORMATION: linker

<400> SEQUENCE: 7

Gly Gly Gly Gly Ser
1               5

<210> SEQ ID NO 8
<211> LENGTH: 5
<212> TYPE: PRT
<213> ORGANISM: Artificial Sequence
<220> FEATURE:
<223> OTHER INFORMATION: nucleus targeting sequence

<400> SEQUENCE: 8

Lys Lys Lys Arg Lys
1               5
```

```
<210> SEQ ID NO 9
<211> LENGTH: 26
<212> TYPE: PRT
<213> ORGANISM: Artificial Sequence
<220> FEATURE:
<223> OTHER INFORMATION: mitochondria targeting sequence

<400> SEQUENCE: 9

Met Leu Arg Thr Ser Ser Leu Phe Thr Arg Arg Val Gln Pro Ser Leu
1               5                   10                  15

Phe Arg Asn Ile Leu Arg Leu Gln Ser Thr
            20                  25

<210> SEQ ID NO 10
<211> LENGTH: 4
<212> TYPE: PRT
<213> ORGANISM: Artificial Sequence
<220> FEATURE:
<223> OTHER INFORMATION: endoplasmic reticulum targeting sequence

<400> SEQUENCE: 10

Lys Asp Glu Leu
1

<210> SEQ ID NO 11
<211> LENGTH: 4
<212> TYPE: PRT
<213> ORGANISM: Artificial Sequence
<220> FEATURE:
<223> OTHER INFORMATION: plasma membrane targeting sequence
<220> FEATURE:
<221> NAME/KEY: misc_feature
<222> LOCATION: (2)..(3)
<223> OTHER INFORMATION: Xaa is an aliphatic amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 11

Cys Xaa Xaa Xaa
1

<210> SEQ ID NO 12
<211> LENGTH: 4
<212> TYPE: PRT
<213> ORGANISM: Artificial Sequence
<220> FEATURE:
<223> OTHER INFORMATION: plasma membrane targeting sequence
<220> FEATURE:
<221> NAME/KEY: misc_feature
<222> LOCATION: (3)..(4)
<223> OTHER INFORMATION: Xaa can be any naturally occurring amino acid

<400> SEQUENCE: 12

Cys Cys Xaa Xaa
1
```

CYAN-EXCITABLE ORANGE-RED FLUORESCENT PROTEINS AND BIOLUMINESCENT RESONANCE ENERGY TRANSFER SYSTEMS

STATEMENT REGARDING FEDERALLY SPONSORED RESEARCH OR DEVELOPMENT

This invention was made with Government support under contract GM111003 awarded by the National Institutes of Health. The Government has certain rights in this invention.

TECHNICAL FIELD

The present invention pertains generally to engineered orange-red fluorescent proteins with enhanced fluorescent properties. In particular, the invention relates to engineered orange-red fluorescent proteins excitable with cyan light having increased emission intensity and their use in bioluminescent resonance energy transfer systems and fluorescence and bioluminescence imaging.

BACKGROUND

Fluorescent proteins are useful in living cells and in vitro as components in reporters of gene expression, of cell abundance or location, of protein abundance or location, or of biochemical activities (Newman et al. (2011) Chem Rev 111:3614-3666). In these studies, researchers often desire to simultaneously assay two events, such as the expression of two genes, the abundance or location of two cell populations, the abundance and location of two proteins, or the occurrence and location of two biochemical activities (Depry et al. (2013) Pflugers Arch 465:373-381). This is possible with the use of two fluorescent protein labels of different colors. For instance, simultaneous dual-event imaging can be performed with a green fluorescent protein (GFP) and a red fluorescent protein (RFP) by exciting the GFP with blue or cyan light and exciting the RFP with green or yellow light. However, fluorescent proteins of different emission wavelengths usually have different excitation wavelengths, necessitating the use of two different excitation bands. This can be expensive when truly simultaneous excitation is needed, as it would necessitate a dual-bandpass filter in cases where wide-spectrum light sources are used, or two light-emitting diodes or lasers in cases where these single-wavelength light sources are used. In the case of two-photon-mode excitation, the Ti-Sapphire lasers used also are weaker in the wavelengths required for RFP excitation.

One strategy for reporting two biological processes with fluorescent proteins has been to use an RFP that can be excited by blue light (420-460 nm) together with cyan fluorescent proteins (CFPs), which are also excited by blue light (Kogure et al. (2008) Methods 45:223-226). Several blue-excitable RFPs, also termed long-Stokes-shift RFPs, have been developed and visualized simultaneously with CFP with blue excitation (Kogure et al. (2006) Nat Biotechnol 24:577-581; Piatkevich et al. (2010) PNAS USA 107:5369-5374; Yang et al. (2013) PLoS One 8:e64849). However, these RFPs have quantum yields of at most 0.27 (Table 1), far lower than the >0.6 of commonly used GFPs and CFPs (Lam et al. (2012) Nat Methods 9:1005-1012). Furthermore, the blue wavelengths required to excite them can cause phototoxicity and autofluorescence in cells due to their absorbance by flavin compounds. Furthermore, the vast majority of existing reporters use GFP, which is not well excited by blue wavelengths of light, rather than CFP, so imaging two biochemical activities using blue-excitable RFPs would usually require modification of existing GFP-based reporters to use CFP.

Another type of imaging in biological research that has been limited by technical performance has been bioluminescence imaging (BLI) in living animals. BLI refers to imaging of light produced by luciferase enzymes by oxidation of chemical substrates. In rodent preclinical studies, BLI performed on cells expressing non-secreted luciferases offers relatively cheap and simple means for in vivo tracking of cells, for example to assess stem cell survival or tumor growth (Close et al. (2011) Sensors (Basel) 11:180-206). For imaging in animals, luciferases that have high rates of production of red photons (above 600 nm) are preferred, as red light is capable of avoiding absorbance by hemoglobin and thereby transmits through tissue more readily. Much effort has thus been spent searching for luciferases with higher activity and redder emission. The second-generation firefly luciferase FLuc2 is currently most commonly used in animals, and has peak emission near 600 nm, but very low catalysis rates of 1.6 reactions per second with a bioluminescence quantum yield of 0.41 (Branchini et al. (1998) Biochemistry 37:15311-15319; Ando et al. (2007) Nature Photonics 2:44-47). Some non-secreted luciferases from marine organisms, such as those from *Renilla* and *Cypridina* species, have higher catalytic activities, but emit natively at wavelengths below 500 nm and with lower bioluminescent quantum yield (Shimomura et al. (1969) Science 164:1299-1300; Matthews et al. (1977) Biochemistry 16:85-91). *Renilla* luciferase has been engineered to emit at up to 550 nm (Loening et al. (2010) Nat Methods 7:5-6), but these wavelengths are still efficiently absorbed by hemoglobin. Nano luciferase (NLuc), a recently engineered version of a luciferase from the shrimp *Oplophorus*, has approximately 100× faster catalysis than FLuc2 (Shimomura et al. (1978) Biochemistry 17:994-998), but its output is even bluer, peaking at 460 nm, and it has not been demonstrated to improve detectability in vivo versus FLuc2 (Hall et al. (2012) ACS Chem Biol 7:1848-1857). In comparisons in animals, FLuc2 remained the most sensitive reporter for BLI imaging (Mezzanotte et al. (2013) Contrast Media Mol. Imaging 8:505-513).

Thus, there remains a need for fluorescent and bioluminescent proteins that improve detection and lower toxicity for use in fluorescence imaging and bioluminescence imaging.

SUMMARY

The invention relates to engineered orange-red fluorescent proteins with enhanced fluorescent properties obtained by mutagenesis of mNeptune2. In particular, the invention relates to engineered orange-red fluorescent proteins excitable with cyan light having increased emission intensities and their use in bioluminescent resonance energy transfer systems and fluorescence and bioluminescence imaging.

In one aspect, the invention includes an orange-red fluorescent protein comprising the amino acid sequence of SEQ ID NO:1 or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto, wherein the orange-red fluorescent protein emits light in response to absorption of cyan excitation light. In one embodiment, the orange-red fluorescent protein comprises a variant polypeptide, wherein the amino acid corresponding to His 61 numbered relative to the reference sequence of SEQ ID NO:1 is replaced with a methionine.

In certain embodiments, the invention includes a fusion protein comprising an orange-red fluorescent protein, as described herein, connected to a polypeptide of interest. The polypeptide of interest may be from any protein of interest for which attachment of a fluorescent label is desired, such as, but not limited to, a membrane protein, a receptor, a hormone, a transport protein, a channel protein, a transcription factor, a cytoskeletal protein, an extracellular matrix protein, a signal-transduction protein, and an enzyme. The fusion protein may comprise an entire selected protein of interest, or a biologically active domain (e.g., a catalytic domain, a ligand binding domain, or a protein-protein interaction domain), or a polypeptide fragment of the selected protein of interest.

Fusion proteins may further comprise one or more linkers connecting polypeptides within the fusion protein. Linkers are typically short peptide sequences of 2-30 amino acid residues, often composed of glycine and/or serine residues.

Additionally, fusion proteins may further comprise a targeting sequence, for example, that directs localization of the fusion protein to a specific tissue, cell-type (e.g. muscle, heart, or neural cell), cellular compartment (e.g., mitochondria or other organelle, nucleus, cytoplasm, or plasma membrane), or protein. Targeting sequences that can be used in the practice of the invention include, but are not limited to a secretory protein signal sequence, a membrane protein signal sequence, a nuclear localization sequence, a nucleolar localization signal sequence, an endoplasmic reticulum localization sequence, a peroxisome localization sequence, a mitochondrial localization sequence, and a protein-protein interaction motif sequence.

In certain embodiments, the fusion protein may include additional fluorescent or bioluminescent proteins, or biologically active domains or polypeptide fragments, or variants thereof having fluorescence or bioluminescence characteristics (e.g., green fluorescent protein (GFP) or luciferase).

In certain embodiments, the invention includes a bioluminescent fusion protein comprising at least one orange-red fluorescent protein, as described herein, connected to at least one luciferase, wherein the orange-red fluorescent protein is operably linked to the luciferase to allow bioluminescence resonance energy transfer (BRET) between the orange-red fluorescent protein, which serves as a fluorescent BRET acceptor and a luciferase reaction product, which serves as a bioluminescent BRET donor upon reaction of a chemiluminescent substrate at the active site of the luciferase.

In certain embodiments, the bioluminescent fusion protein comprises at least two orange-red fluorescent proteins, as described herein, connected to a luciferase, wherein a first orange-red fluorescent protein is connected to the N-terminus of the luciferase and a second orange-red fluorescent protein is connected to the C-terminus of the luciferase, wherein each orange-red fluorescent protein is operably linked to the luciferase to allow BRET between the orange-red fluorescent protein, which serves as a fluorescent BRET acceptor and the luciferase reaction product, which serves as a bioluminescent BRET donor in response to exposure to a chemiluminescent substrate. In one embodiment, the first or second orange-red fluorescent protein in the bioluminescent fusion protein comprises the amino acid sequence of SEQ ID NO:1 or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto, wherein the orange-red fluorescent protein emits light in response to absorption of cyan excitation light.

In certain embodiments, the amino acid corresponding to His 61 numbered relative to the sequence of SEQ ID NO:1 is replaced with a methionine in the first orange-red fluorescent protein or the second orange-red fluorescent protein. In other embodiments, the amino acid corresponding to His 61 numbered relative to the sequence of SEQ ID NO:1 is replaced with a methionine in both the first orange-red fluorescent protein and the second orange-red fluorescent protein.

In another embodiment, the luciferase in the bioluminescent fusion protein comprises the amino acid sequence of SEQ ID NO:3, or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto, wherein the luciferase emits luminescence in response to exposure to a chemiluminescent substrate.

In certain embodiments, the bioluminescent fusion protein comprises an amino acid sequence selected from the group consisting of SEQ ID NO:2 and SEQ ID NO:4, or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto, wherein the fusion protein emits light in response to exposure to a chemiluminescent substrate.

In certain embodiments, the bioluminescent fusion protein further comprises a polypeptide of interest, wherein the polypeptide of interest is covalently connected to the bioluminescent fusion protein. Additionally, the bioluminescent fusion protein may further comprise one or more linkers, targeting sequences, tags, labels, or other sequences.

In another embodiment, the invention includes a bioluminescence resonance energy transfer (BRET) system comprising a bioluminescent fusion protein described herein and a chemiluminescent substrate (e.g., coelenterazine, furimazine or other coelenterazine analog, or other luciferase substrate). In one embodiment, the BRET system further comprises a device for detecting light emitted from the bioluminescent fusion protein, such as, but not limited to an optical microscope, a digital microscope, a luminometer, a charged coupled device (CCD) image sensor, a complementary metal-oxide-semiconductor (CMOS) image sensor, or a digital camera.

In another aspect, the invention includes a polynucleotide encoding an orange-red fluorescent protein or bioluminescent fusion protein described herein. In one embodiment, the invention includes a recombinant polynucleotide comprising a polynucleotide encoding the orange-red fluorescent protein or bioluminescent fusion protein operably linked to a promoter. The recombinant polynucleotide may comprise a plasmid or a viral vector comprising a promoter operably linked to a polynucleotide sequence encoding the progenitor cell programming agent. In certain embodiments, the recombinant polynucleotide comprises a viral expression vector, such as, but not limited to, an adenovirus, retrovirus (e.g., γ-retrovirus and lentivirus), poxvirus, adeno-associated virus, baculovirus, or herpes simplex virus vector. In one embodiment, the viral vector is a replication deficient viral vector. In certain embodiments, the promoter is a cell-type specific promoter, for example, a neuron-specific promoter, a muscle-specific promoter, or a cardiac-specific promoter.

In another aspect, the invention includes a host cell comprising a recombinant polynucleotide encoding an orange-red fluorescent protein or bioluminescent fusion protein operably linked to a promoter. In certain embodiments, the host cell is an excitable cell, such as, but not limited to, a neuron, a cardiac cell, or an endocrine cell. In other embodiments, the host cell is a non-excitable cell, such as, but not limited to, a glial cell, a bone cell, an intestinal cell, a pancreatic cell, a prostate cell, and a kidney cell.

In another aspect, the invention includes a reporter gene construct comprising a recombinant polynucleotide encoding an orange-red fluorescent protein or a bioluminescent fusion protein, as described herein, operably linked to a transcriptional regulatory region of interest. The regulatory region of interest can be, for example, a promoter or an enhancer. In one embodiment, the reporter gene construct further comprises a polynucleotide sequence encoding a gene of interest operably linked to the transcriptional regulatory region of interest.

In another embodiment, the invention includes a host cell comprising a reporter gene construct described herein. The host cell may further comprise an expression vector encoding a test agent of interest (e.g., DNA binding protein or a ligand for a receptor) operably linked to a promoter.

In another embodiment, the invention includes a reporter gene assay comprising: a) introducing a test agent into a host cell comprising a reporter gene construct comprising a recombinant polynucleotide encoding an orange-red fluorescent protein operably linked to a transcriptional regulatory region of interest; b) illuminating the cell with cyan light at an excitation wavelength of the orange-red fluorescent protein; and c) measuring the level of expression of the orange-red fluorescent protein by detecting fluorescence emitted by the orange-red fluorescent protein, wherein the intensity of the fluorescence indicates the expression level of the orange-red fluorescent protein in the cell.

In another embodiment, the invention includes a reporter gene assay comprising: a) introducing a test agent into a host cell comprising a reporter gene construct comprising a recombinant polynucleotide encoding a bioluminescent fusion protein operably linked to a transcriptional regulatory region of interest; b) contacting the cell with a chemiluminescent substrate; and c) measuring the level of expression of the bioluminescent fusion protein by detecting luminescence emitted by the bioluminescent fusion protein, wherein the intensity of the luminescence indicates the expression level of the bioluminescent fusion protein in the cell.

In another aspect, the invention includes a method for fluorescent labeling a cell. In one embodiment, the method comprises introducing an orange-red fluorescent protein described herein into the cell. In another embodiment, the method comprises: transfecting the cell with a recombinant polynucleotide comprising a polynucleotide sequence encoding an orange-red fluorescent protein, described herein, operably linked to a promoter, whereby the orange-red fluorescent protein is expressed in the cell.

In another aspect, the invention includes a method of using the orange-red fluorescent protein described herein for fluorescence imaging, the method comprising: a) introducing the orange-red fluorescent protein into a cell; b) illuminating the cell with light at a fluorescence excitation wavelength of the orange-red fluorescent protein; and c) recording a fluorescence image of the cell by detecting fluorescence emitted by the orange-red fluorescent protein. One or more fluorescence images may be recorded, for example, with a fluorescence microscope, a digital microscope, a charged coupled device (CCD) image sensor, a complementary metal-oxide-semiconductor (CMOS) image sensor, a digital camera, a fiber-optic fluorescence imaging system, or a medical fluorescence imaging device (e.g., a handheld fluorescence microscope, a laparoscope, an endoscope, or a microendoscope). In one embodiment, the orange-red fluorescent protein is provided by a vector expressing the orange-red fluorescent protein.

In certain embodiments, fluorescence imaging may be performed with an orange-red fluorescent protein, as described herein, and at least one additional fluorophore. Preferably, all fluorophores can be excited at the same wavelength. In one embodiment, the method comprises: a) introducing an orange-red fluorescent protein into a cell; b) introducing a green fluorescent protein into the cell; c) illuminating the cell with light at an excitation wavelength that produces fluorescence from both the orange-red fluorescent protein and the green fluorescent protein simultaneously; and d) recording a fluorescence image of the cell by detecting fluorescence emitted by the orange-red fluorescent protein and the green fluorescent protein.

In another aspect, the invention includes a method for bioluminescent labeling a cell. In one embodiment, the method comprises introducing a bioluminescent fusion protein described herein into the cell. In another embodiment, the method comprises transfecting the cell with a recombinant polynucleotide comprising a polynucleotide sequence encoding a bioluminescent fusion protein, described herein, operably linked to a promoter, whereby the bioluminescent fusion protein is expressed.

In another aspect, the invention includes a method of using a bioluminescent fusion protein described herein for bioluminescence imaging, the method comprising: a) introducing the bioluminescent fusion protein into a cell; b) contacting the bioluminescent fusion protein with a chemiluminescent substrate in the cell; and c) recording a bioluminescence image of the cell by detecting bioluminescence emitted from the fusion protein. One or more bioluminescence images may be recorded, for example, with an optical microscope, a digital microscope, a luminometer, a charged coupled device (CCD) image sensor, a complementary metal-oxide-semiconductor (CMOS) image sensor, a digital camera, a fiber-optic imaging system, or a medical imaging device (e.g., a handheld microscope, a laparoscope, an endoscope, or a microendoscope). In one embodiment, the bioluminescent fusion protein is provided by a vector expressing the bioluminescent fusion protein.

In certain embodiments, bioluminescence imaging may be performed with a bioluminescent fusion protein, as described herein, and at least one additional protein having fluorescence or bioluminescence characteristics. In one embodiment, the method comprises: a) introducing the bioluminescent fusion protein into a cell; b) contacting the bioluminescent fusion protein with a chemiluminescent substrate in the cell; c) introducing a green fluorescent protein into the cell; d) illuminating the cell with light at an excitation wavelength of the green fluorescent protein; and e) recording an image of the cell by detecting both fluorescence emitted by the green fluorescent protein and bioluminescence emitted by the bioluminescent fusion protein.

Bioluminescence and fluorescence may be monitored by any suitable method, for example, using an optical microscope, a digital microscope, a CCD image sensor, a CMOS image sensor, a fluorescence microscope, a fluorimeter, a luminometer, a fluorescence microplate reader, a fluorometric imaging plate reader, fluorescence-activated cell sorting, a fiber-optic fluorescence imaging system, or a medical fluorescence or bioluminescence imaging device (e.g., a handheld microscope, laparoscope, endoscope, or microendoscope modified with a detector and/or excitation light source).

Additionally, bioluminescence and fluorescence images may be recorded by any suitable method. For example, a CCD image sensor, CMOS image sensor, or digital camera may be used to capture images. The image may be a still photo or a video in any format (e.g., bitmap, Graphics Interchange Format, JPEG file interchange format, TIFF, or mpeg). Alternatively, images may be captured by an analog camera and converted into an electronic form. Fluorescence and bioluminescence imaging of cells and tissues may be useful in various fields of medicine, including but not limited to oncology, neurology, orthopedics, cardiology, immunology, and stem cell therapy.

In another embodiment, the invention includes a method of performing fluorescence image-guided surgery on a tissue of interest, the method comprising: a) contacting a tissue of interest with an orange-red fluorescent protein; b) illuminating the tissue of interest with light at a fluorescence excitation wavelength of the orange-red fluorescent protein; and c) detecting fluorescence emitted by the orange-red fluorescent protein with a medical fluorescence imaging device. In one embodiment, the medical fluorescence imaging device is a miniaturized fluorescence imaging system (e.g., a handheld fluorescence microscope, a laparoscope, an endoscope, or a microendoscope). Fluorescence images may be recorded, for example, by a charge-coupled device (CCD) image sensor, a CMOS image sensor, or a digital camera.

In another embodiment, the invention includes a method of performing bioluminescence image-guided surgery on a tissue of interest, the method comprising: a) contacting a tissue of interest with a bioluminescent fusion protein; b) contacting the bioluminescent fusion protein with a chemiluminescent substrate in the tissue; and detecting bioluminescence emitted by the bioluminescent fusion protein with a medical bioluminescence imaging device. In one embodiment, the medical bioluminescence imaging device is a miniaturized bioluminescence imaging system (e.g., a handheld microscope, a laparoscope, an endoscope, or a microendoscope). Bioluminescence images may be recorded, for example, by a charge-coupled device (CCD) image sensor, a CMOS image sensor, or a digital camera.

Fluorescence or bioluminescence imaging may be used, for example, for detection of pathology, evaluation of the completeness of resection, visualization of critical structures, or evaluation of the efficacy of treatment.

In another aspect, the invention includes a method for producing an orange-red fluorescent protein, the method comprising: a) transforming a host cell with a recombinant polynucleotide comprising a polynucleotide sequence encoding the orange-red fluorescent protein operably linked to a promoter; b) culturing the transformed host cell under conditions whereby the orange-red fluorescent protein is expressed; and c) isolating the orange-red fluorescent protein from the host cell.

In another aspect, the invention includes a method for producing a bioluminescent fusion protein, the method comprising: a) transforming a host cell with a recombinant polynucleotide comprising a polynucleotide sequence encoding the bioluminescent fusion protein operably linked to a promoter; b) culturing the transformed host cell under conditions whereby the bioluminescent fusion protein is expressed; and c) isolating the bioluminescent fusion protein from the host cell.

In another aspect, the invention includes a kit for preparing or using an orange-red fluorescent protein or bioluminescent fusion protein according to the methods described herein. Such kits may comprise one or more orange-red fluorescent proteins or bioluminescent fusion proteins or nucleic acids encoding such orange-red fluorescent proteins or bioluminescent fusion proteins, or expression vectors, or cells, or other reagents for preparing an orange-red fluorescent protein or bioluminescent fusion protein, as described herein. The orange-red fluorescent proteins or bioluminescent fusion proteins described herein can be used as labels or reporters in many fluorescent or bioluminescent assays. Such assays are well-known in the art. Therefore, kits may also include reagents for performing such assays. In certain embodiments, the kit further includes a chemiluminescent substrate, a BRET system, or a reporter gene construct utilizing an orange-red fluorescent protein or bioluminescent fusion protein, as described herein.

These and other embodiments of the subject invention will readily occur to those of skill in the art in view of the disclosure herein.

BRIEF DESCRIPTION OF THE FIGURES

FIGS. 1A-1D show development of CyOFP, a cyan-excitable orange-red fluorescent protein. FIG. 1A shows normalized excitation and emission spectra of CyOFP. FIG. 1B shows a sequence alignment of CyOFP and mNeptune. Amino acids forming the chromophore are underlined. Interior mutations are in light gray and outer barrel mutations are colored dark gray. Mutations in the upper loop (when the barrel is oriented with termini pointing upwards) are colored medium gray. Amino acid numbering begins at −4 so that homologous sequences are numbered as in PDB file 3IP2 for the structure of Neptune. FIG. 1C shows fluorescence images of HeLa CCL2 cells expressing CyOFP fused to various domains. For each fusion, the linker amino acid (aa) length is indicated in between the two domains, and the origin of the fusion partner and its normal subcellular location are indicated in parentheses. i, CyOFP-18aa-actin (β-actin, actin cytoskeleton); ii, Cx43-7aa-CyOFP (rat α-1 connexin 43, gap junctions); iii, CytERM-17aa-CyOFP (rabbit cytochrome p450 aa1-29, endoplasmic reticulum); iv, CyOFP-14aa-RhoB (human RhoB, endosomes); v, CyOFP-5aa-CAAX (human c-Ha-Ras 20-amino acid farnesylation signal, plasma membrane); vi, Tractin-11aa-CyOFP (rat F-Tractin; actin cytoskeleton); vii, SiT-7aa-CyOFP, human sialyltransferase aa1-45, Golgi apparatus); viii, COX8A-7aa-CyOFP (human cytochrome C oxidase subunit VIIIA; mitochondria); ix, CyOFP-18aa-tubulin (human α-tubulin, microtubules). FIG. 1D shows fluorescence images of CyOFP-10aa-H2B (human histone 2B) in HeLa S3 cells; i, interphase; ii, prophase; iii, metaphase; and iv, anaphase. Scale bars, 10 μm.

FIG. 2A shows cutaway views of CyOFP (left) and LSSm-Kate (right) with the main chain in cartoon format and chromophores and their hydrogen-bonding partners in stick format. In both proteins, the side chain of amino acid 160 serves as a hydrogen bond donor and excited state proton transfer (ESPT) acceptor. FIG. 2B shows a proposed ESPT in CyOFP. The proton from the phenolic hydroxyl group of the chromophore is transferred to the Lys160 after the chromophore excited by cyan light. Hydrogen bonds are represented as dashed black lines. FIG. 2C shows the CyOFP chromophore (top) is more coplanar than the LSSmKate1 chromophore (middle), and is engaged in two hydrogen bonds compared to one in LSSmKate1. The hydrogen bond partners of the CyOFP chromophore are similar to those of the DsRed chromphore (bottom).

FIG. 3A shows two-photon excitation spectra of CyOFP, GCaMP6s, EGFP, and fluorescein (as reference standard). Error bars are standard deviation. n=3 for CyOFP, 4 for GCaMP6s, 2 for EGFP, and 4 for fluorescein. FIG. 3B shows single optical section (upper row) and surface rendering (lower row) of tractin-CyOFP and cytosolic EGFP in MV3 melanoma cells acquired by two-photon Bessel-beam light-sheet microscopy. CyOFP is localized to the cortex of the cell and small membrane protrusions. FIG. 3C shows fluorescence images of CyOFP and GCaMP6s in layer-2/3 pyramidal neurons in mouse brain V1 cortex in a single optical section acquired by two-photon excitation at 940 nm. FIG. 3D shows GCaMP6s responses of three mouse neurons co-expressing CyOFP in response to drifting gratings. Single sweeps (grey) and averages of 5 sweeps (dark gray) are overlaid. Directions of grating motion (8 directions) are shown above traces (arrows).

FIG. 4A shows that NLuc and CyOFP are well matched for BRET, as the emission spectrum of NanoLuc overlaps the absorbance spectrum of CyOFP. FIG. 4B shows a protein engineering flow chart leading to Antares. Numbers in parentheses refer to the first and last amino acid of the domain fragment contained in the fusion protein, with numbering as in FIG. 1B. Linker sequences are indicated in single-letter amino acid code. Deletions of the C-terminus of NanoLuc yielded inactive enzyme and were not pursued further. FIG. 4C shows emission spectra of the constructs depicted in FIG. 4B. Spectra were normalized to the NanoLuc emission peak at 460 nm. Higher 584-nm emission peaks indicate higher BRET efficiencies.

FIG. 5A shows that Antares is many-fold brighter than other bioluminescence reporters in cells. Cells expressing the indicated reporters with the indicated substrates were injected into a mouse phantom at 0.7-cm depth, and images were acquired in an IVIS Spectrum for 1 s in bioluminescence mode. Although peak pixel intensity of Antares was 46325 counts, the displayed intensity range was set to 0-5000 to allow visual confirmation of signal from all reporter proteins. FIG. 5B shows quantitation of cellular bioluminescence in phantom mice. Total counts were normalized to co-expressed CFP intensity and then normalized to mean counts from Antares with FRZ. The second-brightest reporter-substrate combination, BRET6 with sCTZ, produced 21% of the detectable emission of Antares with FRZ. Error bars are standard error of the mean (n=3). FIG. 5C shows that in mice, Antares with FRZ (330 nmol injected intravenously) is brighter than both BRET6 with sCTZ (330 nmol injected intravenously) and FLuc2 with luciferin (3 mg injected intraperitoneally). Mice were imaged in an IVIS Spectrum in bright-field mode (left image in each pair) or in bioluminescence mode for 2 s (right image). FIG. 5D shows quantification of bioluminescence in living mice. Total counts were normalized to mean counts from Antares with FRZ. The second-brightest reporter-substrate combination, BRET6 with sCTZ, produced 26% of the detectable emission of Antares with FRZ. Error bars are standard error of the mean (n=10 for FLuc2, n=12 for BRET6, and n=9 for Antares).

FIG. 6A shows emission of CyOFP compared to other orange FPs, mOrange, DsRed and CyOFP. The visible spectrum with separated with definitions for blue, green, yellow, orange, and red from the *CRC Handbook of Spectroscopic Correlation Charts* is shown above. FIG. 6B shows fluorescence lifetime decay of CyOFP following a single pulse from a Ti-Sapphire laser, fit to a monoexponential decay function with τ=3.66 ns. Emission in each time bin was normalized by the maximum photons counted at peak (71203). FIG. 6C shows pH dependence of CyOFP fluorescence showing a pKa of 5.5. FIG. 6D shows photobleaching kinetics of purified proteins in oil under arc lamp illumination with a 615/20-nm excitation filter. Time was scaled so that emission was normalized to 1000 photons per s. Each curve is the mean of three independent experiments.

FIG. 7A shows (Left) excitation and emission spectra of CyOFP0.5 and CyOFP0.5 with the single mutation K163M demonstrating the importance of Lys160 in the large Stokes' shift. Inset shows streaks of bacteria expressing CyOFP0.5 (left) and CyOFP0.5-K160M (right) in visible light. FIG. 7B shows absorbance spectra of CyOFP at different pHs. Postulated lysine/phenol charge states are: A, cationic/cationic; B, cationic/neutral; C, neutral/neutral; D, neutral/anionic. FIG. 7C shows chromophore structures in DsRed and LSS orange-red FPs. In DsRed, Lys160 donates a hydrogen bond to the anionic form of the chromophore. In LSS orange-red FPs, ESPT occurs to a Glu residue (LSSmKate1) or to a Ser residue followed by relay to an Asp residue (LSSmOrange, mKeima, mBeRFP, LSSmKate2). Numbering follows that of mNeptune.

FIG. 8A shows absorbance spectra (dashed lines) and emission spectra (solid lines) spectra of GFP (dark gray lines) and CyOFP (light gray lines). Absorbance is presented as extinction coefficient while emission spectra are normalized to peak. FIG. 8B shows single-wavelength dual-color imaging of purified EGFP and CyOFP in vitro (10 μM each). FIG. 8C shows optical section (upper row) and surface rendering (bottom row) of CyOFP-tractin and cytosolic EGFP in MV3 melanoma cells acquired by single-photon axially swept light-sheet microscopy. Surface reconstruction shows CyOFP localization to non-apoptotic membrane blebs. FIG. 8D shows photostability of cytosolic CyOFP under single-photon excitation in light-sheet microscopy over multiple stacks of 126 z-sections each spaced 160 nm apart. Small-intensity fluctuations are due to intensity variations of the laser illumination. FIG. 8E shows photostability of cytosolic CyOFP under two-photon excitation in Bessel beam light-sheet microscopy over multiple stacks of 126 z-sections each spaced 160 nm apart.

FIG. 9A shows emission spectra of N-terminal truncations of NanoLuc, including CN2. FIG. 9B shows comparison of CN2 and CN3. FIG. 9C shows emission spectra of N-terminal truncations of CyOFP, including NC2. FIG. 9D shows emission spectra of linker variants of NanoLuc, including CN3. For measurement of raw bioluminescence (left charts), bacterial lysates were prepared and analyzed in parallel. Constructs were chosen primarily for BRET efficiency in normalized spectra, which is independent of protein concentrations. However, when BRET efficiency was similar between two constructs, the construct with higher raw counts beyond 600 nm was chosen. When constructs were similar in both normalized emissions and raw emissions, the shorter linker was chosen.

DETAILED DESCRIPTION

Figure 1A:
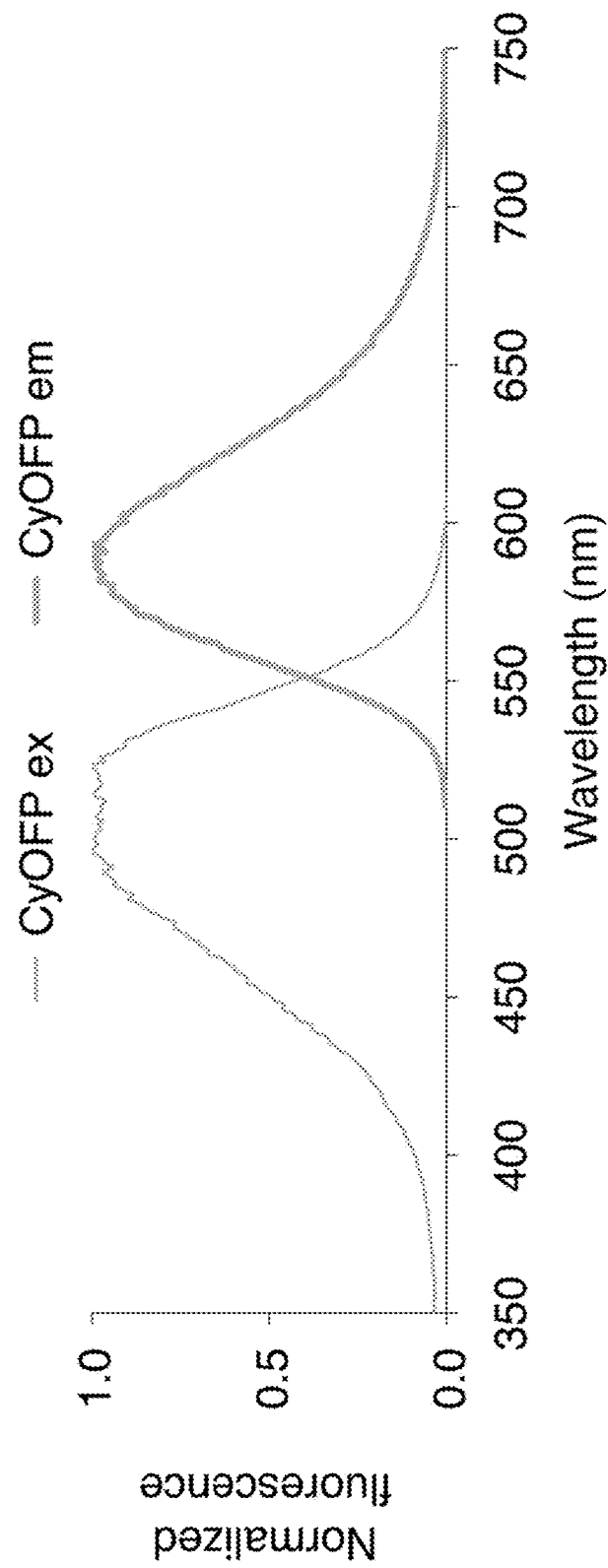

The practice of the present invention will employ, unless otherwise indicated, conventional methods of medicine, cell biology, chemistry, biochemistry, molecular biology, and recombinant DNA techniques, within the skill of the art. Such techniques are explained fully in the literature. See, e.g., S. S. Gambhir and S. S. Yaghoubi *Molecular Imaging with Reporter Genes* (Cambridge Molecular Imaging Series, Cambridge University Press, 2010); *Imaging Cellular and Molecular Biological Functions* (S. L. Shorte and F. Frischknecht eds., Springer, 2007); P. P. Mondal and A. Diaspro *Fundamentals of Fluorescence Microscopy* (Springer Netherlands, 2013); L. Brovko *Bioluminescence and Fluorescence for In Vivo Imaging* (SPIE Press, 2010); J. R. Lakowicz *Principles of Fluorescence Spectroscopy* (Springer; 3$^{rd}$ edition, 2011); *Bioluminescence: Methods and Protocols* (Methods in Molecular Biology, P. B. Rich, C. Douillet eds., Humana Press, 2$^{nd}$ edition, 2009); R. Yuste *Imaging: A Laboratory Manual* (Cold Spring Harbor Laboratory Press, 2010); *Biochemistry* (Worth Publishers, Inc., current addition); Sambrook, et al., *Molecular Cloning: A Laboratory Manual* (3$^{rd}$ Edition, 2001); *Methods In Enzymology* (S. Colowick and N. Kaplan eds., Academic Press, Inc.).

All publications, patents and patent applications cited herein, whether supra or infra, are hereby incorporated by reference in their entireties.

I. Definitions

In describing the present invention, the following terms will be employed, and are intended to be defined as indicated below.

It must be noted that, as used in this specification and the appended claims, the singular forms "a," "an" and "the" include plural referents unless the content clearly dictates otherwise. Thus, for example, reference to "a protein" includes a mixture of two or more proteins, and the like.

The term "about," particularly in reference to a given quantity, is meant to encompass deviations of plus or minus five percent.

"Fluorescent protein" refers to any protein capable of emitting light when excited with appropriate electromagnetic radiation. Fluorescent proteins include proteins having amino acid sequences that are either natural or engineered (e.g., orange fluorescent protein (OFP), red fluorescent protein (RFP), green fluorescent protein (GFP), and variants and derivatives thereof).

The term "fluorescence characteristics" means an ability to emit fluorescence by irradiation of excitation light. The fluorescence characteristics of an orange-red fluorescent protein may be comparable to or different from those of the orange-red fluorescent protein which has the amino acid sequence of SEQ ID NO:1. Examples of parameters of fluorescence characteristics include fluorescence intensity, excitation wavelength, fluorescence wavelength, and pH sensitivity.

The term "bioluminescence characteristics" refers to the ability of a luciferase, or a variant or biologically active fragment thereof, to catalyze a reaction with a chemiluminescent substrate that produces light. The bioluminescence characteristics of a luciferase, or a variant or biologically active fragment thereof, may be comparable to or different from those of the luciferase polypeptide which has the amino acid sequence of SEQ ID NO:3. Examples of parameters of bioluminescence characteristics include biolumines- cence intensity, bioluminescence wavelength, luciferase activity, substrate selectivity, and pH sensitivity.

The terms "polypeptide" and "protein" refer to a polymer of amino acid residues and are not limited to a minimum length. Thus, peptides, oligopeptides, dimers, multimers, and the like, are included within the definition. Both full length proteins and fragments thereof are encompassed by the definition. The terms also include postexpression modifications of the polypeptide, for example, glycosylation, acetylation, phosphorylation, hydroxylation, and the like. Furthermore, for purposes of the present invention, a "polypeptide" refers to a protein which includes modifications, such as deletions, additions and substitutions to the native sequence, so long as the protein maintains the desired activity. These modifications may be deliberate, as through site directed mutagenesis, or may be accidental, such as through mutations of hosts which produce the proteins or errors due to PCR amplification.

By "derivative" is intended any suitable modification of the native polypeptide of interest, of a fragment of the native polypeptide, or of their respective analogs, such as glycosylation, phosphorylation, polymer conjugation (such as with polyethylene glycol), or other addition of foreign moieties, as long as the desired biological activity or fluorescence or bioluminescence characteristics of the native polypeptide is retained. Methods for making polypeptide fragments, analogs, and derivatives are generally available in the art.

The terms "fusion protein" and "fusion polypeptide," as used herein, refer to a fusion comprising at least one orange-red fluorescent protein in combination with a selected polypeptide of interest as part of a single continuous chain of amino acids, which chain does not occur in nature. The orange-red fluorescent protein and other selected polypeptides may be connected directly to each other by peptide bonds or may be separated by intervening amino acid sequences. The fusion polypeptides may also contain sequences exogenous to the orange-red fluorescent protein or other selected polypeptides. For example, the fusion may include targeting or localization sequences, tag sequences, sequences of other fluorescent proteins (e.g., other proteins with fluorescence characteristics that differ from CyOFP), or other chromophores. Moreover, the fusion may contain sequences from multiple fluorescent or bioluminescent proteins, or variants thereof, and/or other selected proteins.

The terms "bioluminescent fusion protein" and "bioluminescent fusion polypeptide," as used herein, refer to a fusion protein comprising at least one orange-red fluorescent protein connected to at least one luciferase, wherein the orange-red fluorescent protein is operably linked to the luciferase to allow bioluminescence resonance energy transfer (BRET) between the orange-red fluorescent protein, which serves as a fluorescent BRET acceptor and a luciferase reaction product, which serves as a bioluminescent BRET donor upon reaction of a chemiluminescent substrate at the active site of the luciferase.

By "fragment" is intended a molecule consisting of only a part of the intact full length sequence and structure. The fragment can include a C-terminal deletion an N-terminal deletion, and/or an internal deletion of the polypeptide. Active fragments of a particular protein or polypeptide will generally include at least about 5-10 contiguous amino acid residues of the full length molecule, preferably at least about 15-25 contiguous amino acid residues of the full length molecule, and most preferably at least about 20-50 or more contiguous amino acid residues of the full length molecule, or any integer between 5 amino acids and the full length sequence, provided that the fragment in question retains biological activity, such as catalytic activity, ligand binding activity, regulatory activity, or fluorescence, or bioluminescence characteristics, as defined herein.

"Substantially purified" generally refers to isolation of a substance (compound, polynucleotide, protein, polypeptide, polypeptide composition) such that the substance comprises the majority percent of the sample in which it resides. Typically in a sample, a substantially purified component comprises 50%, preferably 80%-85%, more preferably 90-95% of the sample. Techniques for purifying polynucleotides and polypeptides of interest are well-known in the art and include, for example, ion-exchange chromatography, affinity chromatography and sedimentation according to density.

By "isolated" is meant, when referring to a polypeptide, that the indicated molecule is separate and discrete from the whole organism with which the molecule is found in nature or is present in the substantial absence of other biological macro molecules of the same type. The term "isolated" with respect to a polynucleotide is a nucleic acid molecule devoid, in whole or part, of sequences normally associated with it in nature; or a sequence, as it exists in nature, but having heterologous sequences in association therewith; or a molecule disassociated from the chromosome.

As used herein, the terms "label" and "detectable label" refer to a molecule capable of detection, including, but not limited to, radioactive isotopes, fluorescers, chemiluminescers, enzymes, enzyme substrates, enzyme cofactors, enzyme inhibitors, chromophores, dyes, metal ions, metal sols, ligands (e.g., biotin or haptens) and the like. The term "fluorescer" refers to a substance or a portion thereof which is capable of exhibiting fluorescence in the detectable range. The term also includes fluorescent or bioluminescent proteins and polypeptides.

"Homology" refers to the percent identity between two polynucleotide or two polypeptide moieties. Two nucleic acid, or two polypeptide sequences are "substantially homologous" to each other when the sequences exhibit at least about 50% sequence identity, preferably at least about 75% sequence identity, more preferably at least about 80%-85% sequence identity, more preferably at least about 90% sequence identity, and most preferably at least about 95%-98% sequence identity over a defined length of the molecules. As used herein, substantially homologous also refers to sequences showing complete identity to the specified sequence.

In general, "identity" refers to an exact nucleotide to nucleotide or amino acid to amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in Atlas of Protein Sequence and Structure M. O. Dayhoff ed., 5 Suppl. 3:353 358, National biomedical Research Foundation, Washington, D.C., which adapts the local homology algorithm of Smith and Waterman Advances in Appl. Math. 2:482 489, 1981 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non redundant, GenBank+EMBL+DDBJ+PDB+GenBank CDS translations+Swiss protein+Spupdate+PIR. Details of these programs are readily available.

Alternatively, homology can be determined by hybridization of polynucleotides under conditions which form stable duplexes between homologous regions, followed by digestion with single stranded specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; DNA Cloning, supra; Nucleic Acid Hybridization, supra.

"Recombinant" as used herein to describe a nucleic acid molecule means a polynucleotide of genomic, cDNA, viral, semisynthetic, or synthetic origin which, by virtue of its origin or manipulation, is not associated with all or a portion of the polynucleotide with which it is associated in nature. The term "recombinant" as used with respect to a protein or polypeptide means a polypeptide produced by expression of a recombinant polynucleotide. In general, the gene of interest is cloned and then expressed in transformed organisms, as described further below. The host organism expresses the foreign gene to produce the protein under expression conditions.

The term "transformation" refers to the insertion of an exogenous polynucleotide into a host cell, irrespective of the method used for the insertion. For example, direct uptake, transduction or f-mating are included. The exogenous polynucleotide may be maintained as a non-integrated vector, for example, a plasmid, or alternatively, may be integrated into the host genome.

"Recombinant host cells", "host cells," "cells", "cell lines," "cell cultures," and other such terms denoting microorganisms or higher eukaryotic cell lines cultured as unicellular entities refer to cells which can be, or have been, used as recipients for recombinant vector or other transferred DNA, and include the original progeny of the original cell which has been transfected.

A "coding sequence" or a sequence that "encodes" a selected polypeptide is a nucleic acid molecule which is transcribed (in the case of DNA) and translated (in the case of mRNA) into a polypeptide in vivo when placed under the control of appropriate regulatory sequences (or "control elements"). The boundaries of the coding sequence can be determined by a start codon at the 5' (amino) terminus and a translation stop codon at the 3' (carboxy) terminus. A coding sequence can include, but is not limited to, cDNA from viral, prokaryotic or eukaryotic mRNA, genomic DNA sequences from viral or prokaryotic DNA, and even synthetic DNA sequences. A transcription termination sequence may be located 3' to the coding sequence.

Typical "control elements," include, but are not limited to, transcription promoters, transcription enhancer elements, transcription termination signals, polyadenylation sequences (located 3' to the translation stop codon), sequences for optimization of initiation of translation (located 5' to the coding sequence), and translation termination sequences.

"Operably linked" refers to an arrangement of elements wherein the components so described are configured so as to perform their usual function. Thus, a given promoter operably linked to a coding sequence is capable of effecting the expression of the coding sequence when the proper enzymes are present. The promoter need not be contiguous with the coding sequence, so long as it functions to direct the expression thereof. Thus, for example, intervening untranslated yet transcribed sequences can be present between the promoter sequence and the coding sequence and the promoter sequence can still be considered "operably linked" to the coding sequence.

A bioluminescent fusion protein comprising an orange-red fluorescent protein operably linked to a luciferase is capable of bioluminescence resonance energy transfer (BRET) between the orange-red fluorescent protein, which serves as a fluorescent BRET acceptor and a luciferase reaction product, which serves as a bioluminescent BRET donor upon reaction of a chemiluminescent substrate at the active site of the luciferase.

"Encoded by" refers to a nucleic acid sequence which codes for a polypeptide sequence, wherein the polypeptide sequence or a portion thereof contains an amino acid sequence of at least 3 to 5 amino acids, more preferably at least 8 to 10 amino acids, and even more preferably at least 15 to 20 amino acids from a polypeptide encoded by the nucleic acid sequence.

"Expression cassette" or "expression construct" refers to an assembly which is capable of directing the expression of the sequence(s) or gene(s) of interest. An expression cassette generally includes control elements, as described above, such as a promoter which is operably linked to (so as to direct transcription of) the sequence(s) or gene(s) of interest, and often includes a polyadenylation sequence as well. Within certain embodiments of the invention, the expression cassette described herein may be contained within a plasmid construct. In addition to the components of the expression cassette, the plasmid construct may also include, one or more selectable markers, a signal which allows the plasmid construct to exist as single stranded DNA (e.g., a M13 origin of replication), at least one multiple cloning site, and a "mammalian" origin of replication (e.g., a SV40 or adenovirus origin of replication).

"Purified polynucleotide" refers to a polynucleotide of interest or fragment thereof which is essentially free, e.g., contains less than about 50%, preferably less than about 70%, and more preferably less than about at least 90%, of the protein with which the polynucleotide is naturally associated. Techniques for purifying polynucleotides of interest are well-known in the art and include, for example, disruption of the cell containing the polynucleotide with a chaotropic agent and separation of the polynucleotide(s) and proteins by ion-exchange chromatography, affinity chromatography and sedimentation according to density.

The term "transfection" is used to refer to the uptake of foreign DNA by a cell. A cell has been "transfected" when exogenous DNA has been introduced inside the cell membrane. A number of transfection techniques are generally known in the art. See, e.g., Graham et al. (1973) Virology, 52:456, Sambrook et al. (2001) Molecular Cloning, a laboratory manual, 3rd edition, Cold Spring Harbor Laboratories, New York, Davis et al. (1995) Basic Methods in Molecular Biology, 2nd edition, McGraw-Hill, and Chu et al. (1981) Gene 13:197. Such techniques can be used to introduce one or more exogenous DNA moieties into suitable host cells. The term refers to both stable and transient uptake of the genetic material, and includes uptake of recombinant polynucleotides encoding fluorescent protein voltage sensors.

A "vector" is capable of transferring nucleic acid sequences to target cells (e.g., viral vectors, non-viral vectors, particulate carriers, and liposomes). Typically, "vector construct," "expression vector," and "gene transfer vector," mean any nucleic acid construct capable of directing the expression of a nucleic acid of interest and which can transfer nucleic acid sequences to target cells. Thus, the term includes cloning and expression vehicles, as well as viral vectors.

The terms "variant," "analog" and "mutein" refer to biologically active derivatives of the reference molecule that retain desired activity, such as fluorescence (e.g., cyan excitable orange-red fluorescent emission) or bioluminescence characteristics (e.g., luciferase activity). In general, the terms "variant" and "analog" refer to compounds having a native polypeptide sequence and structure with one or more amino acid additions, substitutions (generally conservative in nature) and/or deletions, relative to the native molecule, so long as the modifications do not destroy biological activity and which are "substantially homologous" to the reference molecule as defined below. In general, the amino acid sequences of such analogs will have a high degree of sequence homology to the reference sequence, e.g., amino acid sequence homology of more than 50%, generally more than 60%-70%, even more particularly 80%-85% or more, such as at least 90%-95% or more, when the two sequences are aligned. Often, the analogs will include the same number of amino acids but will include substitutions, as explained herein. The term "mutein" further includes polypeptides having one or more amino acid-like molecules including but not limited to compounds comprising only amino and/or imino molecules, polypeptides containing one or more analogs of an amino acid (including, for example, unnatural amino acids, etc.), polypeptides with substituted linkages, as well as other modifications known in the art, both naturally occurring and non-naturally occurring (e.g., synthetic), cyclized, branched molecules and the like. The term also includes molecules comprising one or more N-substituted glycine residues (a "peptoid") and other synthetic amino acids or peptides. (See, e.g., U.S. Pat. Nos. 5,831,005; 5,877,278; and 5,977,301; Nguyen et al., Chem. Biol. (2000) 7:463-473; and Simon et al., Proc. Natl. Acad. Sci. USA (1992) 89:9367-9371 for descriptions of peptoids). Methods for making polypeptide analogs and muteins are known in the art and are described further below.

As explained above, analogs generally include substitutions that are conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, and tyrosine. Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity. For example, the polypeptide of interest may include up to about 5-10 conservative or non-conservative amino acid substitutions, or even up to about 15-25 conservative or non-conservative amino acid substitutions, or any integer between 5-25, as long as the desired function of the molecule remains intact. One of skill in the art may readily determine regions of the molecule of interest that can tolerate change by reference to Hopp/Woods and Kyte-Doolittle plots, well known in the art.

"Gene transfer" or "gene delivery" refers to methods or systems for reliably inserting DNA or RNA of interest into a host cell. Such methods can result in transient expression of non-integrated transferred DNA, extrachromosomal replication and expression of transferred replicons (e.g., episomes), or integration of transferred genetic material into the genomic DNA of host cells. Gene delivery expression vectors include, but are not limited to, vectors derived from bacterial plasmid vectors, viral vectors, non-viral vectors, alphaviruses, pox viruses and vaccinia viruses.

The term "derived from" is used herein to identify the original source of a molecule but is not meant to limit the method by which the molecule is made which can be, for example, by chemical synthesis or recombinant means.

A polynucleotide "derived from" a designated sequence refers to a polynucleotide sequence which comprises a contiguous sequence of approximately at least about 6 nucleotides, preferably at least about 8 nucleotides, more preferably at least about 10-12 nucleotides, and even more preferably at least about 15-20 nucleotides corresponding, i.e., identical or complementary to, a region of the designated nucleotide sequence. The derived polynucleotide will not necessarily be derived physically from the nucleotide sequence of interest, but may be generated in any manner, including, but not limited to, chemical synthesis, replication, reverse transcription or transcription, which is based on the information provided by the sequence of bases in the region(s) from which the polynucleotide is derived. As such, it may represent either a sense or an antisense orientation of the original polynucleotide.

The terms "subject," "individual," and "patient," are used interchangeably herein and refer to any subject, eukaryotic or prokaryotic, for whom fluorescent or bioluminescent labeling or imaging is desired, including bacteria, protists, fungi, plants, and animals. Subjects may include humans, cattle, dogs, cats, guinea pigs, rabbits, rats, mice, horses, and so on. In some cases, the methods of the invention find use in experimental animals, in veterinary application, and in the development of animal models for disease, including, but not limited to, rodents including mice, rats, and hamsters; and primates.

II. Modes of Carrying Out the Invention

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

The present invention is based on the discovery of orange-red fluorescent proteins with enhanced fluorescent properties. In particular, the inventors have engineered orange-red fluorescent proteins excitable with cyan light having increased emission intensity. The enhanced emission in the orange-red spectrum improves imaging of cells and tissues with reduced interference from background autofluorescence. In addition, the ability to use cyan excitation light (480-520 nm) rather than blue excitation light, which is commonly used for other fluorescent proteins, reduces phototoxicity. The inventors have further shown that their engineered orange-red fluorescent proteins can be used in bioluminescent resonance energy transfer (BRET) systems with luciferase for bioluminescence imaging (see Example 1).

In order to further an understanding of the invention, a more detailed discussion is provided below regarding engineered orange-red fluorescent proteins and their use in bioluminescent resonance energy transfer systems and fluorescence and bioluminescence imaging.

A. Cyan Excitable Orange-Red Fluorescent Proteins and their Use as Acceptors in Bioluminescent Resonance Energy Transfer Systems In one aspect, the invention relates to engineered orange-red fluorescent proteins excitable with cyan light having increased emission intensity. Such orange-red fluorescent proteins can be produced by mutagenesis of Neptune2, a red fluorescent protein derived from eqFP578 of *Entacmaea quadricolor* (see Chu et al. (2014) Nat Methods 11:572-578 for a description of the properties of Neptune 2; herein incorporated by reference). In certain embodiments, the orange-red fluorescent protein comprises the amino acid sequence of SEQ ID NO:1 or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto, wherein the orange-red fluorescent protein emits light in response to absorption of cyan excitation light. Further mutagenesis can be performed to alter the fluorescence characteristics of fluorescent proteins for example to increase the intensity or shift the wavelength of their emissions. In one embodiment, the orange-red fluorescent protein comprises a variant polypeptide, wherein the amino acid corresponding to His 61 numbered relative to the reference sequence of SEQ ID NO:1 is replaced with another amino acid.

Figure 10:
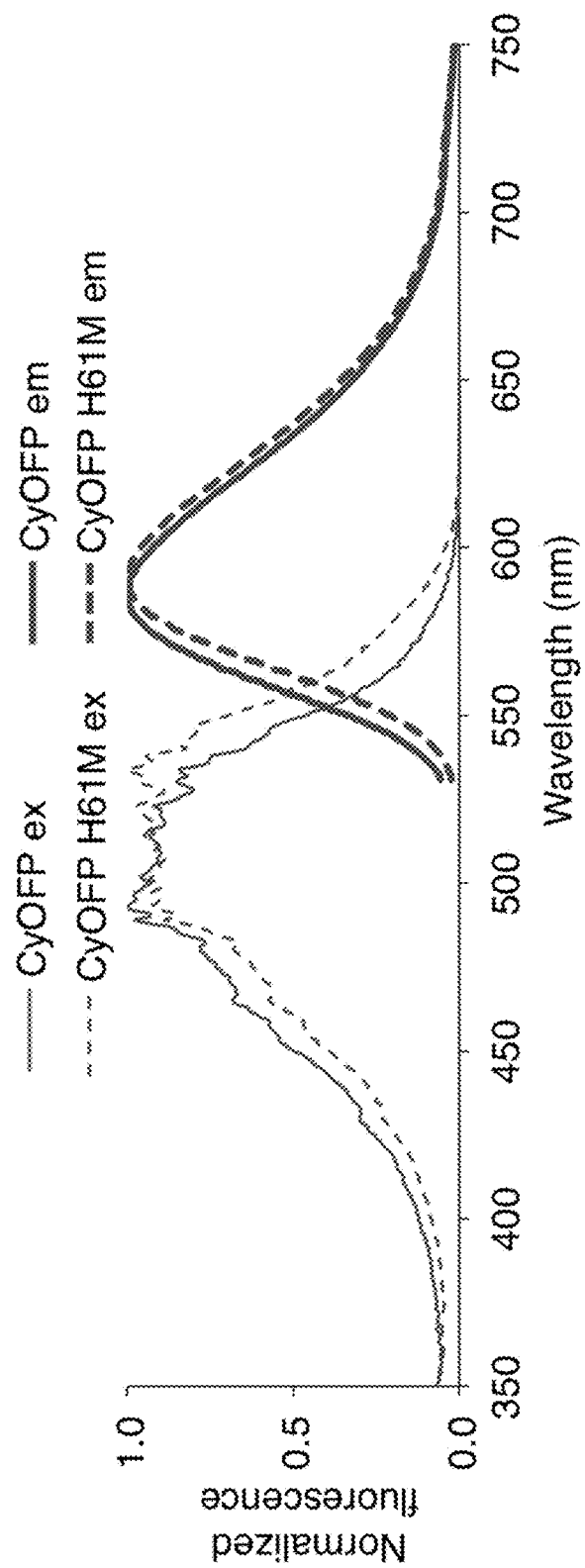
FIG. 10 shows excitation and emission spectra of CyOFP and a red-shifted H61M mutant of CyOFP.

Exemplary orange-red fluorescent proteins are described in Example 1. CyOFP (SEQ ID NO:1) is a cyan-excitable fluorescent protein that exhibits bright orange-red fluorescence. It has a broad excitation spectrum with wavelengths from 488 to 526 nm exciting with >95% of peak efficiency and emits light maximally at 589 nm with more than half of its emission above 600 nm (FIG. 1A, Table 1). A variant of CyOFP comprising an H61M substitution shows a red-shift in its emission spectrum with an excitation peak at 534 nm and an emission peak at 590 nm (FIG. 10).

In certain embodiments, the invention includes a fusion protein comprising an orange-red fluorescent protein, as described herein, connected to a polypeptide of interest. The polypeptide of interest may be from any protein of interest for which attachment of a fluorescent label is desired, such as, but not limited to, a membrane protein, a receptor, a hormone, a transport protein, a channel protein, a transcription factor, a cytoskeletal protein, an extracellular matrix protein, a signal-transduction protein, and an enzyme. The fusion protein may comprise an entire selected protein of interest, or a biologically active domain (e.g., a catalytic domain, a ligand binding domain, or a protein-protein interaction domain), or a polypeptide fragment of the selected protein of interest. Polypeptides included in the fusion construct may be connected directly to each other by peptide bonds or may be separated by intervening amino acid sequences. The fusion polypeptides may also contain sequences exogenous to the orange-red fluorescent protein or the selected protein of interest. For example, the fusion may include targeting or localization sequences, tag sequences, sequences of other fluorescent proteins (e.g., with fluorescence characteristics that differ from the orange-red fluorescent protein), or other chromophores. Moreover, the fusion may contain multiple orange-red fluorescent proteins.

For example, the fusion protein may comprise one or more linkers connecting polypeptides within the fusion protein. Linkers are typically short peptide sequences of 2-30 amino acid residues, often composed of glycine and/or serine residues. Linker amino acid sequences will typically be short, e.g., 20 or fewer amino acids (i.e., 20, 19, 18, 17, 16, 15, 14, 13, 12, 11, 10, 9, 8, 7, 6, 5, 4, 3, 2, or 1). Examples include short peptide sequences which facilitate cloning, poly-glycine linkers ($Gly_n$ where n=2, 3, 4, 5, 6, 7, 8, 9, 10 or more), histidine tags ($His_n$ where n=3, 4, 5, 6, 7, 8, 9, 10 or more), linkers composed of glycine and serine residues ($[Gly-Ser]_n$, $[Gly-Gly-Ser-Gly]_n$ (SEQ ID NO:5), $[Ser-Ala-Gly-Gly]_n$ (SEQ ID NO:6), and $[Gly-Gly-Gly-Gly-Ser]_n$ (SEQ ID NO:7), wherein n=1, 2, 3, 4, 5, 6, 7, 8, 9, 10, 11, 12, 13, 14, 15 or more), GSAT, SEG, and Z-EGFR linkers. Linkers may include restriction sites, which aid cloning and manipulation. Other suitable linker amino acid sequences will be apparent to those skilled in the art. (See e.g., Argos (1990) J. Mol. Biol. 211(4):943-958; Crasto et al. (2000) Protein Eng. 13:309-312; George et al. (2002) Protein Eng. 15:871-879; Arai et al. (2001) Protein Eng. 14:529-532; and the Registry of Standard Biological Parts (partsregistry.org/Protein_domains/Linker).

Additionally, fusion proteins may comprise a targeting sequence. A targeting sequence may direct localization of the fusion protein to a specific tissue, cell-type (e.g. muscle, heart, or neural cell), cellular compartment (e.g., mitochondria or other organelle, nucleus, cytoplasm, or plasma membrane), or protein. Exemplary targeting sequences that can be used in the practice of the invention include a secretory protein signal sequence, a membrane protein signal sequence, a nuclear localization sequence, a nucleolar localization signal sequence, an endoplasmic reticulum localization sequence, a peroxisome localization sequence, a mitochondrial localization sequence, and a protein-protein interaction motif sequence. Examples of targeting sequences include those targeting the nucleus (e.g., KKKRK, SEQ ID NO:8), mitochondrion (e.g., MLRTSSLF-TRRVQPSLFRNILRLQST, SEQ ID NO:9), endoplasmic reticulum (e.g., KDEL, SEQ ID NO:10), peroxisome (e.g., SKL), synapses (e.g., S/TDV or fusion to GAP 43, kinesin or tau), plasma membrane (e.g., CaaX (SEQ ID NO:11) where "a" is an aliphatic amino acid, CC, CXC, CCXX (SEQ ID NO:12) at C-terminus), or protein-protein interaction motifs (e.g., SH2, SH3, PDZ, WW, RGD, Src homology domain, DNA-binding domain, SLiMs).

In certain embodiments, tag sequences are located at the N-terminus or C-terminus of the fusion protein. Exemplary tags that can be used in the practice of the invention include a His-tag, a Strep-tag, a TAP-tag, an S-tag, an SBP-tag, an Arg-tag, a calmodulin-binding peptide tag, a cellulose-binding domain tag, a DsbA tag, a c-myc tag, a glutathione S-transferase tag, a FLAG tag, a HAT-tag, a maltose-binding protein tag, a NusA tag, and a thioredoxin tag.

Fusion proteins may also include additional fluorescent or bioluminescent proteins, or biologically active domains or polypeptide fragments, or variants thereof having fluorescence or bioluminescence characteristics (e.g., green fluorescent protein (GFP) or luciferase).

In certain embodiments, the fusion protein is designed to allow bioluminescence resonance energy transfer (BRET) between the orange-red fluorescent protein and a bioluminescent protein, such as luciferase. The luminescent emission from a luciferase catalyzed reaction can be utilized for excitation of the orange-red fluorescent protein within a fusion protein; hence, no external excitation light source is needed. This type of fusion construct (i.e., bioluminescent fusion protein) also provides the advantage that the orange-red fluorescent protein within the fusion protein provides brighter light emissions than the luciferase catalyzed reaction, which improves reporter detection and the sensitivity of bioluminescence imaging.

A bioluminescent fusion protein will generally comprise at least one orange-red fluorescent protein, as described herein, connected to at least one luciferase, wherein the orange-red fluorescent protein is operably linked to the luciferase to allow bioluminescence resonance energy transfer (BRET) between the orange-red fluorescent protein, which serves as a fluorescent BRET acceptor and a luciferase reaction product, which serves as a bioluminescent BRET donor upon reaction of a chemiluminescent substrate at the active site of the luciferase. Such bioluminescent fusion proteins may be used for carrying out bioluminescence imaging in the presence of a chemiluminescent substrate that reacts to produce light.

In certain embodiments, the bioluminescent fusion protein comprises at least two orange-red fluorescent proteins, as described herein, connected to a luciferase, wherein a first orange-red fluorescent protein is connected to the N-terminus of the luciferase and a second orange-red fluorescent protein is connected to the C-terminus of the luciferase, wherein each orange-red fluorescent protein is operably linked to the luciferase to allow bioluminescence resonance energy transfer between the orange-red fluorescent protein, and the luciferase reaction product upon reaction of a chemiluminescent substrate at the active site of the luciferase. In one embodiment, the first or second orange-red fluorescent protein in the bioluminescent fusion protein comprises the amino acid sequence of SEQ ID NO:1 or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto, wherein the orange-red fluorescent protein emits light in response to absorption of cyan excitation light.

In certain embodiments, the bioluminescent fusion protein may further comprise a targeting sequence to increase the concentration of the bioluminescent fusion protein at a particular location in a cell.

Any luciferase capable of serving as a donor for bioluminescence resonance energy transfer to an orange-red fluorescent protein acceptor can be used to construct a bioluminescent fusion protein. Luciferase sequences from a number of species are well known in the art, such as, but not limited to, deep-sea shrimp *Oplophorus* luciferase, firefly luciferase, click beetle luciferase, *Renilla* luciferase, *Gaussia* luciferase, *Metridia* luciferase, *Vargula* luciferase, bacterial luciferase (e.g., *Vibrio fischeri, haweyi*, and *harveyi*), and dinoflagellate luciferase, any of which can be incorporated into a bioluminescent fusion protein. Representative luciferase sequences are shown in the National Center for Biotechnology Information (NCBI) database. See, for example, NCBI entries: Accession Nos. JQ437370, AFJ15586, AHH41349, AHH41346, HV216898, HV216897, Q9GV45, AB644228, M63501, AY015988, EF535511, AY015993, EU239244, AB371097, AB371096, EU025117, AB519703, AB674506, U89490, M25666, XM_003190150, XM_003602031, YP_004273613, YP_004216833, YP_003275551, KEP44836, YP_004213749, EFR93032, YP_206879, YP_206878, ABG26273, WP_005438583, WP_005384122, P07740, EF492542, AF085332, AF394060, AF394059, EU025117, AY364164, U03687, M65067; all of which sequences (as entered by the date of filing of this application) are herein incorporated by reference. Any of these sequences or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto, can be used to construct a bioluminescent fusion protein, or a nucleic acid encoding a bioluminescent fusion protein, as described herein.

In certain embodiments, the bioluminescent fusion protein comprises a luciferase derived from *Oplophorus gracihrostris*. Such bioluminescent fusion proteins can produce light from chemiluminescent substrates, including coelenterazine and coelenterazine analogs (see, e.g., U.S. Patent Application Publication No. 20120117667; herein incorporated by reference in its entirety).

In one embodiment, the bioluminescent fusion protein comprises NanoLuc luciferase, an engineered *Oplophorus gracilirostris* luciferase variant available from Promega Corporation (Madison, Wis.). NanoLuc luciferase is a 19.1 kDa, ATP-independent luciferase that utilizes the coelenterazine analog, furimazine, as a chemiluminescent substrate to produce high intensity luminescence. A representative amino acid sequence of NanoLuc luciferase is presented in SEQ ID NO:3. In one embodiment, a polypeptide comprising the sequence of SEQ ID NO:3 or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto, is used to construct a bioluminescent fusion protein, wherein the luciferase is capable of catalyzing a light-producing reaction with a chemiluminescent substrate that can be used for bioluminescence resonance energy transfer to an orange-red fluorescent protein acceptor.

An exemplary bioluminescent fusion protein, referred to as Antares (SEQ ID NO:2), is described in Example 1. Antares comprises a NanoLuc luciferase linked to two molecules of CyOFP, one at the N-terminus and the other at the C-terminus of the luciferase protein. In the presence of a chemiluminescent substrate, such as coelenterazine or a coelenterazine analog, such as furimazine, Antares emits bright orange light as a result of bioluminescence resonance energy transfer from a luciferase reaction product to each of the CyOFP fluorophores.

In addition, a bioluminescent fusion protein may comprise one or more domains that control the activity of the luciferase within the fusion protein, such that production of bioluminescence is dependent on interaction with a particular agent. For example, fusion proteins may comprise a domain that interacts with metal ions, small molecules (e.g., ATP, cAMP, cGMP, inositol triphosphate, diacylglycerol, histamine, or glucose), or macromolecules (e.g., proteins, nucleic acids, lipids, or carbohydrates), a protein-protein interaction domain, or a domain that recognizes specific modifications to a macromolecule (e.g., phosphorylation, lipidation, glycosylation, oxidation, proteolytic cleavage, or mutations), wherein luminescence is dependent on the domain interaction.

In another embodiment, the invention includes a bioluminescence resonance energy transfer (BRET) system comprising a bioluminescent fusion protein, as described herein, and a chemiluminescent substrate (e.g., coelenterazine, coelenterazine analog (e.g., furimazine), or other luciferase substrate). The BRET system may further comprise a photodetector or imaging device for detecting light emitted from the bioluminescent fusion protein, such as, but not limited to, an optical microscope, a digital microscope, a luminometer, a charged coupled device (CCD) image sensor, a complementary metal-oxide-semiconductor (CMOS) image sensor, or a digital camera.

B. Production of Orange-Red Fluorescent Proteins and Fusion Proteins

Orange-red fluorescent proteins and fusion proteins containing them, including bioluminescent fusion proteins, can be produced in any number of ways, all of which are well known in the art. In one embodiment, the orange-red fluorescent proteins and fusion proteins are generated using recombinant techniques. One of skill in the art can readily determine nucleotide sequences that encode the desired polypeptides using standard methodology and the teachings herein. Oligonucleotide probes can be devised based on the known sequences and used to probe genomic or cDNA libraries. The sequences can then be further isolated using standard techniques and, e.g., restriction enzymes employed to truncate the gene at desired portions of the full-length sequence. Similarly, sequences of interest can be isolated directly from cells and tissues containing the same, using known techniques, such as phenol extraction and the sequence further manipulated to produce the desired truncations. See, e.g., Sambrook et al., supra, for a description of techniques used to obtain and isolate DNA.

The sequences encoding polypeptides can also be produced synthetically, for example, based on the known sequences. The nucleotide sequence can be designed with the appropriate codons for the particular amino acid sequence desired. The complete sequence is generally assembled from overlapping oligonucleotides prepared by standard methods and assembled into a complete coding sequence. See, e.g., Edge (1981) *Nature* 292:756; Nambair et al. (1984) *Science* 223:1299; Jay et al. (1984) *J. Biol. Chem.* 259:6311; Stemmer et al. (1995) *Gene* 164:49-53.

Recombinant techniques are readily used to clone sequences encoding polypeptides useful in the claimed orange-red fluorescent proteins and fusion proteins that can then be mutagenized in vitro by the replacement of the appropriate base pair(s) to result in the codon for the desired amino acid. Such a change can include as little as one base pair, effecting a change in a single amino acid, or can encompass several base pair changes. Alternatively, the mutations can be effected using a mismatched primer that hybridizes to the parent nucleotide sequence (generally cDNA corresponding to the RNA sequence), at a temperature below the melting temperature of the mismatched duplex. The primer can be made specific by keeping primer length and base composition within relatively narrow limits and by keeping the mutant base centrally located. See, e.g., Innis et al, (1990) PCR Applications: Protocols for Functional Genomics; Zoller and Smith, *Methods Enzymol.* (1983) 100:468. Primer extension is effected using DNA polymerase, the product cloned and clones containing the mutated DNA, derived by segregation of the primer extended strand, selected. Selection can be accomplished using the mutant primer as a hybridization probe. The technique is also applicable for generating multiple point mutations. See, e.g., Dalbie-McFarland et al. *Proc. Natl. Acad. Sci USA* (1982) 79:6409.

Once coding sequences have been isolated and/or synthesized, they can be cloned into any suitable vector or replicon for expression. (See, also, Example 1). As will be apparent from the teachings herein, a wide variety of vectors encoding modified polypeptides can be generated by creating expression constructs which operably link, in various combinations, polynucleotides encoding polypeptides having deletions or mutations therein.

Numerous cloning vectors are known to those of skill in the art, and the selection of an appropriate cloning vector is a matter of choice. Examples of recombinant DNA vectors for cloning and host cells which they can transform include the bacteriophage λ (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV 14 (*E. coli* and *Bacillus subtilis*), pBD9 (*Bacillus*), pIJ61 (*Streptomyces*), pUC6 (*Streptomyces*), YIp5 (*Saccharomyces*), YCp19 (*Saccharomyces*) and bovine papilloma virus (mammalian cells). See, generally, DNA Cloning: Vols. I & II, supra; Sambrook et al., supra; B. Perbal, supra.

Insect cell expression systems, such as baculovirus systems, can also be used and are known to those of skill in the art and described in, e.g., Summers and Smith, *Texas Agricultural Experiment Station Bulletin No.* 1555 (1987). Materials and methods for baculovirus/insect cell expression systems are commercially available in kit form from, inter alia, Invitrogen, San Diego Calif. ("MaxBac" kit).

Plant expression systems can also be used to express the orange-red fluorescent proteins and bioluminescent fusion proteins described herein. Generally, such systems use virus-based vectors to transfect plant cells with heterologous genes. For a description of such systems, see, e.g., Porta et al., *Mol. Biotech.* (1996) 5:209-221; and Hackland et al., *Arch. Virol.* (1994) 139:1-22.

Viral systems, such as a vaccinia based infection/transfection system, as described in Tomei et al., *J. Virol.* (1993) 67:4017-4026 and Selby et al., *J. Gen. Virol.* (1993) 74:1103-1113, will also find use with the present invention. In this system, cells are first transfected in vitro with a vaccinia virus recombinant that encodes the bacteriophage T7 RNA polymerase. This polymerase displays exquisite specificity in that it only transcribes templates bearing T7 promoters. Following infection, cells are transfected with the DNA of interest, driven by a T7 promoter. The polymerase expressed in the cytoplasm from the vaccinia virus recombinant transcribes the transfected DNA into RNA that is then translated into protein by the host translational machinery. The method provides for high level, transient, cytoplasmic production of large quantities of RNA and its translation product(s).

The gene can be placed under the control of a promoter, ribosome binding site (for bacterial expression) and, optionally, an operator (collectively referred to herein as "control" elements), so that the DNA sequence encoding the desired polypeptide is transcribed into RNA in the host cell transformed by a vector containing this expression construction. The coding sequence may or may not contain a signal peptide or leader sequence. With the present invention, both the naturally occurring signal peptides and heterologous sequences can be used. Leader sequences can be removed by the host in post-translational processing. See, e.g., U.S. Pat. Nos. 4,431,739; 4,425,437; 4,338,397. Such sequences include, but are not limited to, the TPA leader, as well as the honey bee mellitin signal sequence.

Other regulatory sequences may also be desirable which allow for regulation of expression of the protein sequences relative to the growth of the host cell. Such regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

The control sequences and other regulatory sequences may be ligated to the coding sequence prior to insertion into a vector. Alternatively, the coding sequence can be cloned directly into an expression vector that already contains the control sequences and an appropriate restriction site.

In some cases it may be necessary to modify the coding sequence so that it may be attached to the control sequences with the appropriate orientation; i.e., to maintain the proper reading frame. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis, are well known to those skilled in the art. See, e.g., Sambrook et al., supra; *DNA Cloning*, Vols. I and II, supra; *Nucleic Acid Hybridization*, supra.

The expression vector is then used to transform an appropriate host cell. A number of mammalian cell lines are known in the art and include immortalized cell lines available from the American Type Culture Collection (ATCC), such as, but not limited to, Chinese hamster ovary (CHO) cells, HeLa cells, baby hamster kidney (BHK) cells, monkey kidney cells (COS), human hepatocellular carcinoma cells (e.g., Hep G2), Vero293 cells, as well as others. Similarly, bacterial hosts such as *E. coli, Bacillus subtilis*, and *Streptococcus* spp., will find use with the present expression constructs. Yeast hosts useful in the present invention include inter alia, *Saccharomyces cerevisiae, Candida albicans, Candida maltosa, Hansenula polymorpha, Kluyveromyces fragilis, Kluyveromyces lactis, Pichia guillerimondii, Pichia pastoris, Schizosaccharomyces pombe* and *Yarrowia lipolytica*. Insect cells for use with baculovirus expression vectors include, inter alia, *Aedes aegypti, Autographa californica, Bombyx mori, Drosophila melanogaster, Spodoptera frupperda*, and *Trichoplusia ni*.

Depending on the expression system and host selected, the red fluorescent proteins and fusion proteins of the present invention are produced by growing host cells transformed by an expression vector described above under conditions whereby the protein of interest is expressed. The selection of the appropriate growth conditions is within the skill of the art.

In one embodiment, the transformed cells secrete the polypeptide product into the surrounding media. Certain regulatory sequences can be included in the vector to enhance secretion of the protein product, for example using a tissue plasminogen activator (TPA) leader sequence, an interferon (γ or α) signal sequence or other signal peptide sequences from known secretory proteins. The secreted polypeptide product can then be isolated by various techniques described herein, for example, using standard purification techniques such as but not limited to, hydroxyapatite resins, column chromatography, ion-exchange chromatography, size-exclusion chromatography, electrophoresis, HPLC, immunoadsorbent techniques, affinity chromatography, immunoprecipitation, and the like.

Alternatively, the transformed cells are disrupted, using chemical, physical or mechanical means, which lyse the cells yet keep the recombinant polypeptides substantially intact. Intracellular proteins can also be obtained by removing components from the cell wall or membrane, e.g., by the use of detergents or organic solvents, such that leakage of the polypeptides occurs. Such methods are known to those of skill in the art and are described in, e.g., *Protein Purification Applications: A Practical Approach*, (Simon Roe, Ed., 2001).

For example, methods of disrupting cells for use with the present invention include but are not limited to: sonication or ultrasonication; agitation; liquid or solid extrusion; heat treatment; freeze-thaw; desiccation; explosive decompression; osmotic shock; treatment with lytic enzymes including proteases such as trypsin, neuraminidase and lysozyme; alkali treatment; and the use of detergents and solvents such as bile salts, sodium dodecylsulphate, Triton, NP40 and CHAPS. The particular technique used to disrupt the cells is largely a matter of choice and will depend on the cell type in which the polypeptide is expressed, culture conditions and any pre-treatment used.

Following disruption of the cells, cellular debris is removed, generally by centrifugation, and the intracellularly produced polypeptides are further purified, using standard purification techniques such as but not limited to, column chromatography, ion-exchange chromatography, size-exclusion chromatography, electrophoresis, HPLC, immunoadsorbent techniques, affinity chromatography, immunoprecipitation, and the like.

For example, one method for obtaining the intracellular polypeptides of the present invention involves affinity purification, such as by immunoaffinity chromatography using antibodies (e.g., previously generated antibodies), or by lectin affinity chromatography. Particularly preferred lectin resins are those that recognize mannose moieties such as but not limited to resins derived from *Galanthus nivalis* agglutinin (GNA), *Lens culinaris* agglutinin (LCA or lentil lectin), *Pisum sativum* agglutinin (PSA or pea lectin), *Narcissus pseudonarcissus* agglutinin (NPA) and *Allium ursinum* agglutinin (AUA). The choice of a suitable affinity resin is within the skill in the art. After affinity purification, the polypeptides can be further purified using conventional techniques well known in the art, such as by any of the techniques described above.

Polypeptides can be conveniently synthesized chemically, for example by any of several techniques that are known to those skilled in the peptide art. In general, these methods employ the sequential addition of one or more amino acids to a growing peptide chain. Normally, either the amino or carboxyl group of the first amino acid is protected by a suitable protecting group. The protected or derivatized amino acid can then be either attached to an inert solid support or utilized in solution by adding the next amino acid in the sequence having the complementary (amino or carboxyl) group suitably protected, under conditions that allow for the formation of an amide linkage. The protecting group is then removed from the newly added amino acid residue and the next amino acid (suitably protected) is then added, and so forth. After the desired amino acids have been linked in the proper sequence, any remaining protecting groups (and any solid support, if solid phase synthesis techniques are used) are removed sequentially or concurrently, to render the final polypeptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide. See, e.g., J. M. Stewart and J. D. Young, *Solid Phase Peptide Synthesis* (Pierce Chemical Co., Rockford, Ill. 1984) and G. Barany and R. B. Merrifield, *The Peptides: Analysis, Synthesis, Biology*, editors E. Gross and J. Meienhofer, Vol. 2, (Academic Press, New York, 1980), pp. 3-254, for solid phase peptide synthesis techniques; and M. Bodansky, *Principles of Peptide Synthesis*, (Springer-Verlag, Berlin 1984) and E. Gross and J. Meienhofer, Eds., *The Peptides: Analysis, Synthesis, Biology*, Vol. 1, for classical solution synthesis. These methods are typically used for relatively small polypeptides, i.e., up to about 50-100 amino acids in length, but are also applicable to larger polypeptides.

Typical protecting groups include t-butyloxycarbonyl (Boc), 9-fluorenylmethoxycarbonyl (Fmoc) benzyloxycarbonyl (Cbz); p-toluenesulfonyl (Tx); 2,4-dinitrophenyl; benzyl (Bzl); biphenylisopropyloxycarboxy-carbonyl, t-amyloxycarbonyl, isobornyloxycarbonyl, o-bromobenzyloxycarbonyl, cyclohexyl, isopropyl, acetyl, o-nitrophenylsulfonyl and the like.

Typical solid supports are cross-linked polymeric supports. These can include divinylbenzene cross-linked-styrene-based polymers, for example, divinylbenzene-hydroxymethylstyrene copolymers, divinylbenzene-chloromethylstyrene copolymers and divinylbenzene-benzhydrylaminopolystyrene copolymers.

Polypeptide analogs can also be chemically prepared by other methods such as by the method of simultaneous multiple peptide synthesis. See, e.g., Houghten *Proc. Natl. Acad. Sci. USA* (1985) 82:5131-5135; U.S. Pat. No. 4,631, 211.

C. Nucleic Acids Encoding Orange-Red Fluorescent Proteins and Bioluminescent Fusion Proteins Nucleic acids encoding orange-red fluorescent proteins and bioluminescent fusion proteins can be used, for example, to produce the orange-red fluorescent proteins and bioluminescent fusion proteins within a cell for various purposes (e.g., reporter gene assays, live cell imaging). Nucleic acids described herein can be inserted into an expression vector to create an expression cassette capable of producing an orange-red fluorescent protein or bioluminescent fusion protein in a suitable host cell. The ability of constructs to produce orange-red fluorescent proteins or bioluminescent fusion proteins can be empirically determined by detecting fluorescent or bioluminescent emissions as described, for example, in Example 1.

Expression cassettes typically include control elements operably linked to the coding sequence, which allow for the expression of the gene in vivo in the subject species. For example, typical promoters for mammalian cell expression include the SV40 early promoter, a CMV promoter such as the CMV immediate early promoter, the mouse mammary tumor virus LTR promoter, the adenovirus major late promoter (Ad MLP), and the herpes simplex virus promoter, among others. Other nonviral promoters, such as a promoter derived from the murine metallothionein gene, will also find use for mammalian expression. Typically, transcription termination and polyadenylation sequences will also be present, located 3' to the translation stop codon. Preferably, a sequence for optimization of initiation of translation, located 5' to the coding sequence, is also present. Examples of transcription terminator/polyadenylation signals include those derived from SV40, as described in Sambrook et al., supra, as well as a bovine growth hormone terminator sequence.

Enhancer elements may also be used herein to increase expression levels of the mammalian constructs. Examples include the SV40 early gene enhancer, as described in Dijkema et al., EMPO J. (1985) 4:761, the enhancer/promoter derived from the long terminal repeat (LTR) of the Rous Sarcoma Virus, as described in Gorman et al., Proc. Natl. Acad. Sci. USA (1982b) 79:6777 and elements derived from human CMV, as described in Boshart et al., Cell (1985) 41:521, such as elements included in the CMV intron A sequence.

Targeting sequences may be used to direct localization of an orange-red fluorescent protein or fusion protein to a specific tissue, cell-type (e.g. muscle, heart, or neural cell), cellular compartment (e.g., mitochondria or other organelle, nucleus, cytoplasm, or plasma membrane), or protein. For example, constructs may include a polynucleotide sequence encoding a secretory protein signal sequence, a membrane protein signal sequence, a nuclear localization sequence, a nucleolar localization signal sequence, an endoplasmic reticulum localization sequence, a peroxisome localization sequence, a mitochondrial localization sequence, or a protein-protein interaction motif sequence. See, e.g., *Protein Targeting, Transport, and Translocation* (R. Dalbey and Gunnar von Heijne eds., Academic Press, 2002); *Protein Targeting Protocols* (Methods in Molecular Biology, R. A. Clegg ed., Humana Press, 1998); *Protein Engineering and Design* (S. J. Park J. R. Cochran eds., CRC Press, 2009); *Protein—Protein Interactions: Methods and Applications* (Methods in Molecular Biology, H. Fu ed., Humana Press, 2004); Emanuelsson et al. (2001) Biochim. Biophys. Acta 1541(1-2):114-119; Hurley et al. (2000) Annu. Rev. Biophys. Biomol. Struct. 29:49-79; Jans et al. (2000) Bioessays 22(6):532-544; Christophe et al. (2000) Cell Signal. 12(5):337-341; Stanley (1996) Mol. Membr. Biol. 13(1):19-27; Cosson et al. (1995) Cold Spring Harb. Symp. Quant. Biol. 60:113-117; Emmott et al. (2009) EMBO Rep. 10(3):231-238; Gurkan et al. (2007) Adv. Exp. Med. Biol. 607:73-83; Romanelli et al. (2008) J. Neurochem. 105(6):2055-2068; Terlecky et al. (2007) Adv. Drug Deliv. Rev. 59(8):739-747; Arnoys et al. (2007) Acta Histochem. 109(2):89-110; Brown et al. (2000) Kidney Int. 57(3):816-824; Jadwin et al. (2012) FEBS Lett. 586(17):2586-2596; Liu et al. (2012) FEBS Lett. 586(17):2597-2605; Romero et al. (2011) Adv. Pharmacol. 62:279-314; Obenauer et al. (2004) Methods Mol. Biol. 261:445-468; herein incorporated by reference.

Once complete, constructs encoding orange-red fluorescent proteins or fusion proteins can be used to transfect cells in culture or be administered to a subject using standard gene delivery protocols. Genes can be delivered either directly to a subject or, alternatively, delivered ex vivo, to cells derived from the subject and the cells reimplanted in the subject. Methods for gene delivery are known in the art. See, e.g., U.S. Pat. Nos. 5,399,346, 5,580,859, and 5,589,466.

A number of viral based systems have been developed for gene transfer into mammalian cells. These include adenoviruses, retroviruses (γ-retroviruses and lentiviruses), poxviruses, adeno-associated viruses, baculoviruses, and herpes simplex viruses (see e.g., Warnock et al. (2011) Methods Mol. Biol. 737:1-25; Walther et al. (2000) Drugs 60(2):249-271; and Lundstrom (2003) Trends Biotechnol. 21(3):117-122; herein incorporated by reference).

For example, retroviruses provide a convenient platform for gene delivery systems. Selected sequences can be inserted into a vector and packaged in retroviral particles using techniques known in the art. The recombinant virus can then be isolated and delivered to cells of the subject either in vivo or ex vivo. A number of retroviral systems have been described (U.S. Pat. No. 5,219,740; Miller and Rosman (1989) BioTechniques 7:980-990; Miller, A. D. (1990) Human Gene Therapy 1:5-14; Scarpa et al. (1991) Virology 180:849-852; Burns et al. (1993) Proc. Natl. Acad. Sci. USA 90:8033-8037; Boris-Lawrie and Temin (1993) Cur. Opin. Genet. Develop. 3:102-109; and Ferry et al. (2011) Curr Pharm Des. 17(24):2516-2527). Lentiviruses are a class of retroviruses that are particularly useful for delivering polynucleotides to mammalian cells because they are able to infect both dividing and nondividing cells (see e.g., Lois et al (2002) Science 295:868-872; Durand et al. (2011) Viruses 3(2):132-159; herein incorporated by reference).

A number of adenovirus vectors have also been described. Unlike retroviruses which integrate into the host genome, adenoviruses persist extrachromosomally thus minimizing the risks associated with insertional mutagenesis (Haj-Ahmad and Graham, J. Virol. (1986) 57:267-274; Bett et al., J. Virol. (1993) 67:5911-5921; Mittereder et al., Human Gene Therapy (1994) 5:717-729; Seth et al., J. Virol. (1994) 68:933-940; Barr et al., Gene Therapy (1994) 1:51-58; Berkner, K. L. BioTechniques (1988) 6:616-629; and Rich et al., Human Gene Therapy (1993) 4:461-476). Additionally, various adeno-associated virus (AAV) vector systems have been developed for gene delivery. AAV vectors can be readily constructed using techniques well known in the art. See, e.g., U.S. Pat. Nos. 5,173,414 and 5,139,941; International Publication Nos. WO 92/01070 (published 23 Jan. 1992) and WO 93/03769 (published 4 Mar. 1993); Lebkowski et al., Molec. Cell Biol. (1988) 8:3988-3996; Vincent et al., Vaccines 90 (1990) (Cold Spring Harbor Laboratory Press); Carter, B. J. Current Opinion in Biotechnology (1992) 3:533-539; Muzyczka, N. Current Topics in Microbiol. Immunol. (1992) 158:97-129; Kotin, R. M. Human Gene Therapy (1994) 5:793-801; Shelling and Smith, Gene Therapy (1994) 1:165-169; and Zhou et al., J. Exp. Med. (1994) 179:1867-1875.

Another vector system useful for delivering the polynucleotides of the present invention is the enterically administered recombinant poxvirus vaccines described by Small, Jr., P. A., et al. (U.S. Pat. No. 5,676,950, issued Oct. 14, 1997, herein incorporated by reference).

Additional viral vectors which will find use for delivering the nucleic acid molecules encoding the orange-red fluorescent proteins and bioluminescent fusion proteins include those derived from the pox family of viruses, including vaccinia virus and avian poxvirus. By way of example, vaccinia virus recombinants expressing the orange-red fluorescent proteins and bioluminescent fusion proteins can be constructed as follows. The DNA encoding the particular the orange-red fluorescent protein or fusion protein coding sequence is first inserted into an appropriate vector so that it is adjacent to a vaccinia promoter and flanking vaccinia DNA sequences, such as the sequence encoding thymidine kinase (TK). This vector is then used to transfect cells which are simultaneously infected with vaccinia. Homologous recombination serves to insert the vaccinia promoter plus the gene encoding the coding sequences of interest into the viral genome. The resulting TK-recombinant can be selected by culturing the cells in the presence of 5-bromodeoxyuridine and picking viral plaques resistant thereto.

Alternatively, avipoxviruses, such as the fowlpox and canarypox viruses, can also be used to deliver the genes. Recombinant avipox viruses, expressing immunogens from mammalian pathogens, are known to confer protective immunity when administered to non-avian species. The use of an avipox vector is particularly desirable in human and other mammalian species since members of the avipox genus can only productively replicate in susceptible avian species and therefore are not infective in mammalian cells. Methods for producing recombinant avipoxviruses are known in the art and employ genetic recombination, as described above with respect to the production of vaccinia viruses. See, e.g., WO 91/12882; WO 89/03429; and WO 92/03545.

Molecular conjugate vectors, such as the adenovirus chimeric vectors described in Michael et al., J. Biol. Chem. (1993) 268:6866-6869 and Wagner et al., Proc. Natl. Acad. Sci. USA (1992) 89:6099-6103, can also be used for gene delivery.

Members of the Alphavirus genus, such as, but not limited to, vectors derived from the Sindbis virus (SIN), Semliki Forest virus (SFV), and Venezuelan Equine Encephalitis virus (VEE), will also find use as viral vectors for delivering the polynucleotides of the present invention. For a description of Sindbis-virus derived vectors useful for the practice of the instant methods, see, Dubensky et al. (1996) J. Virol. 70:508-519; and International Publication Nos. WO 95/07995, WO 96/17072; as well as, Dubensky, Jr., T. W., et al., U.S. Pat. No. 5,843,723, issued Dec. 1, 1998, and Dubensky, Jr., T. W., U.S. Pat. No. 5,789,245, issued Aug. 4, 1998, both herein incorporated by reference. Particularly preferred are chimeric alphavirus vectors comprised of sequences derived from Sindbis virus and Venezuelan equine encephalitis virus. See, e.g., Perri et al. (2003) J. Virol. 77: 10394-10403 and International Publication Nos. WO 02/099035, WO 02/080982, WO 01/81609, and WO 00/61772; herein incorporated by reference in their entireties.

A vaccinia based infection/transfection system can be conveniently used to provide for inducible, transient expression of the coding sequences of interest (for example, an orange-red fluorescent protein or bioluminescent fusion protein expression cassette) in a host cell. In this system, cells are first infected in vitro with a vaccinia virus recombinant that encodes the bacteriophage T7 RNA polymerase. This polymerase displays exquisite specificity in that it only transcribes templates bearing T7 promoters. Following infection, cells are transfected with the polynucleotide of interest, driven by a T7 promoter. The polymerase expressed in the cytoplasm from the vaccinia virus recombinant transcribes the transfected DNA into RNA which is then translated into protein by the host translational machinery. The method provides for high level, transient, cytoplasmic production of large quantities of RNA and its translation products. See, e.g., Elroy-Stein and Moss, Proc. Natl. Acad. Sci. USA (1990) 87:6743-6747; Fuerst et al., Proc. Natl. Acad. Sci. USA (1986) 83:8122-8126.

As an alternative approach to infection with vaccinia or avipox virus recombinants, or to the delivery of genes using other viral vectors, an amplification system can be used that will lead to high level expression following introduction into host cells. Specifically, a T7 RNA polymerase promoter preceding the coding region for T7 RNA polymerase can be engineered. Translation of RNA derived from this template will generate T7 RNA polymerase which in turn will transcribe more template. Concomitantly, there will be a cDNA whose expression is under the control of the T7 promoter. Thus, some of the T7 RNA polymerase generated from translation of the amplification template RNA will lead to transcription of the desired gene. Because some T7 RNA polymerase is required to initiate the amplification, T7 RNA polymerase can be introduced into cells along with the template(s) to prime the transcription reaction. The polymerase can be introduced as a protein or on a plasmid encoding the RNA polymerase. For a further discussion of T7 systems and their use for transforming cells, see, e.g., International Publication No. WO 94/26911; Studier and Moffatt, J. Mol. Biol. (1986) 189:113-130; Deng and Wolff, Gene (1994) 143:245-249; Gao et al., Biochem. Biophys. Res. Commun. (1994) 200:1201-1206; Gao and Huang, Nuc. Acids Res. (1993) 21:2867-2872; Chen et al., Nuc. Acids Res. (1994) 22:2114-2120; and U.S. Pat. No. 5,135, 855.

The synthetic expression cassette of interest can also be delivered without a viral vector. For example, the synthetic expression cassette can be packaged as DNA or RNA in liposomes prior to delivery to the subject or to cells derived therefrom. Lipid encapsulation is generally accomplished using liposomes which are able to stably bind or entrap and retain nucleic acid. The ratio of condensed DNA to lipid preparation can vary but will generally be around 1:1 (mg DNA:micromoles lipid), or more of lipid. For a review of the use of liposomes as carriers for delivery of nucleic acids, see, Hug and Sleight, Biochim. Biophys. Acta. (1991.) 1097:1-17; Straubinger et al., in Methods of Enzymology (1983), Vol. 101, pp. 512-527.

Liposomal preparations for use in the present invention include cationic (positively charged), anionic (negatively charged) and neutral preparations, with cationic liposomes particularly preferred. Cationic liposomes have been shown to mediate intracellular delivery of plasmid DNA (Felgner et al., Proc. Natl. Acad. Sci. USA (1987) 84:7413-7416); mRNA (Malone et al., Proc. Natl. Acad. Sci. USA (1989) 86:6077-6081); and purified transcription factors (Debs et al., J. Biol. Chem. (1990) 265:10189-10192), in functional form.

Cationic liposomes are readily available. For example, N[1-2,3-dioleyloxy)propyl]-N,N,N-triethylammonium (DOTMA) liposomes are available under the trademark Lipofectin, from GIBCO BRL, Grand Island, N.Y. (See, also, Felgner et al., Proc. Natl. Acad. Sci. USA (1987) 84:7413-7416). Other commercially available lipids include (DDAB/DOPE) and DOTAP/DOPE (Boerhinger). Other cationic liposomes can be prepared from readily available materials using techniques well known in the art. See, e.g., Szoka et al., Proc. Natl. Acad. Sci. USA (1978) 75:4194-4198; PCT Publication No. WO 90/11092 for a description of the synthesis of DOTAP (1,2-bis(oleoyloxy)-3-(trimethylammonio)propane) liposomes.

Similarly, anionic and neutral liposomes are readily available, such as, from Avanti Polar Lipids (Birmingham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

The liposomes can comprise multilammelar vesicles (MLVs), small unilamellar vesicles (SUVs), or large unilamellar vesicles (LUVs). The various liposome-nucleic acid complexes are prepared using methods known in the art. See, e.g., Straubinger et al., in METHODS OF IMMUNOLOGY (1983), Vol. 101, pp. 512-527; Szoka et al., Proc. Natl. Acad. Sci. USA (1978) 75:4194-4198; Papahadjopoulos et al., Biochim. Biophys. Acta (1975) 394:483; Wilson et al., Cell (1979) 17:77); Deamer and Bangham, Biochim. Biophys. Acta (1976) 443:629; Ostro et al., Biochem. Biophys. Res. Commun. (1977) 76:836; Fraley et al., Proc. Natl. Acad. Sci. USA (1979) 76:3348); Enoch and Strittmatter, Proc. Natl. Acad. Sci. USA (1979) 76:145); Fraley et al., J. Biol. Chem. (1980) 255:10431; Szoka and Papahadjopoulos, Proc. Natl. Acad. Sci. USA (1978) 75:145; and Schaefer-Ridder et al., Science (1982) 215:166.

The DNA and/or peptide(s) can also be delivered in cochleate lipid compositions similar to those described by Papahadjopoulos et al., Biochem. Biophys. Acta (1975) 394:483-491. See, also, U.S. Pat. Nos. 4,663,161 and 4,871,488.

The expression cassette of interest may also be encapsulated, adsorbed to, or associated with, particulate carriers. Examples of particulate carriers include those derived from polymethyl methacrylate polymers, as well as microparticles derived from poly(lactides) and poly(lactide-co-glycolides), known as PLG. See, e.g., Jeffery et al., Pharm. Res. (1993) 10:362-368; McGee J. P., et al., J Microencapsul. 14(2):197-210, 1997; O'Hagan D. T., et al., Vaccine 11(2):149-54, 1993.

Furthermore, other particulate systems and polymers can be used for the in vivo or ex vivo delivery of the nucleic acid of interest. For example, polymers such as polylysine, polyarginine, polyornithine, spermine, spermidine, as well as conjugates of these molecules, are useful for transferring a nucleic acid of interest. Similarly, DEAE dextran-mediated transfection, calcium phosphate precipitation or precipitation using other insoluble inorganic salts, such as strontium phosphate, aluminum silicates including bentonite and kaolin, chromic oxide, magnesium silicate, talc, and the like, will find use with the present methods. See, e.g., Felgner, P. L., Advanced Drug Delivery Reviews (1990) 5:163-187, for a review of delivery systems useful for gene transfer. Peptoids (Zuckerman, R. N., et al., U.S. Pat. No. 5,831,005, issued Nov. 3, 1998, herein incorporated by reference) may also be used for delivery of a construct of the present invention.

Additionally, biolistic delivery systems employing particulate carriers such as gold and tungsten are especially useful for delivering synthetic expression cassettes of the present invention. The particles are coated with the synthetic expression cassette(s) to be delivered and accelerated to high velocity, generally under a reduced atmosphere, using a gun powder discharge from a "gene gun." For a description of such techniques, and apparatuses useful therefore, see, e.g., U.S. Pat. Nos. 4,945,050; 5,036,006; 5,100,792; 5,179,022; 5,371,015; and 5,478,744. Also, needle-less injection systems can be used (Davis, H. L., et al, Vaccine 12:1503-1509, 1994; Bioject, Inc., Portland, Oreg.).

Recombinant vectors carrying a synthetic expression cassette of the present invention are formulated into compositions for delivery to a cell or subject.

The compositions will generally include one or more physiologically acceptable excipients or vehicles such as water, saline, glycerol, polyethyleneglycol, hyaluronic acid, ethanol, etc. Additionally, auxiliary substances, such as wetting or emulsifying agents, pH buffering substances, surfactants and the like, may be present in such vehicles. Certain facilitators of nucleic acid uptake and/or expression can also be included in the compositions or coadministered.

Once formulated, the compositions of the invention can be administered directly to a subject (e.g., as described above) or, alternatively, delivered ex vivo, to cells derived from the subject, using methods such as those described above. For example, methods for the ex vivo delivery and reimplantation of transformed cells into a subject are known in the art and can include, e.g., dextran-mediated transfection, calcium phosphate precipitation, polybrene mediated transfection, lipofectamine and LT-1 mediated transfection, protoplast fusion, electroporation, encapsulation of the polynucleotide(s) in liposomes, and direct microinjection of the DNA into nuclei.

Direct delivery of synthetic expression cassette compositions in vivo will generally be accomplished with or without viral vectors, as described above, by injection using either a conventional syringe, needless devices such as Bioject™ or a gene gun, such as the Accell™ gene delivery system (PowderMed Ltd, Oxford, England).

D. Applications

The orange-red fluorescent proteins and bioluminescent fusion proteins of the invention can be used as labels or reporters in many fluorescent or bioluminescent assays and should find numerous applications in basic research and development. For example, fluorescence and bioluminescence emitted from orange-red fluorescent proteins and bioluminescent fusion proteins can be used for labeling cells and molecules and imaging of cells and tissue using methods well-known in the art. See, e.g., S. S. Gambhir and S. S. Yaghoubi *Molecular Imaging with Reporter Genes* (Cambridge Molecular Imaging Series, Cambridge University Press, 2010); *Imaging Cellular and Molecular Biological Functions* (S. L. Shorte and F. Frischknecht eds., Springer, 2007); P. P. Mondal and A. Diaspro *Fundamentals of Fluorescence Microscopy* (Springer Netherlands, 2013); L. Brovko *Bioluminescence and Fluorescence for In Vivo Imaging* (SPIE Press, 2010); J. R. Lakowicz *Principles of Fluorescence Spectroscopy* (Springer; $3^{rd}$ edition, 2011); *Bioluminescence: Methods and Protocols* (Methods in Molecular Biology, P. B. Rich, C. Douillet eds., Humana Press, $2^{nd}$ edition, 2009); R. Yuste *Imaging: A Laboratory Manual* (Cold Spring Harbor Laboratory Press, 2010); herein incorporated by reference in their entireties.

Fluorescence or bioluminescence images may be recorded by any suitable method. For example, a CCD image sensor (e.g., intensified CCD (ICCD) or electron multiplying CCD (EMCCD)), a CMOS image sensor, or a digital camera may be used to capture images. The image may be a still photo or a video in any format (e.g., bitmap, Graphics Interchange Format, JPEG file interchange format, TIFF, or mpeg). Alternatively, images may be captured by an analog camera and converted into an electronic form. In addition, luminescence can be detected by a luminometer, and fluorescence can be detected by a fluorimeter, a fluorescence microscope, a fluorescence microplate reader, a fluorometric imaging plate reader, fluorescence-activated cell sorting, a fiber-optic fluorescence imaging system, or a medical fluorescence imaging device (e.g., a handheld fluorescence microscope, a laparoscope, an endoscope, or a microendoscope).

Imaging can be performed in vivo, ex vivo, or in vitro for various purposes. In certain embodiments, an orange-red fluorescent protein or bioluminescent fusion protein of the invention is used in imaging of gene expression (e.g., imaging with reporter genes for monitoring endogenous gene expression or transgene expression, regulation of gene expression, or gene therapy), fluorescent or bioluminescent labeling of cells (e.g., quantitating cells, tracking particular cells, monitoring cell movement or cell proliferation), fluorescent or bioluminescent labeling of biological molecules of interest, for example, for studying biomolecular mechanisms and dynamics (e.g., single molecule tracking, imaging protein-protein interactions, imaging cell trafficking, or imaging stem cell differentiation), or live cell imaging (e.g., imaging an infection, a tumor, or immune activation).

Orange-red fluorescent proteins or bioluminescent fusion proteins can also be used to label or image any cell. The cell can be of any cell type including, but not limited to, epithelial, endothelial, neuronal, adipose, cardiac, skeletal muscle, smooth muscle, fibroblast, immune cells, hepatic, splenic, lung, circulating blood cells, reproductive cells, gastrointestinal, renal, bone marrow, and pancreatic cells. The cell can be from a cell line, a stem cell, or a primary cell isolated from any tissue including, but not limited to heart, liver, lung, gut, stomach, fat, muscle, nervous system, testes, uterus, ovary, skin, spleen, endocrine organ, and bone, etc. Where the cell is maintained under in vitro conditions, conventional tissue culture conditions and methods can be used, and are known to those of skill in the art. Isolation and culture methods for various cells are well within the knowledge of one skilled in the art. The cell can be a prokaryotic cell, a eukaryotic cell, a mammalian cell, or a human cell.

Imaging with the orange-red fluorescent proteins or bioluminescent fusion proteins of the invention, which emit orange-red light, has the advantage that orange-red light penetrates several millimeters to centimeters into living tissues and can be used to visualize tissue below the surface. Because tissue exhibits almost no autofluorescence in this region of the spectrum, interfering background fluorescence is minimal.

Moreover, imaging with the orange-red fluorescent proteins and bioluminescent fusion proteins, described herein, is generally applicable for any disease, disorder, or pathology. For example, cells or tissues of interest can be contacted with an orange-red fluorescent protein or bioluminescent fusion protein. If an orange-red fluorescent protein is used, the cells or tissue are illuminated with light at a fluorescence excitation wavelength of the orange-red fluorescent protein. Excitation light sources that can be used include arc lamps and lasers, laser diodes and other light emitting diode sources, and both single and multiple photon excitation sources. A fluorescence image of the cells or tissue can be recorded using a medical fluorescence imaging device capable of detecting the fluorescence emitted by the orange-red fluorescent protein. Alternatively, a bioluminescent fusion protein can be used, which has the advantage of not requiring excitation light. Instead, a chemiluminescent substrate is administered, which undergoes a luciferase-catalyzed reaction to produce light that can be detected by an imaging device.

Additionally, multi-reporter imaging of cells can be performed using combinations of one or more orange-red fluorescent proteins and/or bioluminescent fusion proteins, described herein, and/or other fluorophores, bioluminescent proteins, or other chromophores that emit light at different wavelengths to allow different components of a cell to be distinguished in recorded images. When different fluorophores are used, preferably, all fluorophores can be excited at the same wavelength. For example, imaging can be performed with an orange-red fluorescent protein and a green fluorescent protein that produce fluorescence by excitation at the same wavelength, but emit fluorescence at different wavelengths. In another example, imaging is performed with a bioluminescent fusion protein and a fluorescent protein that emit light at different wavelengths. A chemiluminescent substrate is introduced into the cell before illumination with light at an excitation wavelength of the fluorescent protein to allow simultaneous detection of fluorescence emitted by the fluorescent protein and bioluminescence emitted by the bioluminescent fusion protein.

Preferably, a detectably effective amount of an orange-red fluorescent protein or bioluminescent fusion protein is administered to a subject; that is, an amount that is sufficient to yield an acceptable image using the fluorescence or bioluminescence imaging equipment that is available for clinical use. A detectably effective amount of the orange-red fluorescent protein or bioluminescent fusion protein may be administered in more than one injection if needed. The detectably effective amount of the orange-red fluorescent protein or bioluminescent fusion protein needed for an individual may vary according to factors such as the degree of susceptibility to uptake into the target area of interest, the age, sex, and weight of the individual, and the particular medical imaging device used. Optimization of such factors is within the level of skill in the art.

Fluorescence or bioluminescence imaging with orange-red fluorescent proteins or bioluminescent fusion proteins can be used in assessing efficacy of therapeutic drugs in treating a disease or disorder. For example, images can be acquired after treatment to determine if the individual is responding to treatment.

For example, in a subject with cancer, fluorescence or bioluminescence imaging with an orange-red fluorescent protein or bioluminescent fusion protein, respectively, can be used to evaluate whether a tumor is shrinking or growing. Further, the extent of cancerous disease (stage of cancer progression) can be determined to aid in determining prognosis and evaluating optimal strategies for treatment (e.g., surgery, radiation, or chemotherapy). In another example, fluorescence or bioluminescence imaging can be used to monitor an infection in a subject, for example, to evaluate whether a treatment is effective in eradicating an infection or if the infection is spreading.

Additionally, orange-red fluorescent proteins and bioluminescent fusion proteins can be used in image-guided surgery. For example, fluorescence and bioluminescence imaging according to the methods of the invention can be used, for example, for detection of pathology, tumor margin delineation, evaluation of the completeness of resection, visualization of critical structures, visualization of nerves, vascular imaging, sentinel lymph node mapping, and evaluation of the efficacy of treatment.

Various medical imaging systems have been developed for open surgery as well as for laparoscopic, thoracoscopic, and robot-assisted surgery and can be used in the practice of the invention. Conventional laparoscopes and endoscopes can be equipped with a photodetector (e.g., camera or CCD detector) to provide guidance during medical procedures. Fiber-optic imaging systems can also be used, which include portable handheld microscopes, flexible endoscopes, and microendoscopes. An illumination source can be added to such devices to allow fluorescence imaging. For fluorescence imaging, the excitation light source and photodetector can be integrated into a single medical imaging device or the excitation light source and/or photodetector may reside apart, in which case, imaging is performed with remote delivery of excitation light. Miniaturized imaging systems can be used that allow imaging inside small cavities and constricted spaces. In addition, miniaturized imaging devices (e.g., microendoscopes) may be implanted within a subject for long-term imaging studies. An imaging system that can simultaneously detect fluorescence or bioluminescence at multiple wavelengths can be used for detection of multiple fluorescent and/or bioluminescent agents that emit light at different wavelengths. In addition, a camera may be used to take both photographic images of a subject and to detect fluorescence and bioluminescence, so that photographic images and fluorescent or bioluminescent images can be superimposed to allow regions of fluorescence or bioluminescence to be mapped to the subject's anatomy for identification of the source of light emissions. For a review of medical imaging devices and methods of using them in image-guided surgery and other medical procedures, see, e.g., Gray et al. (2012) Biomed. Opt. Express. 3(8):1880-1890; Flusberg et al. (2005) Nat. Methods 2(12):941-950; Choyke et al. (2012) IEEE J. Sel. Top. Quantum. Electron. 18(3):1140-1146; Gray et al. (2012) Proc. SPIE February 3: 8207; Vahrmeijer et al. (2013) Nat. Rev. Clin. Oncol. 10:507-518; Braks et al. (2013) Methods Mol. Biol. 923: 353-368; Yong et al. (2011) Diabetes 60(5):1383-1392; Wilson et al. (2008) J. Vis. Exp. May 2(14) pii: 740; Engelsman et al. (2009) J. Biomed. Mater. Res B Appl Biomater. 88(1):123-129; Franke-Fayard et al. (2006) Nat. Protoc. 1(1):476-485; Rehemtulla et al. (2000) Neoplasia. 2(6):491-495; and Close et al. (2011) Sensors 11:180-206; herein incorporated by reference in their entireties.

E. Kits

Orange-red fluorescent proteins and fusion proteins comprising them (e.g., bioluminescent fusion proteins) or nucleic acids encoding them can be provided in kits with suitable instructions and other necessary reagents for preparing or using them as described above. The kit may contain in separate containers an orange-red fluorescent protein or bioluminescent fusion protein, or recombinant constructs for producing an orange-red fluorescent proteins or bioluminescent fusion protein, and/or cells (either already transfected or separate). Additionally, instructions (e.g., written, tape, VCR, CD-ROM, DVD, flash drive, SD card, etc.) for using an orange-red fluorescent protein or bioluminescent fusion protein, for example, as a reporter for labeling or imaging may be included in the kit. The kit may also contain other packaged reagents and materials (e.g., transfection reagents, buffers, media, and the like).

Orange-red fluorescent proteins or bioluminescent fusion proteins can be used as labels or reporters in many fluorescent or bioluminescent assays or medical imaging, as discussed above. Therefore, kits may also include reagents for performing such assays or medical imaging. In certain embodiments, the kit further includes a chemiluminescent substrate, a BRET system, or a reporter gene construct utilizing an orange-red fluorescent protein or bioluminescent fusion protein, as described herein.

In certain embodiments, the kit comprises an orange-red fluorescent protein comprising the amino acid sequence of SEQ ID NO:1 or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto, wherein the orange-red fluorescent protein emits orange-red light in response to absorption of cyan excitation light; or a recombinant construct for producing such an orange-red fluorescent protein.

In one embodiment, the orange-red fluorescent protein comprises a variant polypeptide, wherein the amino acid corresponding to His 61 numbered relative to the reference sequence of SEQ ID NO:1 is replaced with a methionine.

In other embodiments, the kit comprises a bioluminescent fusion protein comprising an amino acid sequence selected from the group consisting of SEQ ID NO:2 and SEQ ID NO:4, or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto, wherein the fusion protein emits orange-red light in response to exposure to a chemiluminescent substrate; or a recombinant construct for producing such a bioluminescent fusion protein.

III. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Example 1

A Bright Cyan-Excitable Orange Fluorescent Protein Enables Dual-Emission Microscopy and Highly Sensitive Bioluminescence Imaging In Vivo Introduction Orange-red fluorescent proteins (FPs) are widely used in biomedical research for multiplexed epifluorescence microscopy with GFP-based probes, but the different excitation requirements of orange-red FPs and GFPs make multiplexing with new advanced microscopy methods difficult. Separately, orange-red FPs are useful for deep-tissue imaging in mammals due to the relative tissue transmissibility of orange-red light, but their dependence on illumination limits their sensitivity as reporters in deep tissues. Here we describe CyOFP, an engineered orange-red FP that is exceptionally bright and excitable by cyan light. We show that CyOFP enables single-excitation multiplexed imaging with GFP-based probes in single-photon and two-photon microscopy, including time-lapse imaging in light-sheet systems. CyOFP also serves as an efficient acceptor for resonance energy transfer from the highly catalytic blue-emitting luciferase NanoLuc. An optimized fusion of CyOFP and NanoLuc functions as a highly sensitive bioluminescent reporter in vivo, producing 18 times more emission in mice than firefly luciferase.

Results

Development of a Bright Cyan-Excitable Orange Fluorescent Protein, CyOFP

Figure 6A:
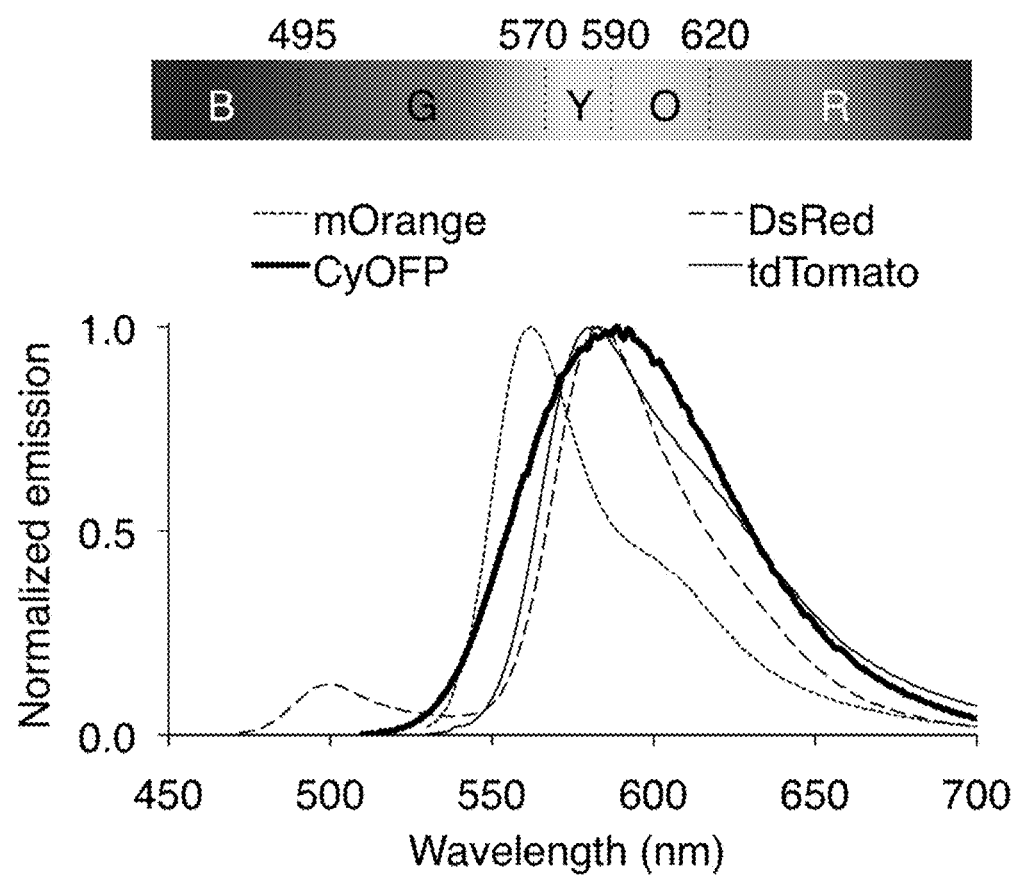
FIGS. 6A-6D show optical characteristics of CyOFP.

Through mutagenesis of the far-red FP mNeptune2[28], we obtained an extremely bright cyan-excitable orange-red fluorescent protein which we named CyOFP (FIG. 1A). CyOFP differs from mNeptune2 by 33 mutations and 2 deletions (Table 2, FIG. 1B). CyOFP has a broad excitation spectrum with wavelengths from 488 to 526 nm exciting with >95% of peak efficiency. This contrasts with most orange-red FPs, which are maximally excited in the 550-610 nm range. CyOFP has peak emission of 589 nm and an average emission wavelength of 595 nm. As 620 nm is considered the orange/red boundary[29], this FP is most properly described as being orange[30], although other FPs with similar or even more blue-shifted emission spectra, such as tdTomato and DsRed, are often termed red FPs (FIG. 6A). A H61M mutation in CyOFP red-shifts the emission spectrum further. H61M CyOFP has a peak excitation wavelength of 534 nm and a peak emission wavelength of 590 nm.

Figure 1C:
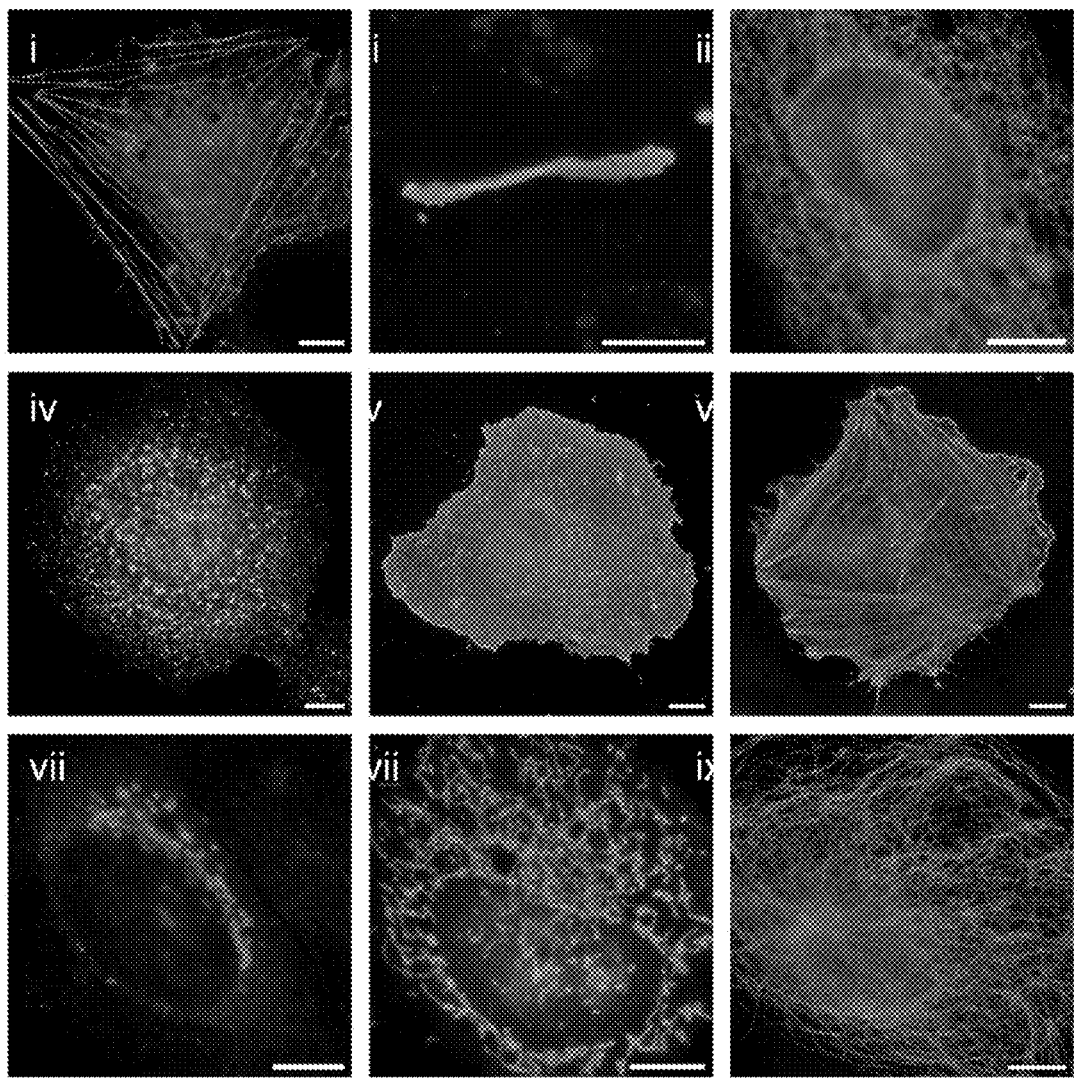
Figure 1D:
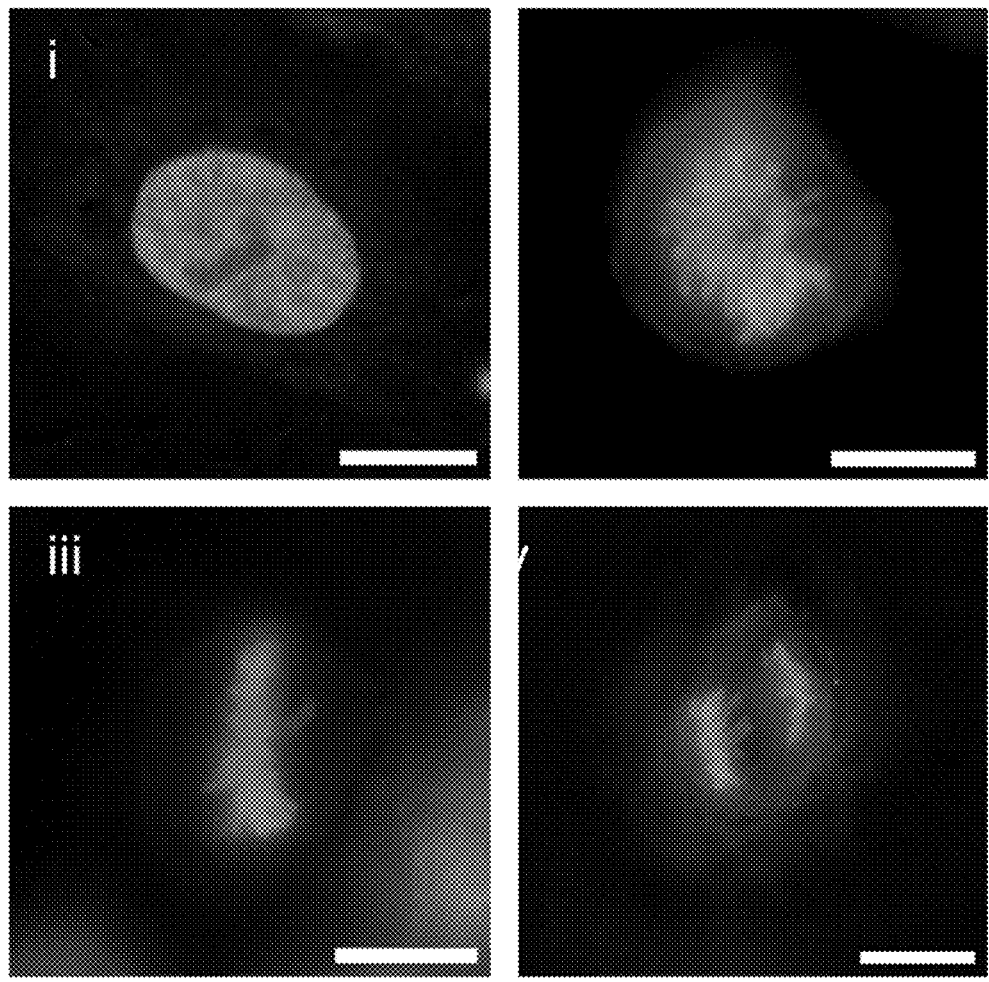
Figure 6B:
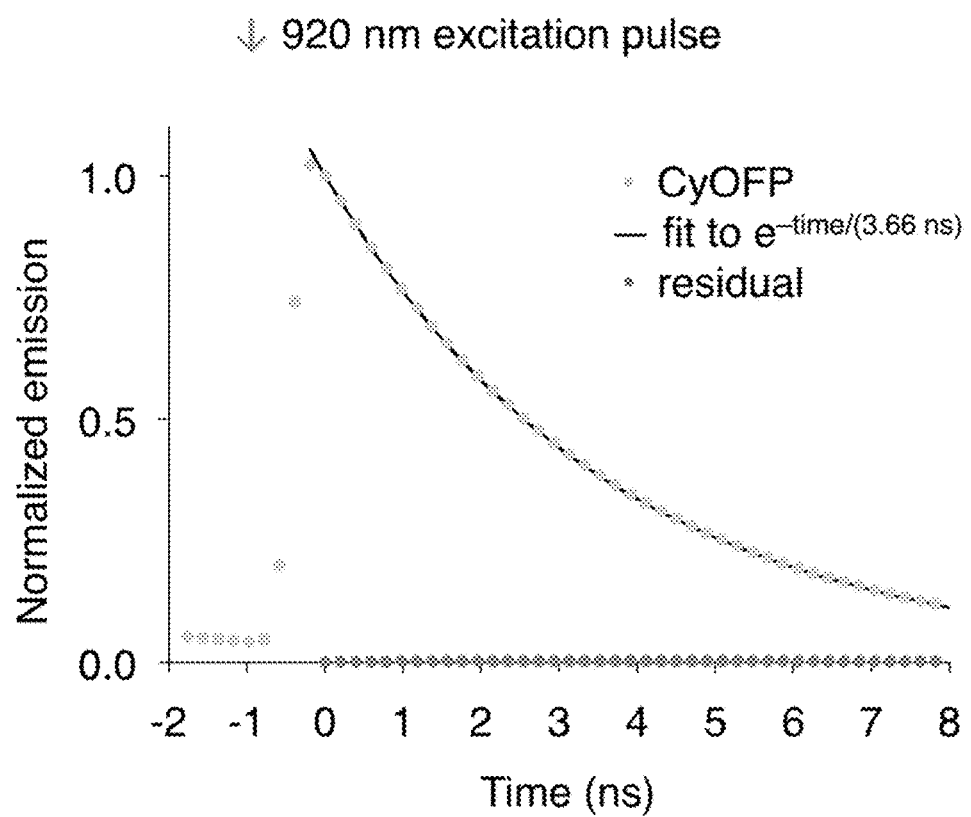
Figure 6C:
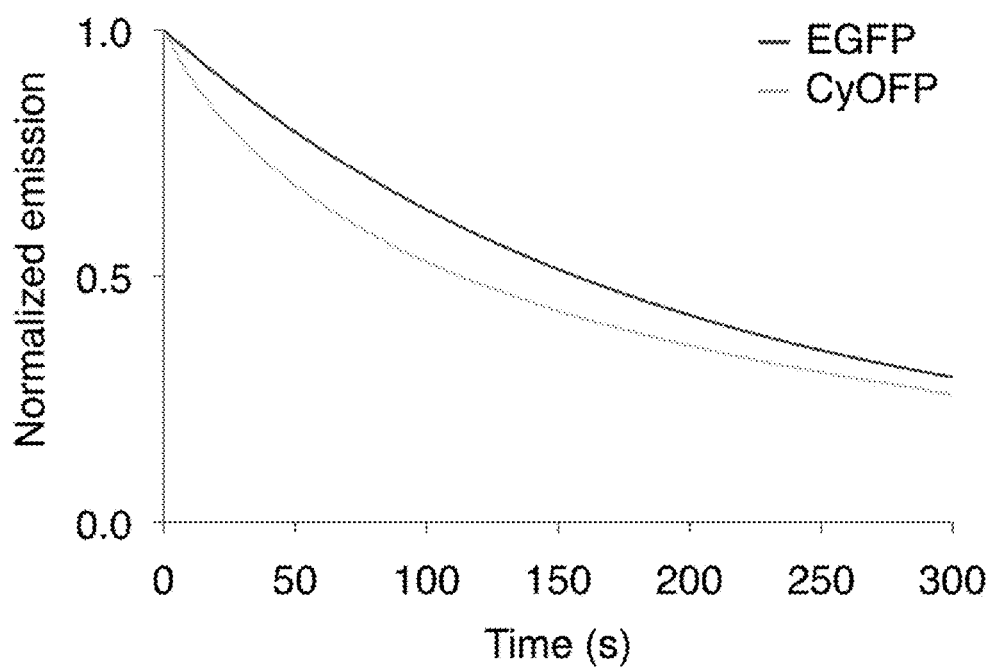
Figure 6D:
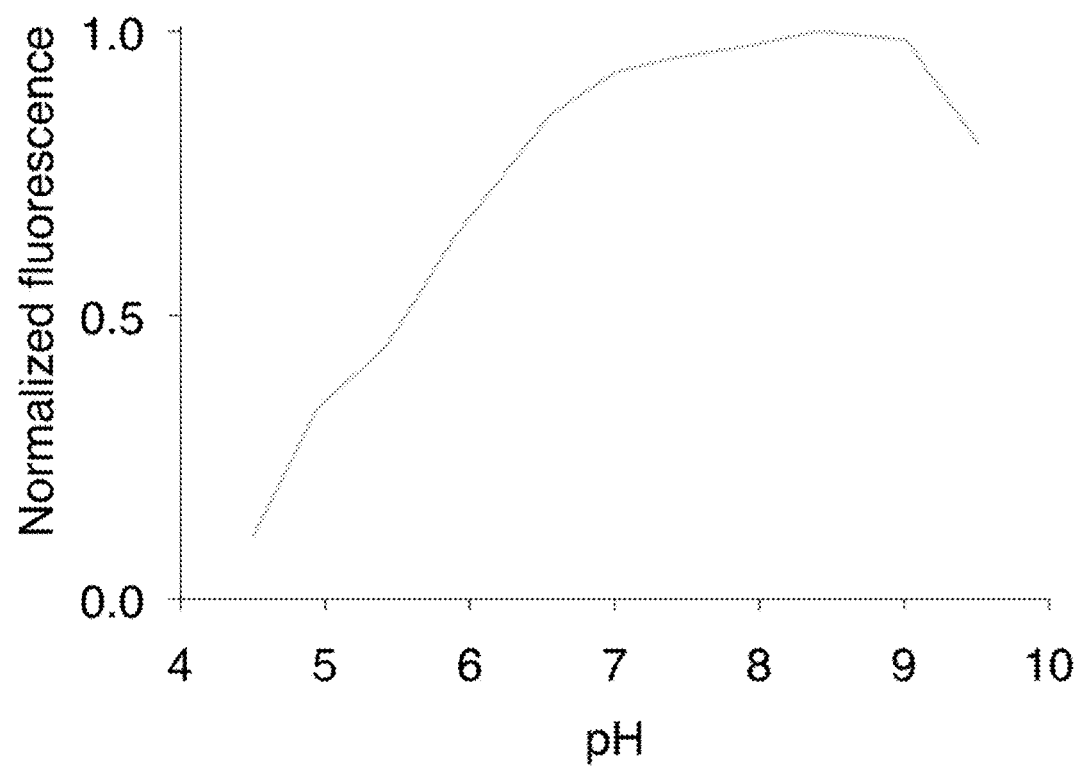

CyOFP has several unique and desirable optical characteristics. In being excited by cyan light, CyOFP demonstrates a large Stokes shift of ~90 nm, but is different from previous LSS orange-red FPs, which are excited by more phototoxic blue light around 440 nm. CyOFP also differs from previous LSS orange-red FPs in having an unusually high QY of 0.76, the highest known QY for an orange-red FP, even surpassing the 0.70 QY of DsRed[31,32] (Table 1). CyOFP fluorescence lifetime was well fit to a single exponential with τ=3.663±0.002 ns (mean of 59 cells±standard error of the mean, FIG. 6B), also the longest reported fluorescence lifetime for an orange-red FP. CyOFP exhibits high photostability under arc-lamp illumination in vitro (120 s for CyOFP compared to 150 s for mEGFP, FIG. 6C), and its fluorescence is stable across a range of pHs with pKa 5.5 (FIG. 6D). CyOFP shows excellent performance in a variety of fusion proteins targeted to various subcellular locations (FIG. 1C), and histone fusions to CyOFP do not interfere with the cell cycle (FIG. 1D).

Novel Mechanism for a Large Stokes Shift in CyOFP

Figure 2A:
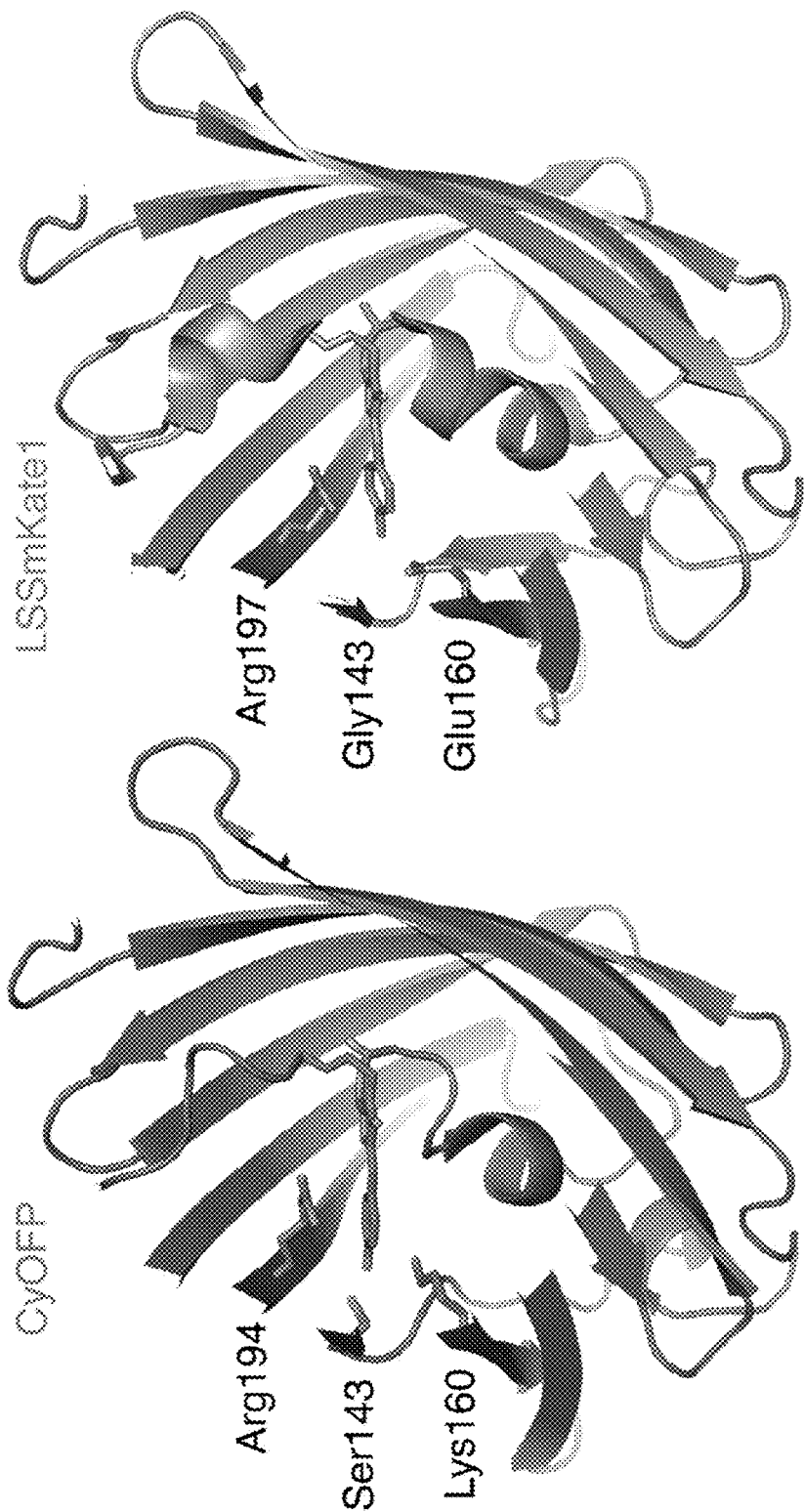
FIGS. 2A-2C show structural characterization of CyOFP.
Figure 2B:
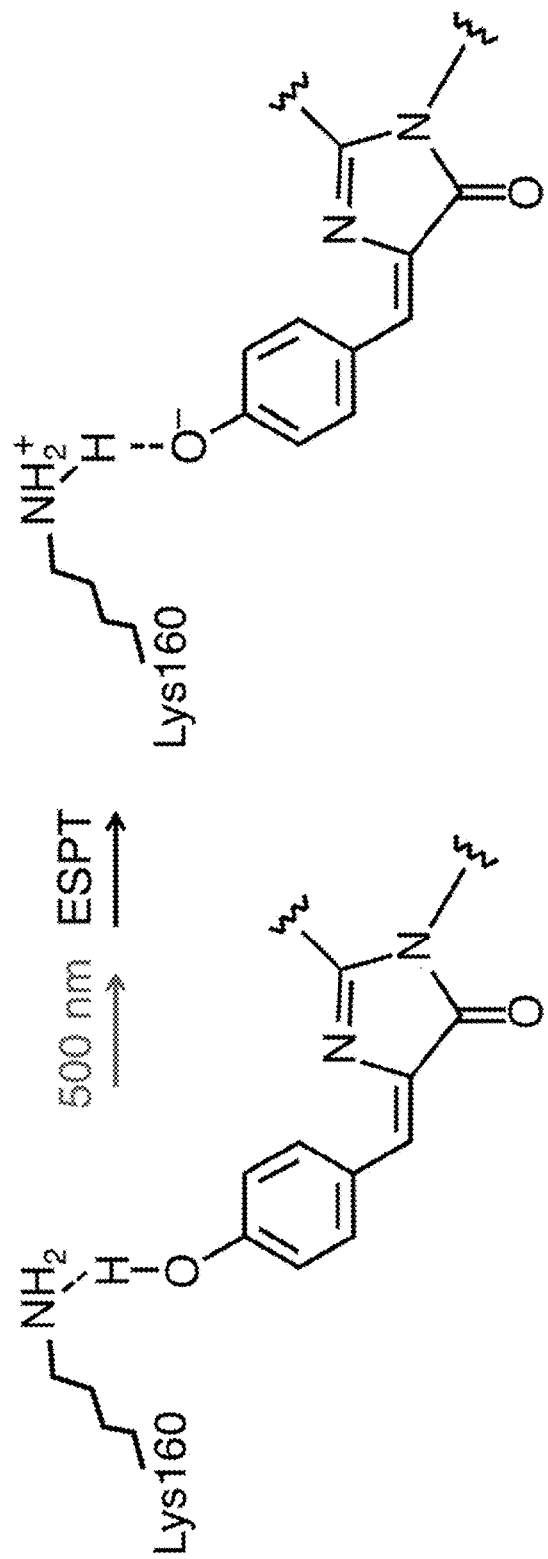
Figure 2C:
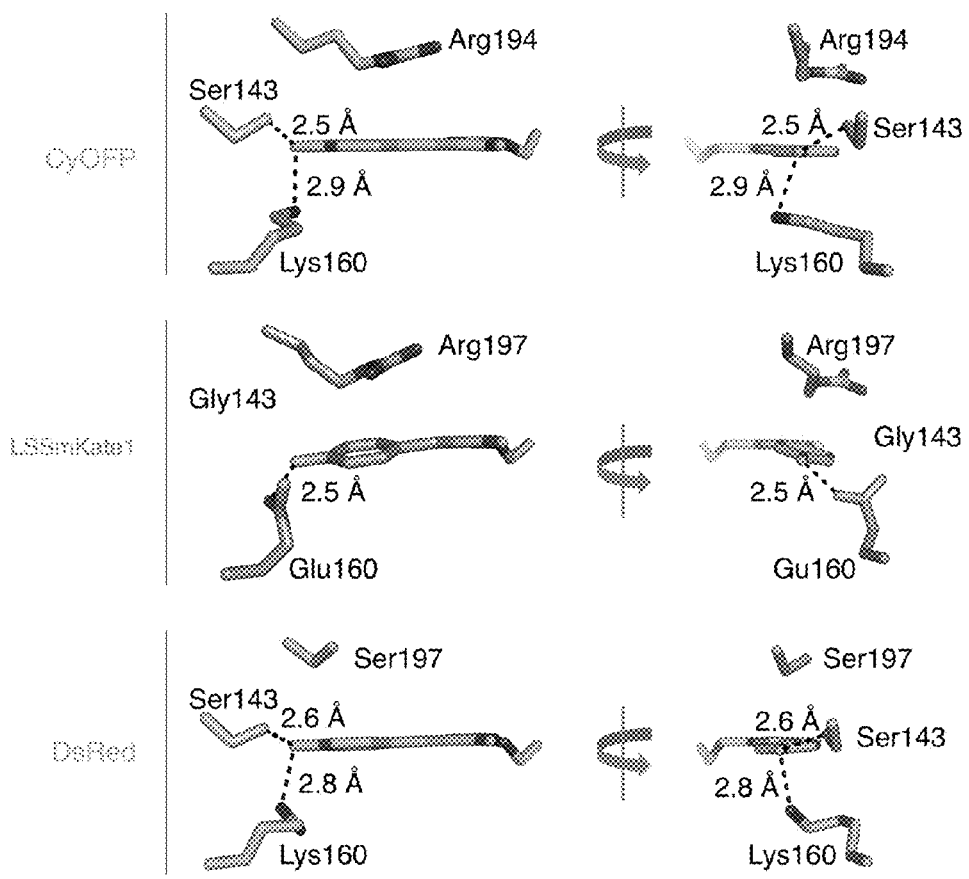
Figure 7A:
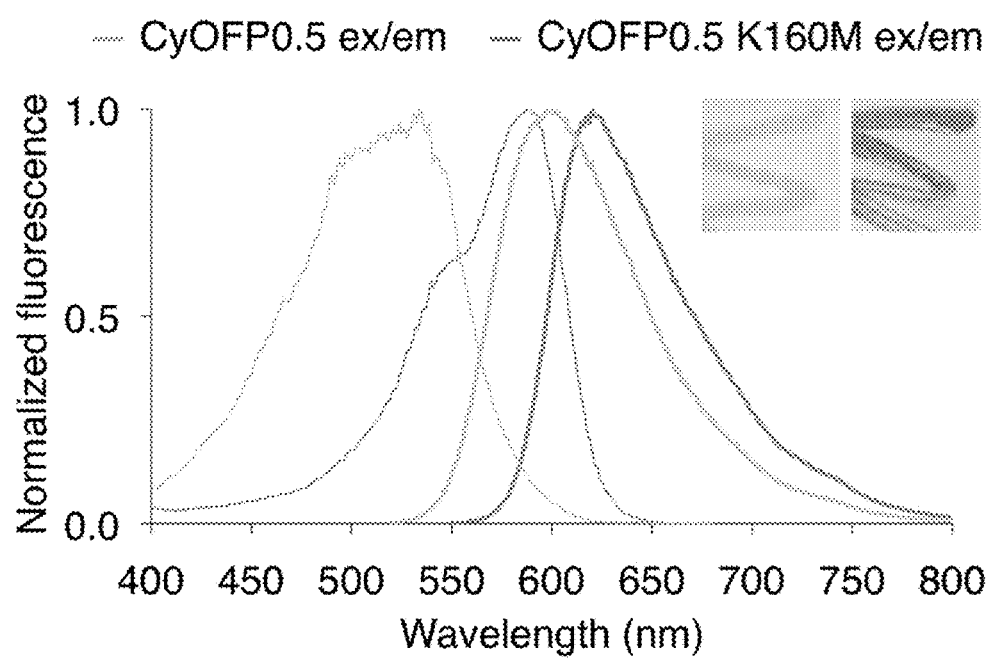
FIGS. 7A-7C show role of Lys160 in the large Stokes' shift of CyOFP.

To understand the mechanism of the large Stokes shift and high QY of CyOFP, we determined the structure of CyOFP0.5, an earlier variant with similar spectra as CyOFP. We obtained an X-ray crystal structure of CyOFP0.5 at 2.39 Å resolution with four chains per crystallographic unit (see Table 3 for crystallographic data). As expected, the chromophore is similar to that of DsRed and tdTomato, and, unlike the mKO and mOrange family of orange FPs[33], does not contain a ring in place of the acylimine group. One residue, Lys160, accounts for the large Stokes shift in CyOFP0.5 (FIG. 7A). Interestingly, the structure revealed that Lys160 is located beneath the chromophore (when the barrel is oriented with termini pointing upwards), and its amino group is positioned to engage in a hydrogen bond interaction with the phenolic hydroxyl group of the chromophore (FIGS. 2A-2C). In chains A-C of the crystal, the Lys160 side chain is in an extended conformation with the amino group beneath the phenolic hydroxyl, with donor-acceptor distances of 2.7-3.0 Å, while in chain D, turns at the Cγ and Cδ atoms cause the amino group of Lys160 to face away from the phenolic hydroxyl group.

Figure 7B:
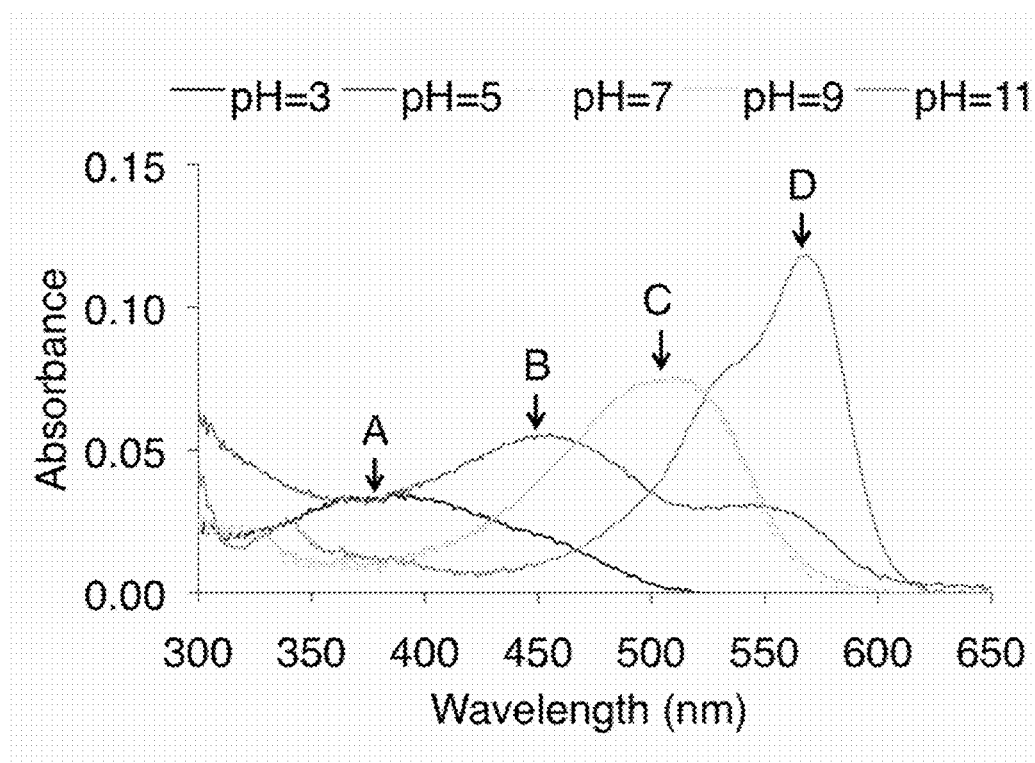

The presence of a hydrogen bond between Lys160 and the chromophore phenol group suggests a novel mechanism for the large Stokes shift in CyOFP. As the absorbance peak of CyOFP is blue-shifted by ~100 nm relative to its predecessor, and chromophore protonation causes blue-shifting of absorbance in FPs, the phenolic hydroxyl group is likely to exist during the ground state in the protonated neutral form. The protonated chromophore phenol group would then serve as a hydrogen bond donor to the neutral form of Lys160 (FIG. 2B). This is consistent with the pKa of Lys160 calculated by PROPKA, which yielded values of 6.06-6.73 in chains A-C of the crystal, implying these Lys160 amino groups are uncharged at neutral pH. Chromophore protonation at neutral pH is also supported by the fact that high pH gives rise to a species with a red-shifted and sharper absorbance spectrum similar to mKate (FIG. 7B). Starting from the doubly neutral state, excited state proton transfer (ESPT) from the chromophore to the Lys160 amino group (FIG. 2B) would explain the large Stokes shift of CyOFP. ESPT also underlies large Stokes shifts in wild-type GFP and other LSS proteins (FIG. 7C), but the use of lysine as an ESPT acceptor appears unique to CyOFP.

Figure 7C:
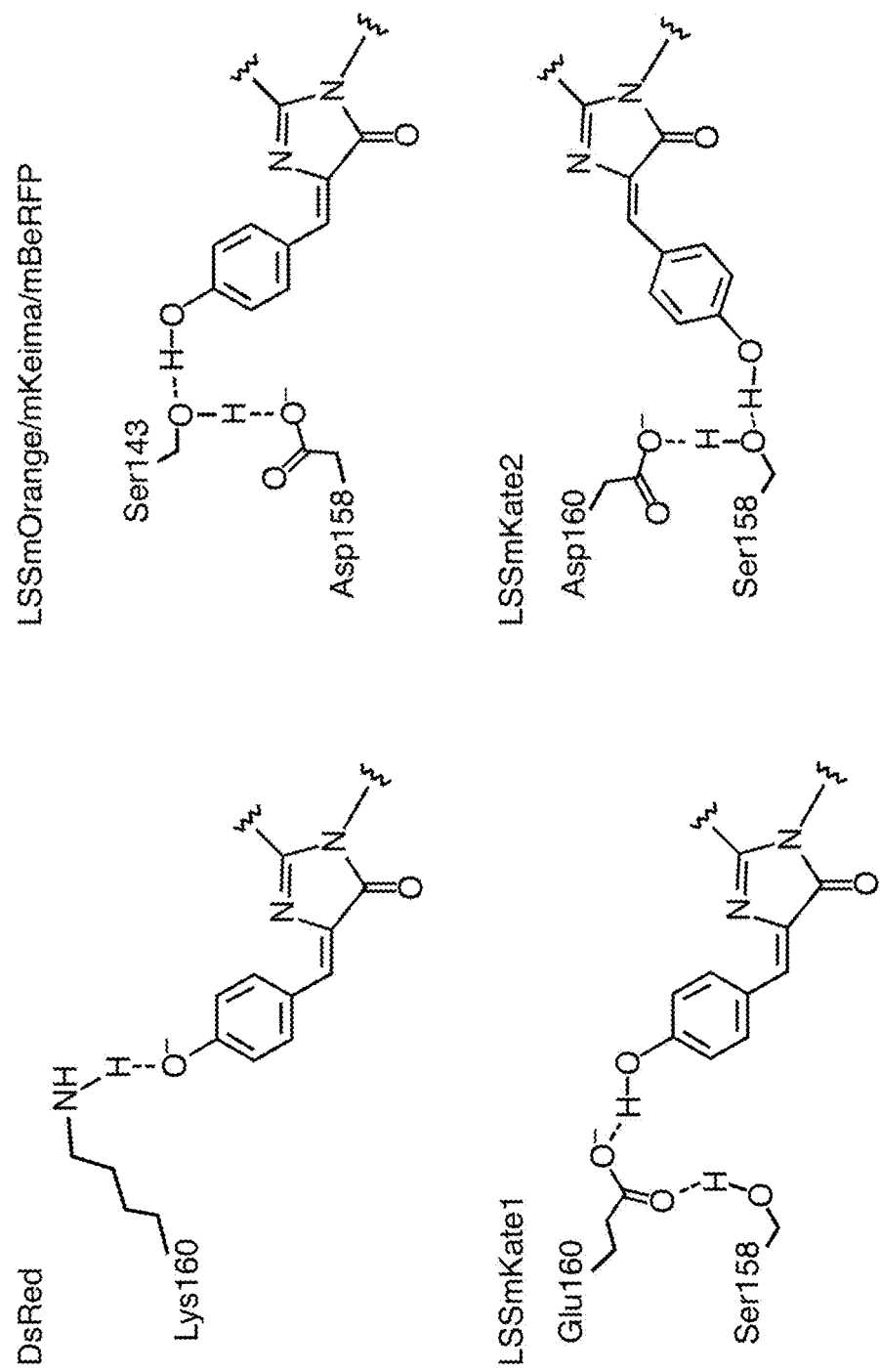

CyOFP shows surprising similarity to DsRed in the arrangement of hydrogen bond partners near the chromophore phenol group. Specifically, positions 143 and 160 are also Ser and Lys respectively in DsRed and mApple (FIG. 2C, FIG. 7C). Indeed, following EPST, the chromophore of CyOFP would be predicted to be similar to those of DsRed and mApple in being anionic and hydrogen-bonded to Ser143 and Lys160 (FIG. 2B, FIG. 7C). Thus, differences elsewhere in CyOFP compared to DsRed and mApple apparently modulate the pKa of the chromophore or Lys160 to favor the protonation of the chromophore over Lys160 at neutral pH specifically in CyOFP.

The crystal structure of CyOFP also suggests several possible explanations for the higher QY of CyOFP compared to other LSS orange-red FPs. The chromophore interactions of CyOFP are most similar to those of LSSmKate1, whose structure has also been characterized[34]. LSSmKate1 also contains an ESPT acceptor, a Glu side chain, at position 160, but the QY of LSSmKate1 is 0.08 versus 0.76 for CyOFP. Compared to LSSmKate1, CyOFP shows three major differences (FIG. 2C). First, the CyOFP chromophore is more planar. Second, the CyOFP chromophore is more tightly packed on its top surface by Arg194 (homologous to Arg197 in LSSmKate1) due to a more planar conformation of the Arg side chain. Finally, the chromophore phenol group in CyOFP engages in hydrogen bonds with two amino acids, Ser143 and Lys160, as opposed to only Glu160 in LSSmKate1, due to a mutation of position 143 to Gly in LSSmKate1. Each of these differences would be expected to constrain chromophore motion and thus increase QY in CyOFP compared to LSSmKate1. In particular, hydrogen bonding to Ser143 and Lys160 may be a common mechanism for high QY in CyOFP, mApple, and DsRed.

Single-Excitation Dual-Emission Imaging with CyOFP and GFP

Figure 8A:
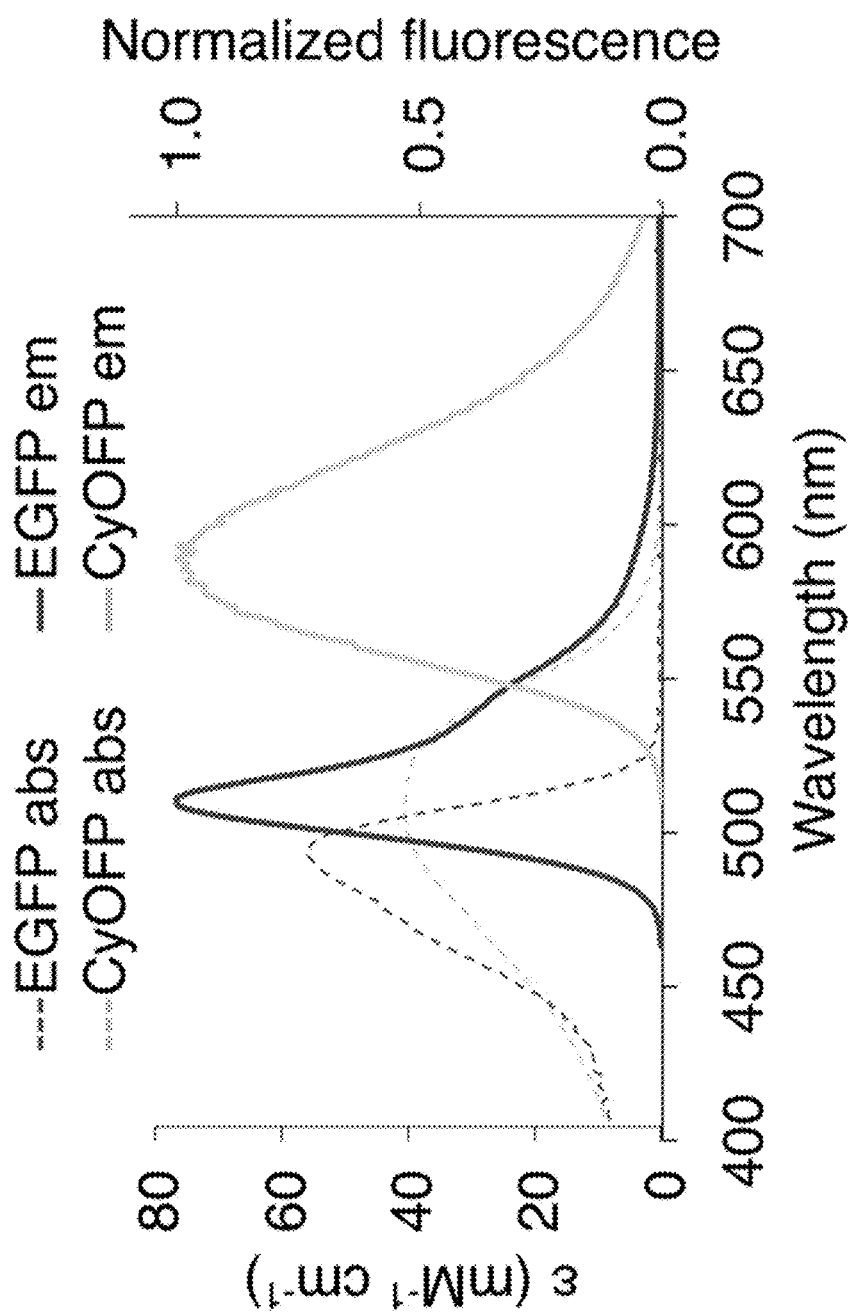
FIGS. 8A-8E show CyOFP in single-excitation dual-emission imaging.
Figure 8B:
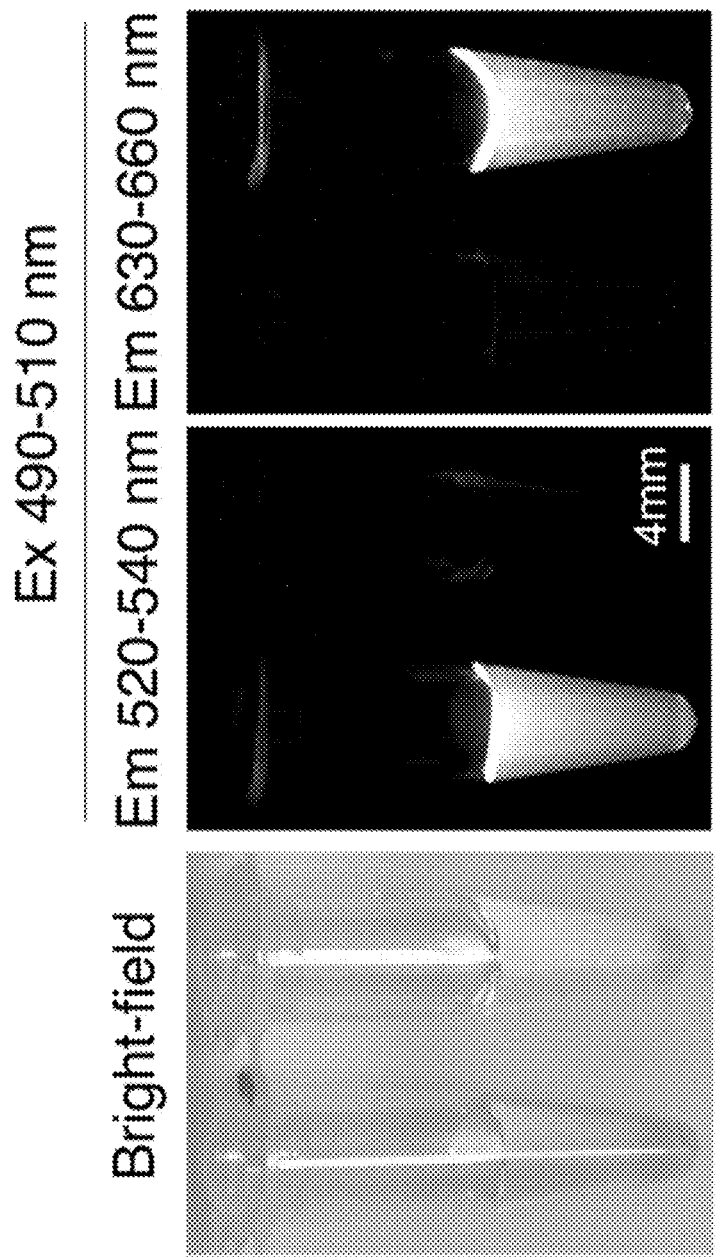

CyOFP's spectral attributes make it ideal for single-excitation dual-emission imaging together with a GFP. As a demonstration, we excited CyOFP and the Clover variant of GFP[35] simultaneously with a 490-510-nm excitation filter, which efficiently excites both proteins (FIG. 8A). Using bandpass filters, we collected emissions at 520-540 nm, which should be specific for Clover GFP emissions, and 630-660 nm, which should be specific for CyOFP emissions (FIG. 8A). As expected, we found that Clover GFP is specifically detected in the 520-540-nm channel, while CyOFP is specifically detected in the 630-660-nm channel (FIG. 8B).

Figure 8C:
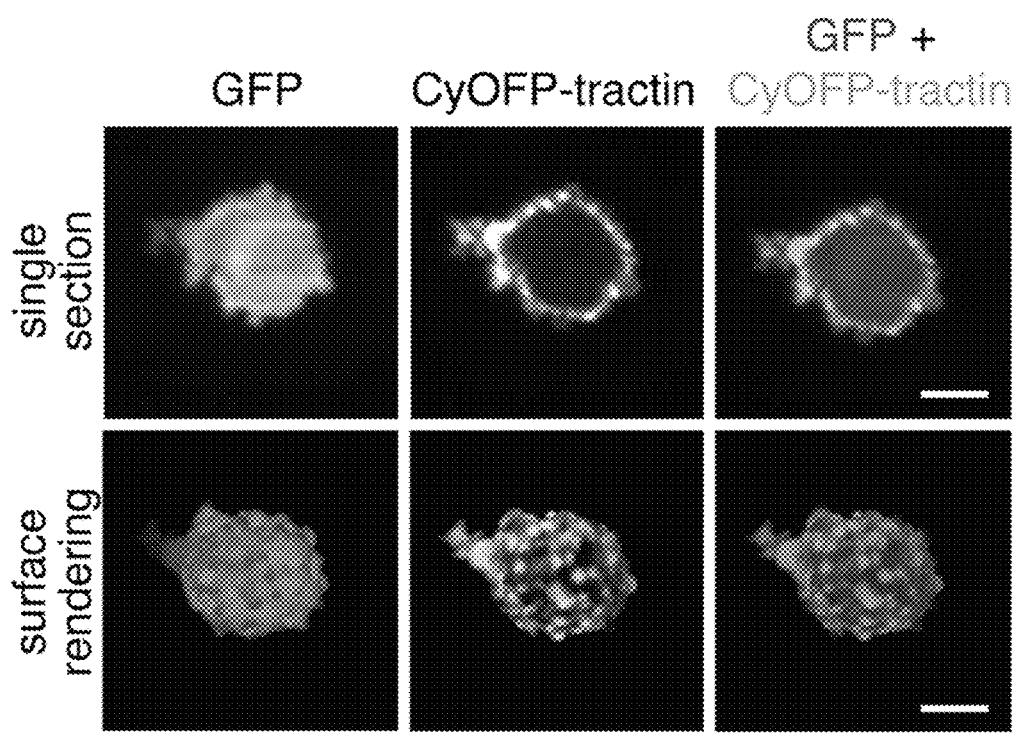
Figure 8D:
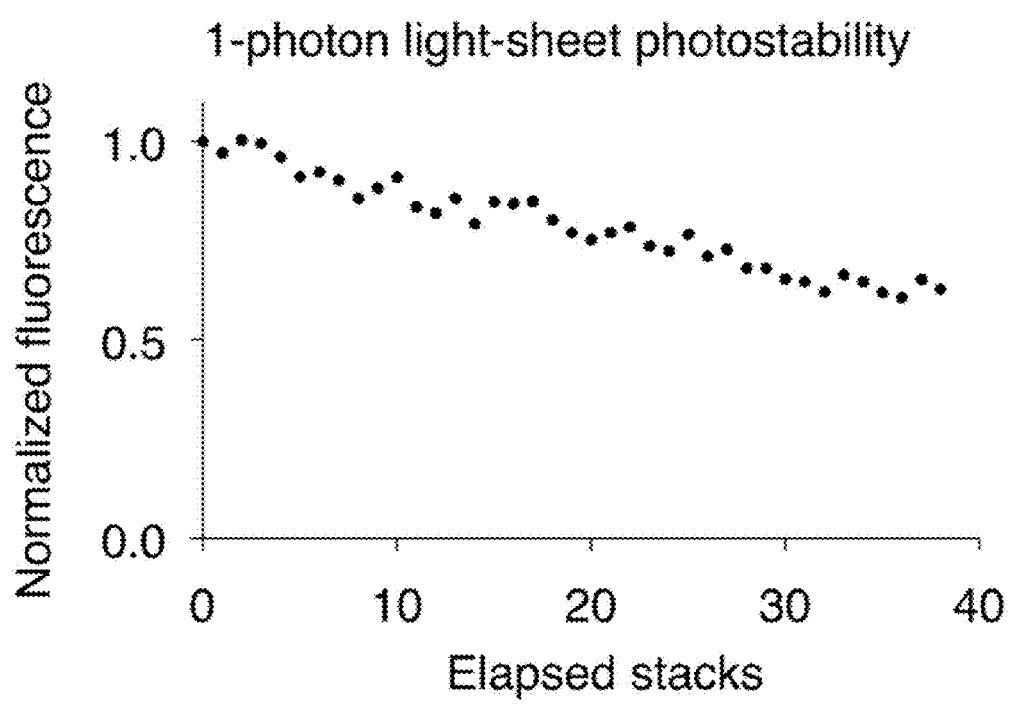

We next tested CyOFP performance in single-excitation dual-emission microscopy. Specifically, we imaged MV3 melanoma cells expressing CyOFP fused to the actin marker tractin and cytosolic EGFP in a three-dimensional (3D) environment using axially swept light-sheet microscopy, exciting both fluorophores with a 488-nm excitation laser and collecting green and orange emissions on two high-speed cameras[10]. Simultaneous 3D imaging of EGFP and CyOFP-tractin over time allowed us to ascertain the role of actin in the formation of non-apoptotic blebs (FIG. 8C). We observed that these blebs formed initially as actin-free structures marked exclusively by cytosolic EGFP, but were later enriched for polymerized actin. In addition, we observed that CyOFP retained the majority of its fluorescence for over 40 stacks, each consisting of 126 optical sections spaced 160 nm apart (FIG. 8D). Thus CyOFP can be used in one-photon light-sheet excitation for simultaneous imaging with EGFP over long time courses.

Simultaneous Two-Photon Imaging of CyOFP and GFP-Based Probes

Figure 3A:
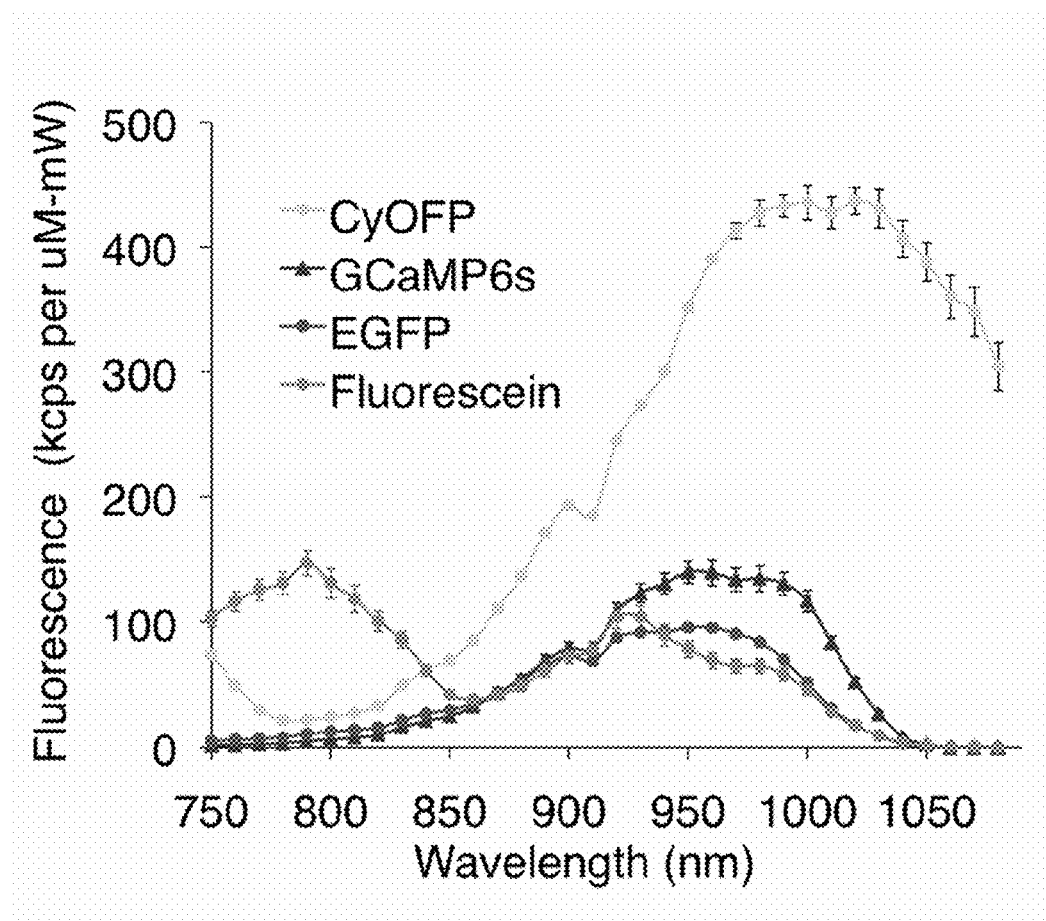
FIGS. 3A-3D show simultaneous dual-emission two-photon imaging of CyOFP with GFP-based reporters.

CyOFP may be especially useful together with GFP-based sensors for multi-photon structural and functional imaging, where using multiple Ti-Sapphire lasers or adding an OPO to excite green and red fluorophores simultaneously is uncommon due to expense and complexity. CyOFP is well excited in two-photon mode with a broad peak between 900 and 1060 nm (FIG. 3A). At 920-940 nm, wavelengths commonly used to excite GFP-based probes[36-38], CyOFP has higher brightness than EGFP or the GFP-based calcium sensor GCaMP6s (FIG. 3A). CyOFP and GFP-based probes can thus be simultaneously excited in two-photon mode using a single excitation wavelength and their emissions separated with appropriate filters.

Figure 3B:
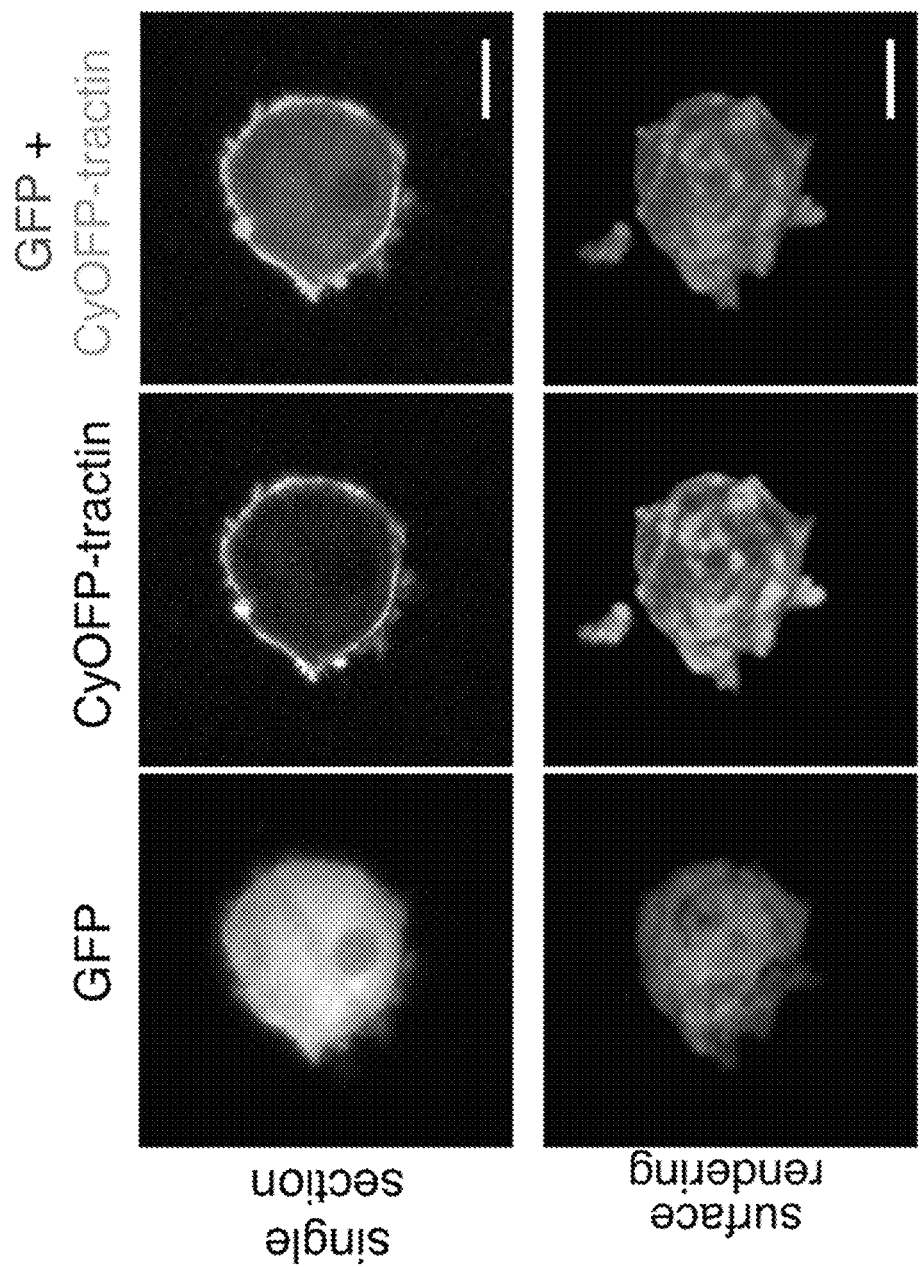
Figure 8E:
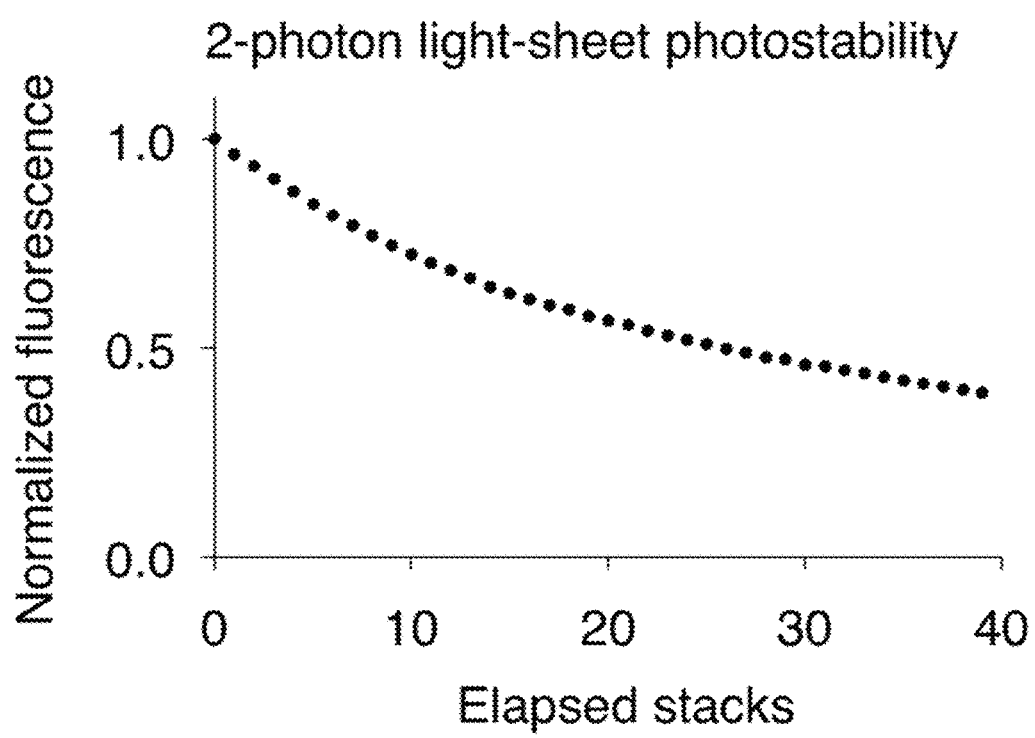
Figure 9A:
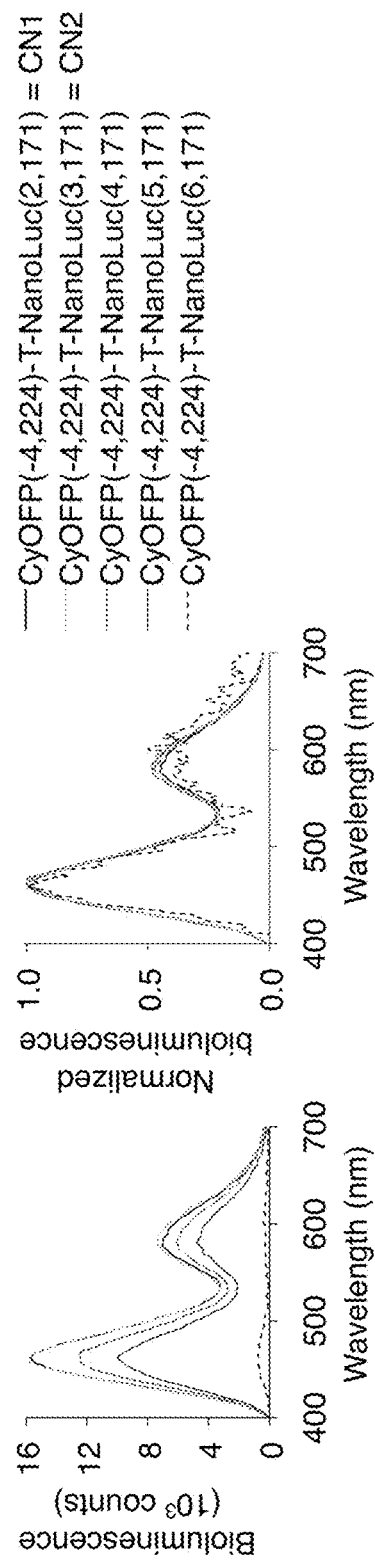
FIGS. 9A-9D show optimization of linkers in Antares.
Figure 9B:
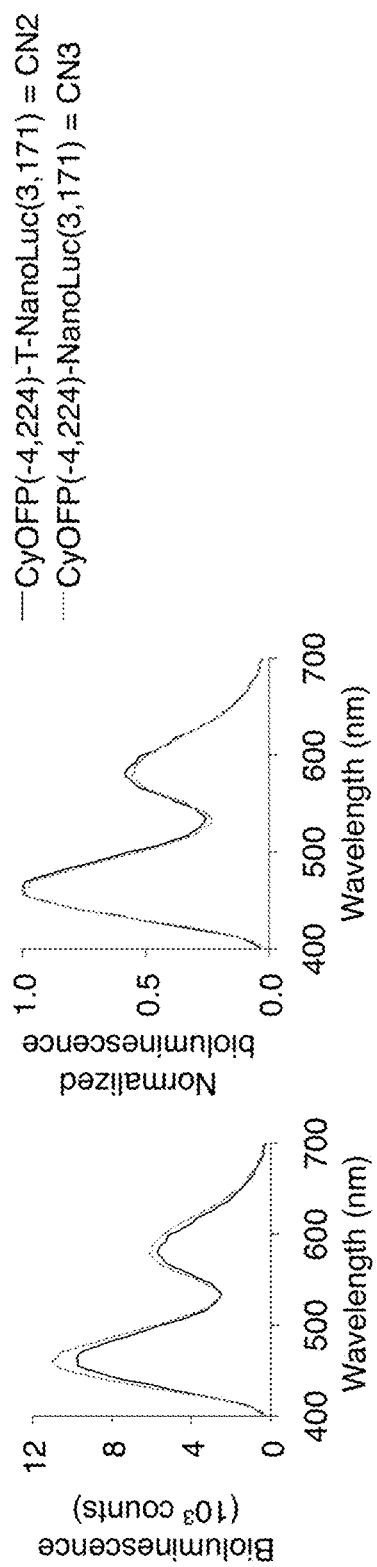
Figure 9C:
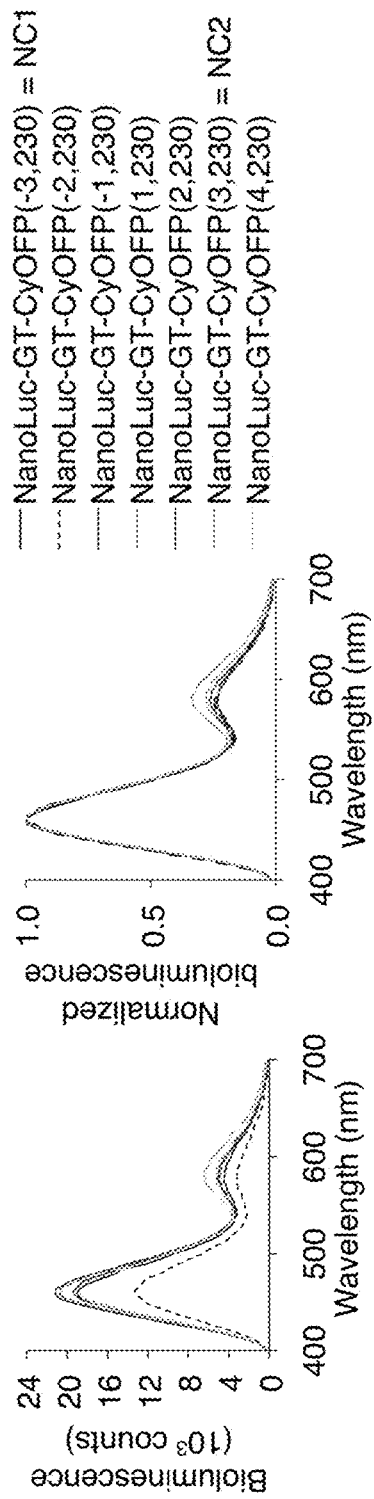
Figure 9D:
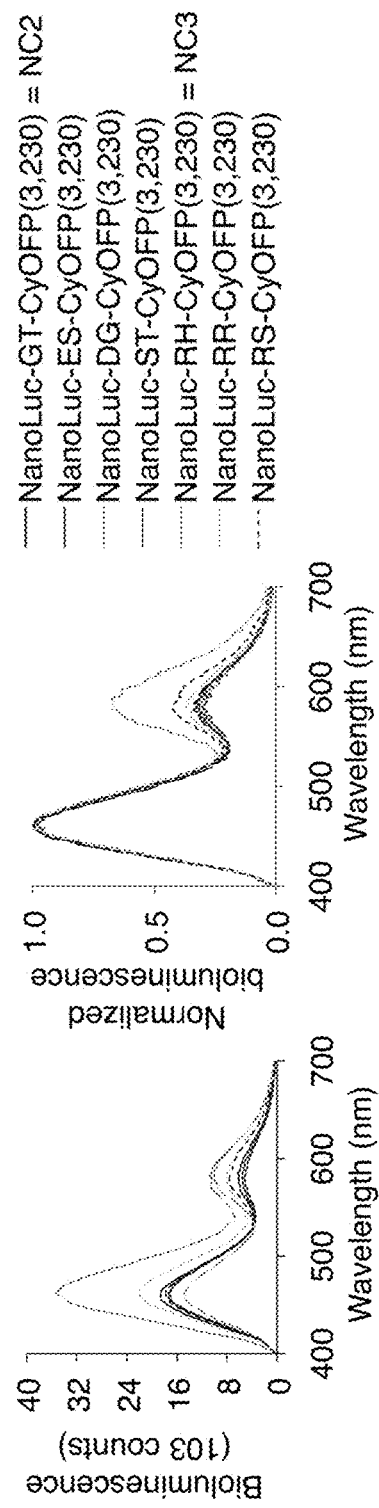

Two-photon excitation is advantageous for Bessel-beam light-sheet microscopy, where the non-linearity of two-photon excitation attenuates the side lobes of the effective Bessel beam, reducing out-of-focus excitation[8,39]. Here, imaging of two fluorescent probes would be greatly simplified by the use of simultaneously excitable but distinctly emitting fluorophores. To test this, we imaged the MV3 cells coexpressing CyOFP-tractin and cytoplasmic EGFP with two-photon Bessel-beam light-sheet microscopy. We observed dynamic actin protrusions with enhanced resolution compared to one-photon excitation (FIG. 3B). CyOFP again performs well in time-lapse imaging, retaining most of its fluorescence over 25 stacks of 126 sections each (FIG. 8E).

Figure 3C:
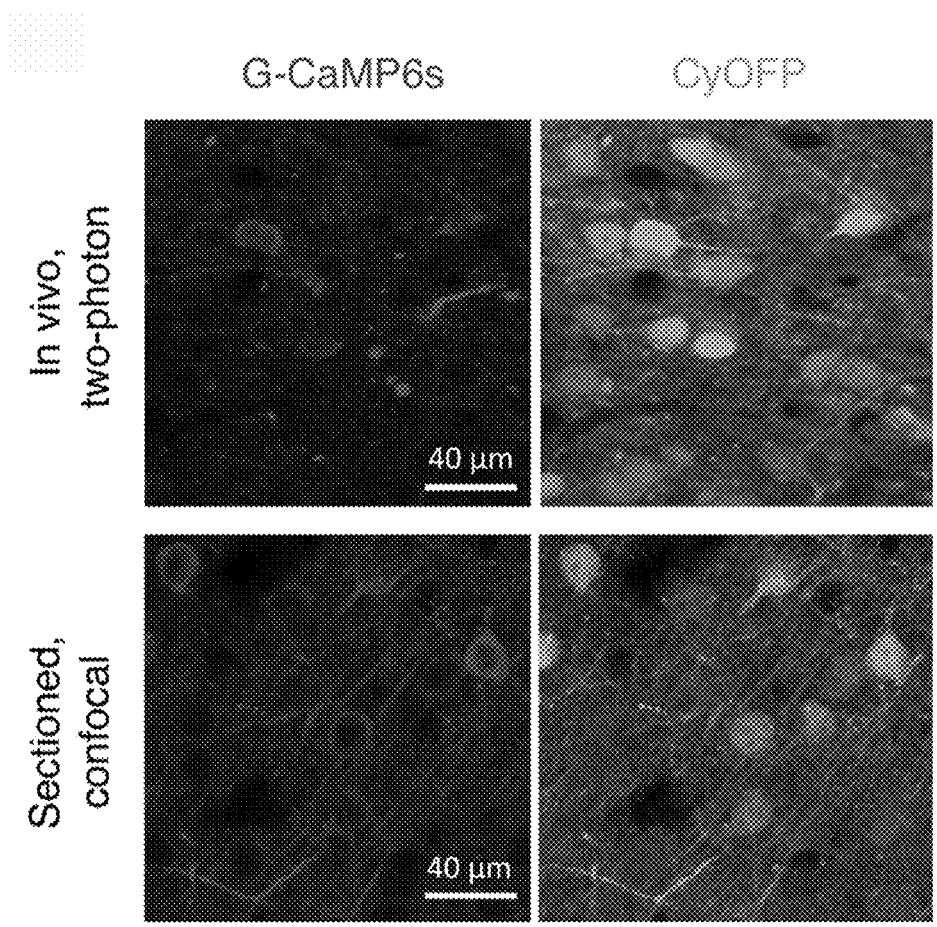
Figure 3D:
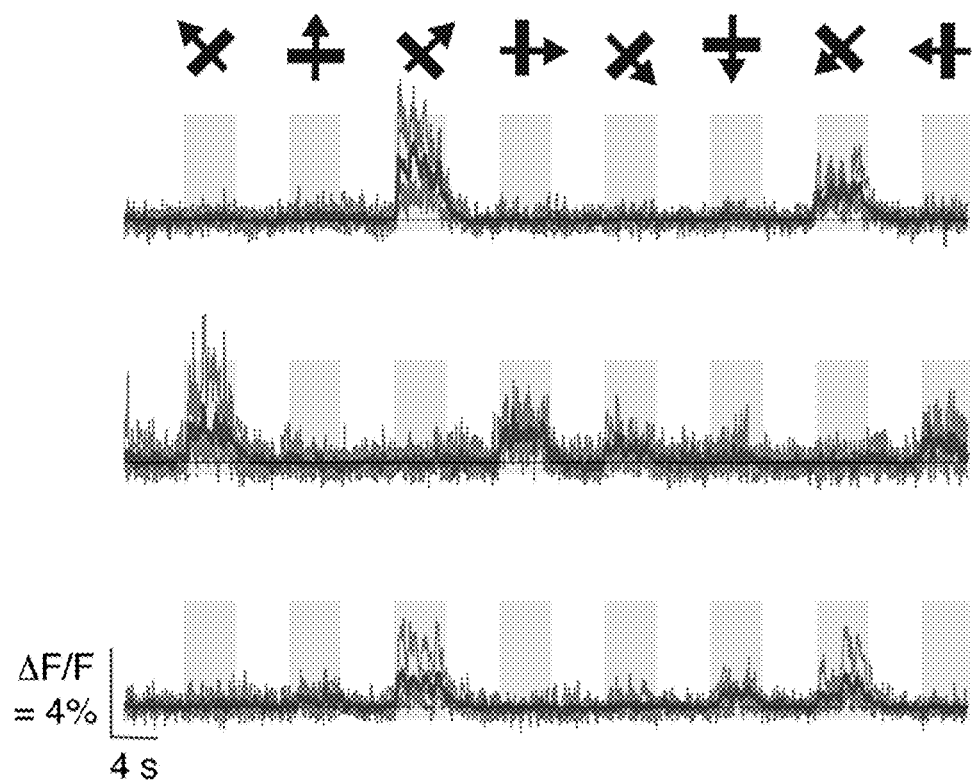

In the mouse brain, where GCaMP-family sensors are typically used with two-photon excitation to visualize neuronal activity in deep layers[36-38], CyOFP could serve as an anatomical fill or a reference channel. To test this, we used a bicistronic adeno-associated virus to co-express CyOFP with GCaMP6s in mouse primary visual cortex in vivo. Upon two-photon excitation at 940 nm, CyOFP fluorescence could be seen to fill the neuronal cell bodies and dendritic processes without noticeable subcellular aggregation after 4 weeks of expression (FIG. 3C). Somatic calcium transients of orientation-tuned neurons were simultaneously recorded with GCaMP6s, similar to previously reported studies[36-38] (FIG. 3D). Thus CyOFP and GCaMP6s enable simultaneous two-photon imaging of cellular structure and calcium transients in living mouse brains using a single excitation wavelength.

Antares, a Bright Orange-Red Bioluminescent Protein Based on CyOFP

Figure 4A:
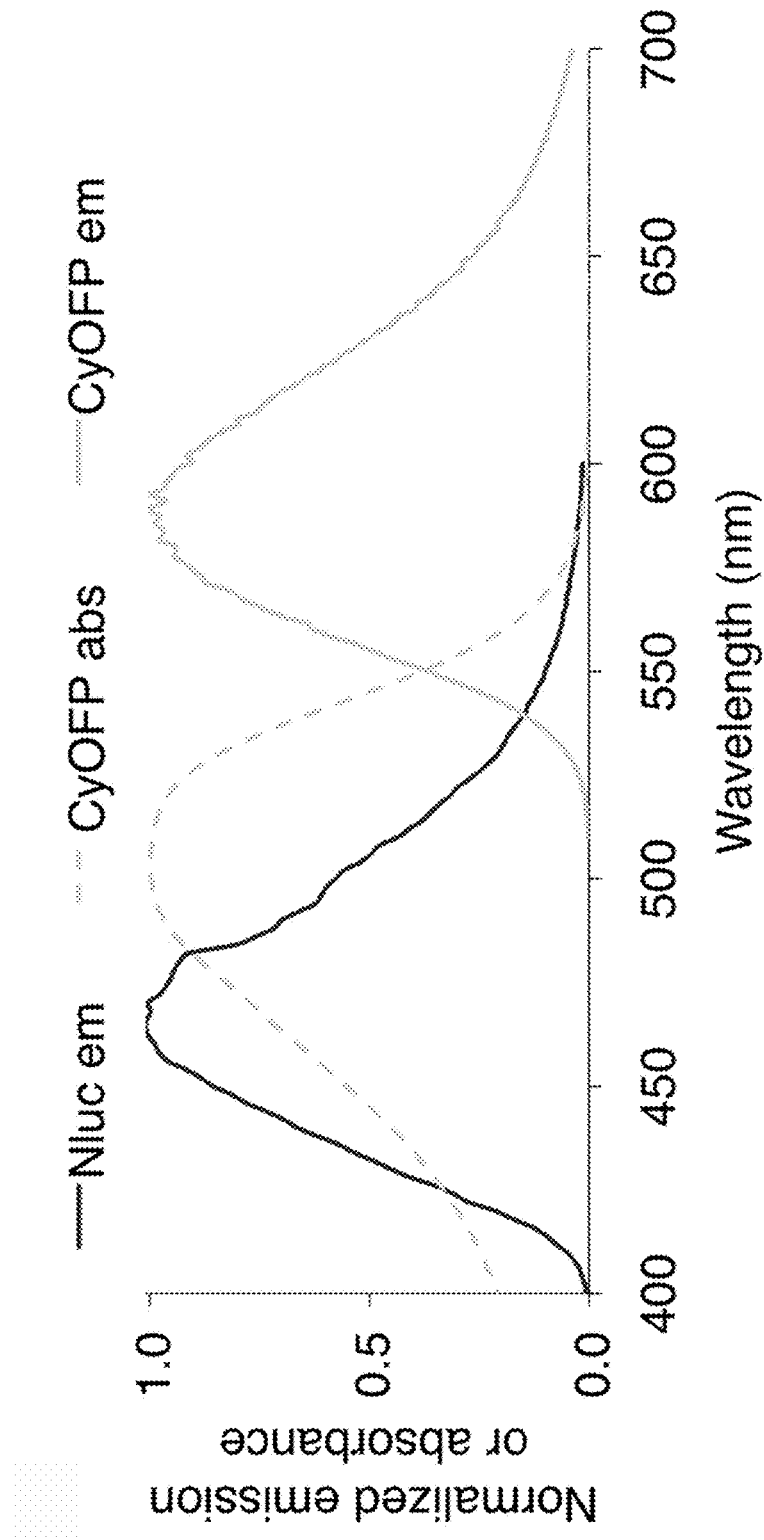
FIGS. 4A-4C show development of a BRET system with NanoLuc and CyOFP.

We noticed that CyOFP has ideal spectral characteristics to be a BRET acceptor for NanoLuc, potentially providing a way to improve in vivo BLI. The emission spectrum of NanoLuc overlaps substantially with the absorption spectrum of CyOFP (FIG. 4A), so if the two proteins are in close enough proximity, the excited-state energy of the oxidized reaction intermediate in the NanoLuc active site could be transferred to excite CyOFP by BRET, leading to emission with the spectrum and QY of CyOFP. In addition to its unusually high QY of 0.76, nearly half of CyOFP emission occurs above 600 nm, which is highly desirable as absorbance and scattering of light in mammalian tissue decreases dramatically above 600 nm. We therefore hypothesized that we could create a fusion of CyOFP and NanoLuc that would effectively perform as a highly active red-emitting bioluminescent protein.

Figure 4B:
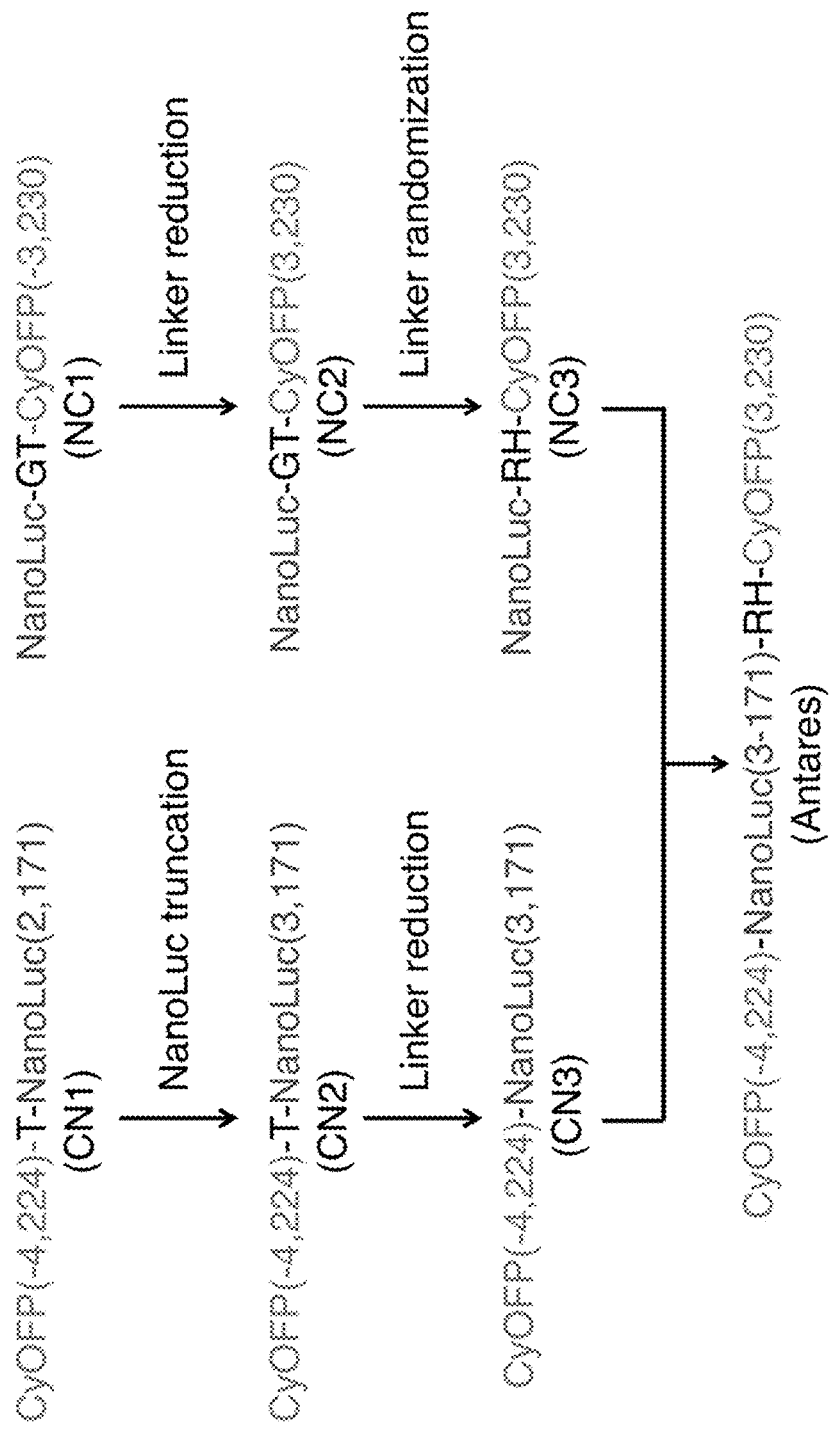
Figure 4C:
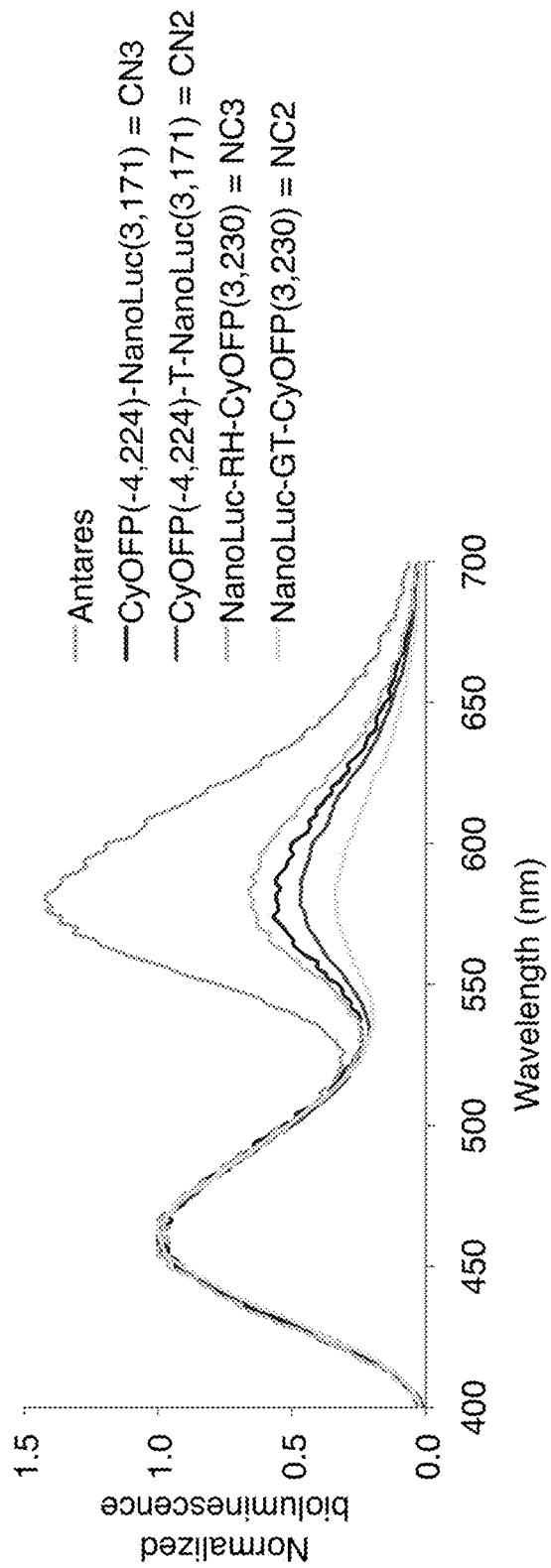

To create a red-emitting bioluminescent protein, we constructed and tested fusions between CyOFP and NanoLuc (FIG. 4B). Multiple rounds of mutagenesis were performed to optimize linkages for high BRET in CyOFP-NanoLuc and NanoLuc-CyOFP fusions (FIG. 9). We then combined the fusions and found that BRET was further enhanced with CyOFP at both ends of NanoLuc (FIG. 4C). We named this final fusion protein Antares, after the highly luminous binary star system that consists of a dim blue star and an exceptionally bright orange-red star.

Improvement of Bioluminescence Imaging in Living Animals with Antares

We tested Antares for its ability to improve non-invasive deep-tissue BLI of gene expression. To identify the best-performing BLI reporters to compare with Antares in vivo, we first performed a small screen of reporters in cells in a mouse tissue phantom with optical transmission and scattering properties similar to a living animal. As substrates are applied directly to cells in a tube before placement in the phantom, this method allowed us to test luciferases at equal concentrations of substrate and not be confounded by the uncertainty of substrate uptake in vivo. We included in this screen FLuc (expressed from the codon-optimized luc2 gene) as the most commonly used luciferase for in vivo mammalian imaging, Nano-lantern as a BRET system with higher turnover and higher QY than FLuc, a fusion of RLuc8.6-535 and TurboRFP635 (BRET6) as a BRET system with higher turnover and redder emission than FLuc[26], and NanoLuc alone. For Nano-lantern and BRET6, we tested a soluble formulation of coelenterazine (sCTZ) and Viviren, a coelenterazine derivative with less auto-oxidation, both of which have been observed to yield larger BLI signals than standard coelenterazine formulations[40,41]. For NanoLuc and Antares, we tested sCTZ and furimazine (FRZ).

Figure 5A:
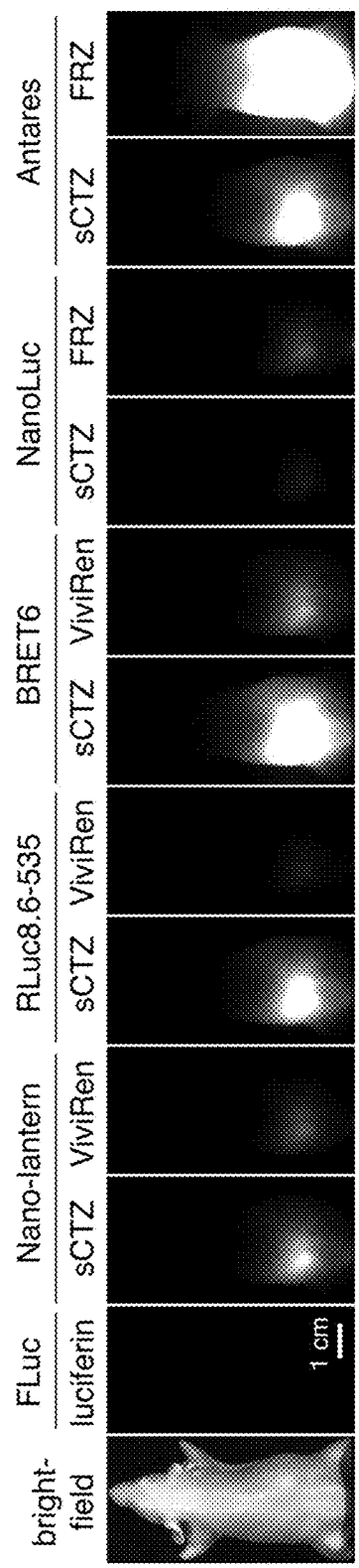
FIGS. 5A-5D show that Antares is superior to other reporters in bioluminescence in living mice and mouse phantoms.
Figure 5B:
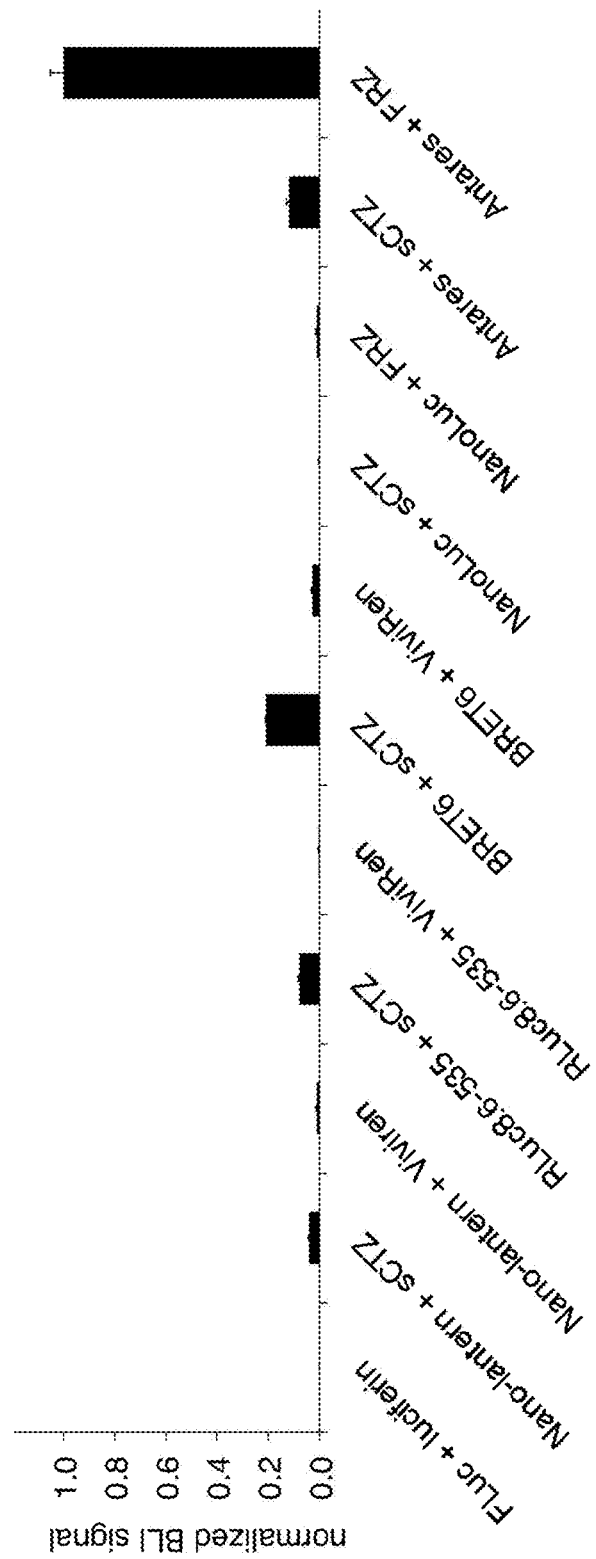

We observed that Antares with FRZ produces the most detectable emission of all luciferase-enzyme combinations tested (FIGS. 5A, 5B). Furthermore, Antares with FRZ was the only condition to produce more emission than every other condition with statistical significance ($p<0.0001$ by one-way ANOVA and $p<0.0001$ by Tukey's post-hoc test for each pair-wise comparison). Of note, Antares with FRZ was 4.8-fold brighter than the second-brightest reporter-substrate combination, BRET6 with sCTZ, and >2000-fold brighter than FLuc with luciferin (FIGS. 5A, 5B). Interestingly, NanoLuc alone with FRZ was 84-fold weaker than Antares with FRZ, and indeed was weaker than most other reporter-substrate combinations (FIGS. 5A, 5B), demonstrating the beneficial effect on tissue penetration of shifting NanoLuc emission to redder wavelengths via BRET to CyOFP. Overall, this experiment identified two BRET systems with orange-red FP acceptors, BRET6 with sCTZ and Antares with FRZ, as the two most promising probes for further in vivo testing.

Figure 5C:
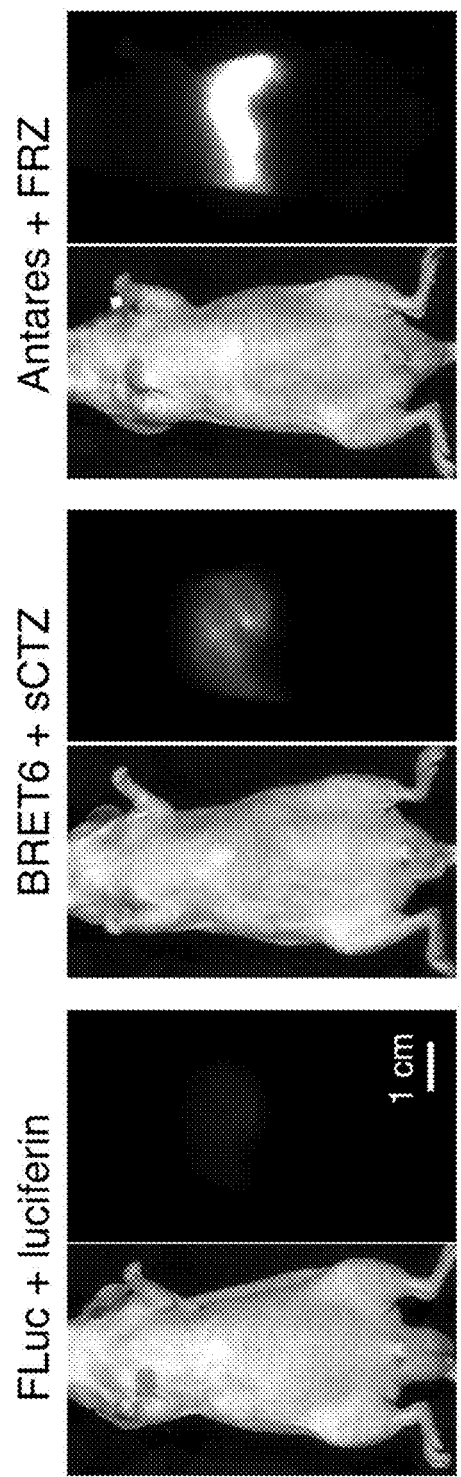
Figure 5D:
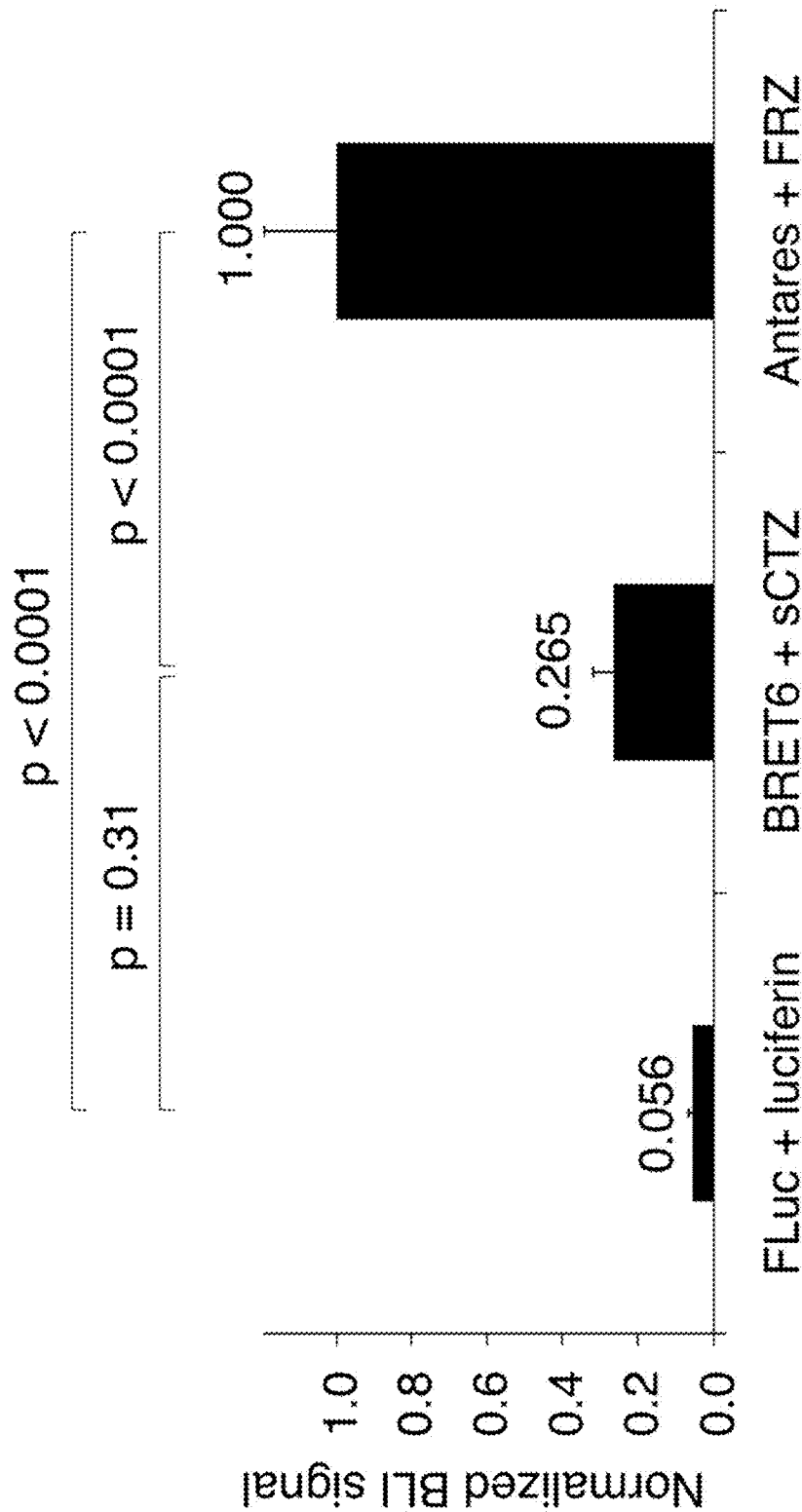

Finally, we performed non-invasive BLI of living mice expressing Antares, BRET6, or FLuc in the liver to compare the sensitivity of these three reporters We found that Antares produced the most detectable signals ($p<0.0001$ by one-way ANOVA, FIGS. 5C, 5D). Specifically, Antares emissions detected upon administration of 330 nmol FRZ were 3.8-fold higher ($p<0.0001$ by Tukey's post-hoc t-test) than those from BRET6 upon administration of the same molar amount of sCTZ. Of note, Antares emissions were 18-fold higher ($p<0.0001$ by Tukey's post-hoc test) than those from FLuc after administration of a 10.7-μmol (3-mg) dose of luciferin, currently the standard method for performing BLI. In this experiment, although BRET6 output trended higher than FLuc output, the difference was not statistically significant (p=0.31 by Tukey's post-hoc test). In summary, these results show that the bioluminescent output of Antares expressed in vivo is many times brighter than that of BRET6 and FLuc, and thus identify Antares as the most sensitive reporter protein for in vivo BLI described so far.

Discussion

In this study, we have described CyOFP, an orange FP with two novel useful features, cyan excitability and exceptional brightness. These features enable CyOFP to address long-standing issues in two distinct optical imaging modalities, optical sectioning microscopy and bioluminescence imaging. We found that CyOFP provides bright signals that can be co-excited with a GFP and its spectrally similar derivatives, but collected separately. We demonstrated that CyOFP and a GFP can be imaged simultaneously using advanced light-sheet and two-photon techniques with two lasers or a laser and an OPO. We further found that CyOFP is a uniquely suitable acceptor for resonance energy transfer from NanoLuc, and engineered a fusion protein, Antares, that effectively coupled the high substrate turnover of NanoLuc to the high quantum yield and orange-red light emission of CyOFP. Antares enabled imaging of gene expression in living mice with 18-fold higher brightness than the commonly used firefly luciferase.

CyOFP is distinct from previous LSS FPs in its optical properties, with a less dramatic Stokes shift but with much higher brightness. The large Stokes shift in previously described LSS orange-red FPs is believed to involve ESPT from the protonated phenolic hydroxyl group of the chromophore to either Asp158 or Asp/Glu160, either directly or via a relay involving a serine side chain (FIG. 8A)[34]. In CyOFP, a Lys side chain, at position 160, rather than an Asp or Glu side chain appears to be the proton acceptor. While Lys is usually classified as a basic amino acid and Asp and Glu as acidic ones, those classifications refer to the neutral forms of the side chains. Asp or Glu, in their anionic states as they are proposed to be in LSS orange-red FPs, would be basic as well, serving as proton acceptors. Based on our structural analysis of CyOFP, we postulate that Lys160 is neutral and also basic. Thus, as with other LSS FPs, CyOFP likely exhibits a blue-shifted absorbance spectrum due to protonation of the chromophore in the ground state, and a large Stokes shift due to an EPST process. The redder absorbance of CyOFP compared to other LSS FPs and its smaller Stokes shift is indicative of differences in molecular orbital energies between the chromophores of CyOFP and the other LSS FPs. This could be due to differences in the positioning of the proton that undergoes ESPT; for example it could be less tightly bound to the phenol group in CyOFP than in other LSS orange-red FPs.

CyOFP addresses a rapidly emerging need for an orange-red fluorophore that can be co-excited with GFP in recently developed microscopy methods. New methods such as random-access two-photon microscopy, adaptive optics, light-sheet microscopy using Bessel beams, optical lattices, and incoherent extended focusing all require dynamic phase modulation of an illumination laser[3-7,11]. Recently, three-photon microscopy has been used to excite GFPs and orange-red FPs at up to 1-mm depth in the brain[42]. All these techniques require custom hardware for each excitation wavelength, making simultaneous dual color imaging cumbersome. Co-expressing CyOFP together with GFP would be an easier way to image two structures or biological events than implementing two excitation wavelengths. For example, in the brain, CyOFP can serve as the basis for a structural marker co-imaged with a GFP-based reporter of calcium, voltage, or neurotransmitter release. This marker can be used for motion correction, especially when using an indicator with a low fluorescence baseline like those of the GCaMP6 family, and for estimating the expression level of the reporter. In non-neuronal cells, CyOFP and GFP can be used to image two different structures, or two different cell populations. CyOFP can thus be added to GFP to visualize a second structure or biological event in various one- or two-photon microscopy methods without requiring any modification to the excitation light path. An additional benefit of truly simultaneous excitation of CyOFP and GFP markers is that temporal analysis does not need to adjust for any time shift in acquisition of different image channels. This should increase accuracy when quantifying correlated events, which may be especially useful when one channel is used as a reference to correct motion- or aberration-induced artifacts.

Our engineering of Antares, a bright orange-red bioluminescent reporter based on a fusion of NanoLuc to CyOFP domains, addresses another long-standing need to improve the sensitivity of BLI in mammals beyond FLuc. FLuc has been used as a reporter gene in mammals for nearly two decades[14], but until this study, no alternative natural or engineered bioluminescent protein had been found to be superior to FLuc in the intensity of signal generated in cells or in mammals in vivo[17-19]. Our comprehensive comparison of luciferases in a mouse tissue phantom, which is also the first experiment to our knowledge to make any comparisons amongst FLuc, Nano-lantern, BRET6, and NanoLuc for red photon output, identifies Antares as the brightest luciferase in terms of red emissions. More importantly, our findings in living mice demonstrate that the in vivo sensitivity limits of BLI have been finally been overcome by Antares, with an 18-fold improvement in detectable emissions over FLuc.

In summary, with its unique combination of cyan excitability and high brightness, CyOFP should be useful in a wide variety of non-linear and light-sheet microscopy applications. In addition, the red-emitting bioluminescent protein Antares created from NanoLuc and CyOFP improves bioluminescence signals in vivo in mammals by greater than an order of magnitude over firefly luciferase, and should be the BLI reporter of choice whenever the highest detection sensitivity is required.

Methods

Mutagenesis and Screening of Libraries.

Mutations for specific residues were introduced by overlap-extension PCR. Mutants were expressed and screened in constitutively active bacterial expression vector pNCS (Allele Biotech). Plasmids were transformed into chemically competent XL-10 Gold (Agilent), and colonies were grown on LB/agar plates at 37° C. for 16-20 hours and at room temperature for an additional 20-24 hours. For each round of mutagenesis, the number of colonies screened was 10-fold the expected library diversity to ensure full coverage. Colonies expressing blue-shifted mNeptune variants were screened for transmitted color by eye and for fluorescence in a dark enclosure with a KL2500 fiber-optic light source (Leica), 610/20-nm excitation and 645/30-nm emission filters (Chroma), and a ST-8300M cooled CCD camera controlled with CCDOps software (Santa Barbara Instrument Group). Colonies expressing large-Stokes shift variants were screened for transmitted color by eye and for fluorescence under blue LED excitation with an orange acrylic filter.

Protein Production and Characterization.

For spectral characterization, bacterial pellets were lysed in B-PER II (Pierce) and hexahistidine-tagged proteins were purified with HisPur Cobalt Resin (Pierce). Proteins were desalted into phosphate-buffered saline (PBS) pH 7.4 using Econo-Pac 10DG gravity flow chromatography columns (Bio-Rad). Absorbance, excitation spectra, and emission spectra were measured with a Lambda35 UV/VIS and LS-55 fluorescence spectrometers (Perkin Elmer). Extinction coefficients were calculated using the base-denaturation method[46]. Quantum yields were determined using cresyl violet in methanol as a standard (QY=0.54). pH titrations were performed using a series of buffers (1 M HOAc, 1 M NaOAc, 5 M NaCl for pH 3.0-4.5; 1 M $NaH_2PO_4$, 1 M $Na_2HPO_4$, 5 M NaCl for pH 5-9.0). In vitro photobleaching measurements were performed in PBS droplets under mineral oil on an IX81 inverted microscope with a 40×/1.15-numerical aperture (NA) water-immersion objective, an X-Cite 120-W metal halide lamp (Lumen Dynamics) at 100% neutral density, a 485/22-nm excitation filter (Omega), and an Orca ER camera (Hamamatsu) controlled by Micro-Manager software. Images were acquired every 1 second under continuous illumination. Times were scaled to produce photon output rates of 1000 per molecule per second as previously described[28].

Fluorescence Lifetime Imaging.

HEK293T cells were transfected using Lipofectamine 2000 with a plasmid encoding CyOFP under the CAG promoter. Cells were imaged using a custom-built two-photon fluorescence lifetime imaging microscope described previously[47]. Briefly, CyOFP was excited with a Ti:sapphire laser (Chameleon, Coherence) tuned at a wavelength of 920 nm, and collected through a photoelectron multiplier tube with low transfer time spread (H7422-40p; Hamamatsu). Fluorescence lifetime images were obtained using a time-correlated single photon counting board (SPC-150; Becker and Hickl) controlled with custom software[48].

Fusion Protein Construction and Imaging.

pCyOFP-N1 and pCyOFP-C1 expression vectors were first constructed based on pEGFP-C1 and pEGFP-N1 (Clontech). Briefly, the CyOFP cDNA was amplified by PCR with a 5' primer encoding an AgeI site and a 3' primer encoding either a BspEI (C1) or NotI (N1) site, and the PCR products were digested, purified, and ligated into similarly treated pEGFP-C1 or pEGFP-N1 vector backbones. Then, to construct plasmids encoding CyOFP fusions, fragments encoding various protein domains were excised from existing plasmids encoding mEmerald fusions using available restriction sites and ligated into similarly treated pCyOFP-N1 and pCyOFP-C1 vector backbones. Domains for fusion proteins were derived from the following sources: human β-actin, NM_001130442.1; human RhoB, NM_004040.2; human H2B, NM_021058.3; human α-tubulin, NM_006082; rat connexin-43, NM_012326.2; rabbit cytochrome p450, XM_002718526.1; human cytochrome C oxidase subunit VIIIA, NM_004074.2; human sialyltransferase, NM_173216.2; c-Ha-Ras, NM_001130442.1; rat F-Tractin, NM_031045.2. For epifluorescence imaging, DNA was prepared using the Plasmid maxi kit (Qiagen) and transfected into HeLa CCL-2 or HeLa S3 cells (ATCC) using Effectene (Qiagen) grown on coverslips in a 50:50 mixture of Dulbecco's modified Eagle's medium (DMEM) and Ham's F12 with 12.5% HyClone Cosmic Calf Serum (GE Healthcare Life Sciences). Cells were fixed after 48 h, mounted with gelvatol[49], and imaged by epifluorescence with an Eclipse 80i microscope (Nikon). For light-sheet imaging, the CyOFP-tractin and cytosolic EGFP constructs were cloned into the pLVX lentiviral vector (Clontech). Viruses were produced and MV3 cells were infected according to the manufacturer's instructions.

Crystallization and Structure Solution of CyOFP.

Prior to crystallization, hexahistadine-CyOFP was purified using size exclusion chromatography to remove aggregation. Thereafter, CyOFP was buffer exchanged with 50 mM Tris (hydroxymethyl)aminomethane, 25 mM NaCl, 4.0 mM TCEP at pH 7.4 and concentrated to 13 mg/mL for crystallization. CyOFP was crystallized at 12° C. in a dark chamber by sitting-drop vapor diffusion against 0.16 M $MgCl$, 0.08 M Tris HCl at pH 8.5, 24% PEG 4000, and 20% glycerol. CyOFP crystals were cryoprotected in paratone oil and flash frozen in liquid nitrogen. X-ray diffraction data were collected at the Advanced Lightsource on SIBYLS Beamline 12.3.1. The crystal structure was solved by molecular replacement using Phaser[50] as part of the CCP4 suite[51]. Models of CyOFP and the fluorophore were built with Coot v0.8.1[52]. Refinement to 2.39 Å was performed in REFMAC5[53] with model rebuilding in Coot. Water molecules were manually added by inspection throughout the refinement process. The final model is composed of 44 water molecules and all residues except residues 1-4 and 233-243 of chain A, 1-6 and 233-243 of chain B, 1-6 and 232-243 of chain C, 1-7 and 232-243 of chain D, as these did not show interpretable electron density. The quality of the model was then analyzed using the programs MolProbity[54] and PROCHECK[55]. The coordinates and reflections are deposited in the PDB with accession code 5BQL.

3D Light Sheet Imaging.

3D collagen samples were created inside a custom agarose mold in order to avoid proximity to stiff surfaces and to reduce refractive index mismatch and light scatter (Welf et al. in review). Briefly, 2% agarose was heated and placed in a rectangular mold containing a cylindrical void for sample containment. Agarose molds were incubated in complete medium prior to sample addition in order to heat the agarose and allow medium components to permeate the agarose. Collagen gels were created by mixing bovine collagen I (Advanced Biomatrix) with concentrated phosphate buffered saline (PBS) and water to create gels of 2.0 mg/mL collagen. This collagen solution was then neutralized with 1N NaOH and mixed with cells just prior to incubation at 37° C. to induce collagen polymerization. Samples were imaged in phenol red-free DMEM with 10% fetal bovine serum and 1× Antibiotic-Antimycotic (Life Technologies) with an one-photon axially swept light-sheet microscope and a two-photon Bessel beam microscope. The one-photon light-sheet microscope illuminates the sample with a tightly focused light-sheet that is scanned in its propagation direction to evenly excite a large field of view in a time-averaged fashion[10]. Illumination and detection objectives had NA of 0.8, yielding an isotropic 3D resolution of 380 nm. The excitation wavelength was 488 nm and dual-emission imaging of GFP and CyOFP was accomplished using two Orca Flash 4.0 CMOS cameras. The two-photon Bessel beam microscope used in this study was conceptually similar to one described by Planchon et al.[8], but featured a much longer Bessel beam (FWHM in propagation direction ~100 μm) and improved telecentric scan optics (Welf et al. in review). Illumination and detection objectives had NA of 0.8, yielding a near-isotropic resolution of ~350 nm. The Bessel beam was scanned five times over the field of view to generate a time-averaged light sheet. No structured illumination was applied; instead for each focal plane only one image was acquired. The excitation wavelength was 900 nm and dual-emission imaging of GFP and CyOFP was accomplished using two Orca Flash 4.0 CMOS cameras. For photostability measurements of CyOFP, powers in the backpupil were 16 µW for one-photon light-sheet microscopy and 92 mW for two-photon Bessel-beam light-sheet microscopy.

Two Photon Functional Imaging of Mouse Primary Visual Cortex In Vivo.

Mouse procedures were performed in accordance with protocols approved by the Janelia Research Campus Institutional Animal Care and Use Committee and Institutional Biosafety Committee. AAV1 vectors expressing CyOFP and GCaMP6s were used to inject the mouse visual cortex as described[37]. 3-4 weeks after virus injection, a cranial window implantation surgery and in vivo functional imaging were performed, following a previously published protocol[37,38]. Mice were anesthetized using isoflurane (2.5% for induction, 1.5-2% during surgery). A 2-2.5 mm-diameter circular craniotomy was placed above V1 (centered 2.7 mm left, and 0.2 mm anterior to Lambda suture). The craniotomy was covered with 1% agarose (Sigma), a 3-mm round no. 1 thickness glass coverslip (Warner Instruments) and a custom titanium head post were cemented to the brain using black dental cement (Contemporary Ortho-Jet). The animal was then placed under the imaging microscope on a blanket warmed to 37° C. and kept anesthetized using 0.5% isoflurane and sedated with 20 µL at 0.33 mg/mL chlorprothixene injected intramuscularly. Imaging was performed with a custom-built two-photon microscope with a resonant scanner. The light source was a Mai Tai HP 100 femtosecond-pulse laser (Spectra-Physics) running at 940 nm. A 16×0.8-NA water-immersion objective (Nikon) was used. Images were acquired using ScanImage 5 (vidriotechnologies.com)[56]. Functional images (512×512 pixels, 250×250 µm$^2$) of layer 2/3 cells (100-250 µm under the pia) were collected at 15 Hz. Maximal laser power was 145 mW at the front aperture of the objective, and satisfactory signal-to-noise images were typically acquired using 5-25 mW. Mice were presented with moving grating stimuli generated using the Psychophysics Toolbox[57] in MATLAB (Mathworks). Each stimulus trial consisted of a 4 s blank period followed by a 4 s drifting sinusoidal grating (0.05 cycles/degree, 1 Hz temporal frequency, 8 different directions). The visual stimuli were presented using an LCD monitor (30×40 cm), placed 25 cm in front of the center of the right eye of the mouse. The monitor subtended an angle of ±38° horizontally and ±31° vertically around the eye of the mouse. Regions of interest corresponding to visually identifiable cell bodies were selected using a semi-automated algorithm, and changes to fluorescence signal were calculated[36-38].

Bioluminescence Imaging.

HEK293A cells were transfected using LipofectamineTX (Life Technologies) with plasmids expressing bioluminescence probes following mTurquoise2 and a P2A sequence. Cells were harvested 48 hours later, and 50000 cells in 10 µL Live Cell Imaging Solution (Life Technologies) were loaded into glass capillary tubes with inner diameter 0.8-1.1 mm (Kimble Chase, cat. #34507-99), centrifuged to the bottom at 500 g for 15 seconds, and then placed on ice prior to imaging. Immediately after adding 10 µL of 20 µM substrate, bioluminescence images were acquired with an IVIS Spectrum (PerkinElmer). Imaging settings were: field of view, 13 cm; aperture, f/1; binning, 2×2; and exposure time, 1 second. At the same time, 78 µL of cells were loaded onto 96-well plate and cyan fluorescence was measured from mTurquoise2 with a Safire2 microplate reader (Tecan). Transfection-normalized bioluminescence signal was calculated as net bioluminescence divided by net fluorescence, where net signal was obtained by integrating signal from a common region of interest encompassing all transfected cells and subtracting the signal from untransfected control cells. For live mouse imaging, livers of 6-7-week old nude mice (strain J:NU #7850 EC, Jackson Laboratories) were hydrodynamically transfected by injecting 20 µg of plasmid DNA in 1.8 mL of saline (0.9% NaCl) into tail veins within 5-6 seconds. 48 hours after injection, bioluminescence images were acquired with an IVIS Spectrum (PerkinElmer). Imaging settings were: field of view, 13 cm; aperture, f/4; binning, 2×2; and exposure time, 2 seconds. Data analysis was performed as with phantom mice above.

TABLE 1

Representative large Stokes shift orange-red FPs.

|  | CyOFP | mBeRFP | LSSmOrange | LSSmKate1 | LSSmKate2 | mKeima |
|---|---|---|---|---|---|---|
| Excitation peak (nm) | 497, 523$^a$ | 446 | 437 | 463 | 460 | 440 |
| Emission peak (nm) | 589 | 611 | 572 | 624 | 605 | 620 |
| ε at peak (mM$^{-1}$ cm$^{-1}$) | 40 | 65 | 52 | 31 | 26 | 13 |
| Φ total | 0.76 | 0.27 | 0.45 | 0.08 | 0.17 | 0.24 |
| Brightness$^b$ | 31 | 18 | 19 | 2.5 | 4.4 | 3.2 |
| Photostability (s)$^c$ | 111 | ND | ND | ND | ND | ND |
| pKa | 5.5 | 5.6 | 5.7 | 3.2 | 2.7 | 6.5 |
| Lifetime (ns) | 3.6 | 2.0 | ND | ND | 1.4$^d$ | 1.8$^d$ |
| Reference | this work | 43 | 44 | 34 | 34 | 45 |

When closely related variants exist, only the brightest one is listed.
ε, extinction coefficient; Φ, quantum yield; ND, not determined.
$^a$CyOFP has a wide excitation plateau with efficiency >95% from 485 to 525 nm. Peaks at 497 and 523 nm differ in excitation efficiency by less than 0.3%.
$^b$Calculated as the product of ε at peak excitation and Φ.
$^c$Predicted time for fluorescence to photobleach by 50% under arc-lamp illumination with intensity adjusted to produce 1,000 emission photons per molecule per second. For EGFP, this time is 170 s.
$^d$Values from ref. 43.

TABLE 2

Specific mutations corresponding to selected characteristics.

| Characteristic | Mutations |
|---|---|
| Stokes shift | M160K |
| Brightness | S21H G42N, M11S M15L, C61H, T94M Y96F L174F, C172V |
| Maturation | H10R C114E, T18S, N21G H23Q, T38K V213H H211Y, S128A, A142P, R179K, L184V, TFINHTQG(68-75)VFIKYPAD |
| Monomericity | T95V, I171H, F191Y, Δ230-237 |
| Photostability | L147M, Δ184-186 |

Commas separate mutations isolated in different rounds. Numbering follows FIG. 1B.

TABLE 3

X-ray diffraction data collection and refinement statistics for CyOFP.

| Parameter | Value |
| --- | --- |
| Space group | $P2_12_12_1$ |
| Cell dimensions | a, b, c (Å) |
| Resolution (Å) | 79.0-2.39 (2.53-2.39 Å) |
| $R_{sym}$* | 0.084 (1.02) |
| I/σ* | 14.8 (1.9) |
| Completeness (%)* | 99.4 (96.8) |
| Redundancy* | 6.5 (6.0) |
| $R_{work}/R_{free}$ | 0.193/0.252 |
| Average B factor | 63.0 |
| RMS deviation, bond lengths (Å | 0.012 |
| RMS deviation, bond angles (°) | 1.83 |

*Statistics for the highest resolution shell are shown in parentheses.

Data were collected at the Advanced Lightsource Beamline 12.3.1 (SIBYLS) with wavelength 1.01623 Å.
Coordinates were deposited at the Protein Data Bank (PDB) with accession number 5BQL.

REFERENCES

1. Newman, R. H., Fosbrink, M. D. & Zhang, J. Genetically encodable fluorescent biosensors for tracking signaling dynamics in living cells. Chem Rev 111, 3614-3666 (2011).
2. Depry, C., Mehta, S. & Zhang, J. Multiplexed visualization of dynamic signaling networks using genetically encoded fluorescent protein-based biosensors. Pflugers Arch 465, 373-381 (2013).
3. Shao, L., Kner, P., Rego, E. H. & Gustafsson, M. G. Super-resolution 3D microscopy of live whole cells using structured illumination. Nat Methods 8, 1044-1046 (2011).
4. Liu, Y. et al. Optical focusing deep inside dynamic scattering media with near-infrared time-reversed ultrasonically encoded (TRUE) light. Nat Commun 6, 5904 (2015).
5. Si, K., Fiolka, R. & Cui, M. Fluorescence imaging beyond the ballistic regime by ultrasound pulse guided digital phase conjugation. Nat Photonics 6, 657-661 (2012).
6. Ji, N., Milkie, D. E. & Betzig, E. Adaptive optics via pupil segmentation for high-resolution imaging in biological tissues. Nat Methods 7, 141-147 (2010).
7. Katona, G. et al. Fast two-photon in vivo imaging with three-dimensional random-access scanning in large tissue volumes. Nat Methods 9, 201-208 (2012).
8. Planchon, T. A. et al. Rapid three-dimensional isotropic imaging of living cells using Bessel beam plane illumination. Nat Methods 8, 417-423 (2011).
9. Chen, B. C. et al. Lattice light-sheet microscopy: imaging molecules to embryos at high spatiotemporal resolution. Science 346, 1257998 (2014).
10. Dean, K. M., Roudot, P., Welf, E. S., Danuser, G. & Fiolka, R. Deconvolution-free Subcellular Imaging with Axially Swept Light Sheet Microscopy. Biophysical Journal 108, 1-9 (2015).
11. Dean, K. M. & Fiolka, R. Uniform and scalable light-sheets generated by extended focusing. Opt Express 22, 26141-26152 (2014).
12. Close, D. M., Xu, T., Sayler, G. S. & Ripp, S. In vivo bioluminescent imaging (BLI): noninvasive visualization and interrogation of biological processes in living animals. Sensors (Basel) 11, 180-206 (2011).
13. Zhao, H. et al. Emission spectra of bioluminescent reporters and interaction with mammalian tissue determine the sensitivity of detection in vivo. J Biomed Opt 10, 41210 (2005).
14. Contag, C. H. et al. Visualizing gene expression in living mammals using a bioluminescent reporter. Photochem Photobiol 66, 523-531 (1997).
15. Ando, Y., Niwa, K., Yamada, N., Enomoto, T. & Irie . . . , T. Firefly bioluminescence quantum yield and colour change by pH-sensitive green emission. Nature Photonics 2, 44-47 (2007).
16. Branchini, B. R., Magyar, R. A., Murtiashaw, M. H., Anderson, S. M. & Zimmer, M. Site-directed mutagenesis of histidine 245 in firefly luciferase: a proposed model of the active site. Biochemistry 37, 15311-15319 (1998).
17. Liang, Y., Walczak, P. & Bulte, J. W. Comparison of red-shifted firefly luciferase Ppy RE9 and conventional Luc2 as bioluminescence imaging reporter genes for in vivo imaging of stem cells. J Biomed Opt 17, 016004 (2012).
18. Mazo-Vargas, A., Park, H., Aydin, M. & Buchler, N. E. Measuring fast gene dynamics in single cells with time-lapse luminescence microscopy. Mol Biol Cell 25, 3699-3708 (2014).
19. Mezzanotte, L. et al. Evaluating reporter genes of different luciferases for optimized in vivo bioluminescence imaging of transplanted neural stem cells in the brain. Contrast Media Mol Imaging 8, 505-513 (2013).
20. Matthews, J. C., Hori, K. & Cormier, M. J. Purification and properties of Renilla reniformis luciferase. Biochemistry 16, 85-91 (1977).
21. Shimomura, O., Johnson, F. H. & Masugi, T. Cypridina bioluminescence: light-emitting oxyluciferin-luciferase complex. Science 164, 1299-1300 (1969).
22. Loening, A. M., Dragulescu-Andrasi, A. & Gambhir, S. S. A red-shifted Renilla luciferase for transient reporter-gene expression. Nat Methods 7, 5-6 (2010).
23. Shimomura, O., Masugi, T., Johnson, F. H. & Haneda, Y. Properties and reaction mechanism of the bioluminescence system of the deep-sea shrimp Oplophorus gracilorostris. Biochemistry 17, 994-998 (1978).
24. Hall, M. P. et al. Engineered luciferase reporter from a deep sea shrimp utilizing a novel imidazopyrazinone substrate. ACS Chem Biol 7, 1848-1857 (2012).
25. Ward, W. W. & Cormier, M. J. Energy transfer via protein-protein interaction in renilla bioluminescence. Photochemistry and Photobiology 27, 389-396 (1978).
26. Dragulescu-Andrasi, A., Chan, C. T., De, A., Massoud, T. F. & Gambhir, S. S. Bioluminescence resonance energy transfer (BRET) imaging of protein-protein interactions within deep tissues of living subjects. Proc Natl Acad Sci USA 108, 12060-12065 (2011).
27. Saito, K. et al. Luminescent proteins for high-speed single-cell and whole-body imaging. Nat Commun 3, 1262 (2012).
28. Chu, J. et al. Non-invasive intravital imaging of cellular differentiation with a bright red-excitable fluorescent protein. Nat Methods 11, 572-578 (2014).
29. Bruno, T. J. & Svoronos, P. D. N. CRC handbook of fundamental spectroscopic correlation charts (CRC Press, Boca Raton, Fla., 2006).
30. Chu, J., Xing, Y. & Lin, M. Z. in The Fluorescent Protein Revolution (eds Day, R. & Davidson, M.) 153-167 (United States, 2014).

31. Baird, G. S., Zacharias, D. A. & Tsien, R. Y. Biochemistry, mutagenesis, and oligomerization of DsRed, a red fluorescent protein from coral. *Proc Natl Acad Sci USA* 97, 11984-11989 (2000).
32. Lounis, B. & Moerner, W. E. Single photons on demand from a single molecule at room temperature. *Nature* 407, 491-493 (2000).
33. Miyawaki, A., Shcherbakova, D. M. & Verkhusha, V. V. Red fluorescent proteins: chromophore formation and cellular applications. *Curr Opin Struct Biol* 22, 679-688 (2012).
34. Piatkevich, K. D., Malashkevich, V. N., Almo, S. C. & Verkhusha, V. V. Engineering ESPT pathways based on structural analysis of LSSmKate red fluorescent proteins with large Stokes shift. *J Am Chem Soc* 132, 10762-10770 (2010).
35. Lam, A. J. et al. Improving FRET dynamic range with bright green and red fluorescent proteins. *Nat Methods* 9, 1005-1012 (2012).
36. Akerboom, J. et al. Optimization of a GCaMP calcium indicator for neural activity imaging. *J Neurosci* 32, 13819-13840 (2012).
37. Chen, T. W. et al. Ultrasensitive fluorescent proteins for imaging neuronal activity. *Nature* 499, 295-300 (2013).
38. Dana, H. et al. Thy1-GCaMP6 transgenic mice for neuronal population imaging in vivo. *PLoS One* 9, e108697 (2014).
39. Gao, L. et al. Noninvasive imaging beyond the diffraction limit of 3D dynamics in thickly fluorescent specimens. *Cell* 151, 1370-1385 (2012).
40. Morse, D. & Tannous, B. A. A water-soluble coelenterazine for sensitive in vivo imaging of coelenterate luciferases. *Mol Ther* 20, 692-693 (2012).
41. Otto-Duessel, M. et al. In vivo testing of *Renilla* luciferase substrate analogs in an orthotopic murine model of human glioblastoma. *Mol Imaging* 5, 57-64 (2006).
42. Horton, N. G. et al. three-photon microscopy of subcortical structures within an intact mouse brain. *Nat Photonics* 7, (2013).
43. Yang, J. et al. mBeRFP, an improved large stokes shift red fluorescent protein. *PLoS One* 8, e64849 (2013).
44. Shcherbakova, D. M., Hink, M. A., Joosen, L., Gadella, T. W. & Verkhusha, V. V. An orange fluorescent protein with a large Stokes shift for single-excitation multicolor FCCS and FRET imaging. *J Am Chem Soc* 134, 7913-7923 (2012).
45. Kogure, T. et al. A fluorescent variant of a protein from the stony coral Montipora facilitates dual-color single-laser fluorescence cross-correlation spectroscopy. *Nat Biotechnol* 24, 577-581 (2006).
46. Chalfie, M. & Kain, S. R. *Green Fluorescent Protein: Properties, Applications, and Protocols* (Wiley-Liss, 1998).
47. Yasuda, R. Imaging spatiotemporal dynamics of neuronal signaling using fluorescence resonance energy transfer and fluorescence lifetime imaging microscopy. *Curr Opin Neurobiol* 16, 551-561 (2006).
48. Yasuda, R. et al. Supersensitive Ras activation in dendrites and spines revealed by two-photon fluorescence lifetime imaging. *Nat Neurosci* 9, 283-291 (2006).
49. Harlow, E. & Lane, D. Mounting samples in gelvatol or mowiol. *CSH Protoc* 2006, (2006).
50. McCoy, A. J. et al. Phaser crystallographic software. *J Appl Crystallogr* 40, 658-674 (2007).
51. Winn, M. D. et al. Overview of the CCP4 suite and current developments. *Acta Crystallogr D Biol Crystallogr* 67, 235-242 (2011).
52. Emsley, P. & Cowtan, K. Coot: model-building tools for molecular graphics. *Acta Crystallogr D Biol Crystallogr* 60, 2126-2132 (2004).
53. Murshudov, G. N., Vagin, A. A. & Dodson, E. J. Refinement of macromolecular structures by the maximum-likelihood method. *Acta Crystallogr D Biol Crystallogr* 53, 240-255 (1997).
54. Chen, V. B. et al. MolProbity: all-atom structure validation for macromolecular crystallography. *Acta Crystallogr D Biol Crystallogr* 66, 12-21 (2010).
55. Laskowski, R. A., Moss, D. S. & Thornton, J. M. Main-chain bond lengths and bond angles in protein structures. *J Mol Biol* 231, 1049-1067 (1993).
56. Pologruto, T. A., Sabatini, B. L. & Svoboda, K. Scanlmage: flexible software for operating laser scanning microscopes. *Biomed Eng Online* 2, 13 (2003).
57. Brainard, D. H. The Psychophysics Toolbox. *Spat Vis* 10, 433-436 (1997).

While the preferred embodiments of the invention have been illustrated and described, it will be appreciated that various changes can be made therein without departing from the spirit and scope of the invention.

What is claimed is:

1. An orange-red fluorescent protein comprising a polypeptide selected from the group consisting of:
   a) a polypeptide comprising the amino acid sequence of SEQ ID NO:1; and
   b) a polypeptide comprising an amino acid sequence having at least 95% identity to the amino acid sequence of SEQ ID NO:1, wherein the orange-red fluorescent protein emits light in response to absorption of cyan excitation light.

2. A fusion protein comprising the orange-red fluorescent protein of claim 1 connected to a polypeptide of interest.

3. A fusion protein comprising the orange-red fluorescent protein of claim 1 connected to a targeting sequence directing localization to a specific cellular compartment or protein.

4. The fusion protein of claim 2, further comprising a targeting sequence directing localization to a specific subcellular compartment or protein.

5. A bioluminescent fusion protein comprising at least one orange-red fluorescent protein according to claim 1 connected to at least one luciferase, wherein the orange-red fluorescent protein or proteins are operably linked to the luciferase or luciferases to allow bioluminescence resonance energy transfer (BRET) from a luciferase reaction product to the orange-red fluorescent protein or proteins upon reaction of a chemiluminescent substrate by the luciferase or luciferases.

6. The bioluminescent fusion protein of claim 5, wherein the luciferase or luciferases comprise a polypeptide selected from the group consisting of:
   a) a polypeptide comprising the amino acid sequence of SEQ ID NO:3; and
   b) a polypeptide comprising an amino acid sequence having at least 95% identity to the amino acid sequence of SEQ ID NO:3, wherein the orange-red fluorescent protein emits light in response to absorption of cyan excitation light.

7. The bioluminescent fusion protein of claim 6 comprising a polypeptide selected from the group consisting of:
   a) a polypeptide comprising the amino acid sequence of SEQ ID NO:2; and
   b) a polypeptide comprising an amino acid sequence having at least 95% identity to the amino acid sequence of SEQ ID NO:2, wherein the orange-red fluorescent protein emits light in response to absorption of cyan excitation light.

8. The bioluminescent fusion protein of claim 5, wherein a targeting sequence directs localization of the fusion protein to a specific tissue, cell-type, cellular compartment, or protein.

9. A method of using the orange-red fluorescent protein of claim 1 for fluorescence reporting, the method comprising:
   a) introducing the orange-red fluorescent protein of claim 1 into a cell or animal by injection of the protein or introduction of a vector expressing the protein; and
   b) illuminating the cell or animal with light that produces fluorescence from the protein; and
   c) detecting fluorescence emitted by the protein.

10. The method of claim 9, wherein a fluorescence image is visualized with an optical microscope, a digital microscope, a charged coupled device (CCD) image sensor, a complementary metal-oxide-semiconductor (CMOS) image sensor, a digital camera, a fiber-optic imaging system, or a medical imaging system.

11. The method of claim 9, further comprising:
   a) introducing both a green fluorescent protein and the orange-red fluorescent protein of claim 1 into a cell or animal, such that either protein is introduced by injection or expression from a vector; and
   b) illuminating the cell or animal with light that produces fluorescence from both the orange-red fluorescent protein and the green fluorescent protein simultaneously; and
   c) recording the orange-red fluorescence emitted by the orange-red fluorescent protein and green fluorescence emitted by the green fluorescent protein.

12. The method of claim 11, wherein a fluorescence image is visualized with an optical microscope, a digital microscope, a charged coupled device (CCD) image sensor, a complementary metal-oxide-semiconductor (CMOS) image sensor, a digital camera, a fiber-optic imaging system, or a medical imaging system.

13. A method for using the bioluminescent fusion protein of claim 5 for bioluminescence reporting, the method comprising:
   a) introducing the bioluminescent fusion protein of claim 5 into a cell or animal by injection of the protein or introduction of a vector expressing the protein; and
   b) contacting the bioluminescent fusion protein with the chemiluminescent substrate of claim 5 in the cell or animal; and
   c) recording bioluminescence from the cell or animal by detecting bioluminescence emitted from the fusion protein.

14. The method of claim 13, wherein a bioluminescence image is visualized with an optical microscope, a digital microscope, a charged coupled device (CCD) image sensor, a complementary metal-oxide-semiconductor (CMOS) image sensor, a digital camera, a fiber-optic imaging system, or a medical imaging system.

* * * * *